(12) United States Patent  
Walter et al.

(10) Patent No.: US 10,093,967 B2  
(45) Date of Patent: Oct. 9, 2018

(54) DETECTION OF NUCLEIC ACIDS

(71) Applicant: The Regents of The University of Michigan, Ann Arbor, MI (US)

(72) Inventors: Nils Walter, Ann Arbor, MI (US); Alexander Johnson-Buck, Brighton, MA (US); Mario Blanco, Pasadena, CA (US); Arlie Rinaldi, Pasadena, CA (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/589,467

(22) Filed: Jan. 5, 2015

(65) Prior Publication Data

US 2016/0046988 A1 Feb. 18, 2016

Related U.S. Application Data

(60) Provisional application No. 62/078,766, filed on Nov. 12, 2014, provisional application No. 62/036,480, filed on Aug. 12, 2014.

(51) Int. Cl.
*C12Q 1/68* (2018.01)
*C12Q 1/6837* (2018.01)
*C12Q 1/6816* (2018.01)

(52) U.S. Cl.
CPC ......... *C12Q 1/6837* (2013.01); *C12Q 1/6816* (2013.01)

(58) Field of Classification Search
None
See application file for complete search history.

(56) References Cited

U.S. PATENT DOCUMENTS

| | | |
|---|---|---|
| 4,415,732 A | 11/1983 | Caruthers et al. |
| 4,458,066 A | 7/1984 | Caruthers et al. |
| 4,542,102 A | 9/1985 | Dattagupta et al. |
| 4,725,677 A | 2/1988 | Koster et al. |
| 4,937,188 A | 6/1990 | Giese et al. |
| 4,973,679 A | 11/1990 | Caruthers et al. |
| 4,980,460 A | 12/1990 | Molko et al. |
| 5,011,770 A | 4/1991 | Kung et al. |
| 5,143,854 A | 9/1992 | Pirrung et al. |
| 5,252,743 A | 10/1993 | Barrett et al. |
| 5,412,087 A | 5/1995 | McGall et al. |

(Continued)

FOREIGN PATENT DOCUMENTS

| | | |
|---|---|---|
| EP | 2300983 | 5/2012 |
| EP | 2837695 A1 | 2/2015 |

(Continued)

OTHER PUBLICATIONS

Johnson-Buck et al, Nano Lett., vol. 13, pp. 728-733, Jan. 28, 20132.*

(Continued)

*Primary Examiner* — Robert T. Crow
(74) *Attorney, Agent, or Firm* — Casimir Jones S.C.; Thomas Isenbarger

(57) ABSTRACT

Provided herein is technology relating to detecting and identifying nucleic acids and particularly, but not exclusively, to compositions, methods, kits, and systems for detecting, identifying, and quantifying target nucleic acids with high confidence at single-molecule resolution.

24 Claims, 10 Drawing Sheets

Specification includes a Sequence Listing.

(56) References Cited

U.S. PATENT DOCUMENTS

| | | | |
|---|---|---|---|
| 5,436,327 A | 7/1995 | Southern et al. | |
| 5,445,934 A | 8/1995 | Fodor et al. | |
| 5,601,980 A | 2/1997 | Gordon et al. | |
| 5,604,097 A | 2/1997 | Brenner et al. | |
| 5,624,711 A | 4/1997 | Sundberg et al. | |
| 5,635,400 A | 6/1997 | Brenner et al. | |
| 5,654,413 A | 8/1997 | Brenner et al. | |
| 5,695,934 A | 12/1997 | Brenner et al. | |
| 5,744,305 A | 4/1998 | Fodor et al. | |
| 5,972,612 A * | 10/1999 | Malmqvist | C12Q 1/6825 435/6.14 |
| 6,001,983 A | 12/1999 | Benner | |
| 7,935,822 B2 | 5/2011 | Arden-Jacob | |
| 8,198,604 B2 | 6/2012 | Mertz | |
| 8,846,924 B2 | 9/2014 | Zilles et al. | |
| 2002/0022217 A1 | 2/2002 | Sabanayagan et al. | |
| 2003/0003486 A1 | 1/2003 | Sauer et al. | |
| 2003/0148519 A1 | 8/2003 | Engelke et al. | |
| 2003/0175740 A1* | 9/2003 | Mullinax | C12Q 1/6837 435/6.12 |
| 2005/0053942 A1* | 3/2005 | Kauppinen | C12N 15/1006 435/6.12 |
| 2005/0244863 A1* | 11/2005 | Mir | B01J 19/0046 435/6.11 |
| 2006/0179585 A1 | 8/2006 | Zilles et al. | |
| 2009/0084980 A1 | 4/2009 | Mertz | |
| 2011/0172420 A1 | 7/2011 | Zilles et al. | |
| 2011/0190486 A1 | 8/2011 | Zilles et al. | |
| 2011/0223677 A1 | 9/2011 | Pojer et al. | |
| 2013/0011833 A1* | 1/2013 | Quake | C12Q 1/6804 435/6.11 |
| 2013/0012527 A1 | 1/2013 | Breaker et al. | |
| 2013/0071837 A1* | 3/2013 | Winters-Hilt | C12Q 1/6869 435/6.11 |
| 2015/0051105 A1 | 2/2015 | Ueno et al. | |

FOREIGN PATENT DOCUMENTS

| | | |
|---|---|---|
| WO | 90/07582 | 7/1990 |
| WO | 90/15070 | 12/1990 |
| WO | 91/00868 | 1/1991 |
| WO | 91/07087 | 5/1991 |
| WO | 1997004129 A1 | 2/1997 |
| WO | 2008030071 A1 | 3/2008 |
| WO | 2013/153911 A1 | 10/2013 |
| WO | 2014/018584 A1 | 1/2014 |
| WO | 2016025477 A1 | 2/2016 |
| WO | 2016172727 A1 | 10/2016 |
| WO | 2017139354 A1 | 8/2017 |

OTHER PUBLICATIONS

Jungmann et al, Nano Letters, 2010, vol. 10, pp. 4756-4761, plus Supporting Information pp. 1-18.*

International Search Report for PCT/2015/044650 dated Dec. 29, 2015, 17 pages.

Johnson-Buck et al., "Kinetic fingerprinting to identify and count single nucleic acids." Nat Biotechnol. Jul. 2015;33(7):730-2.

Park et al. "Kinetic and affinity analyses of hybridization reactions between peptide nucleic acid probes and DNA targets using surface plasmon field-enhanced fluorescence spectroscopy" Biointerphases. Dec. 2006;1(4):113-22.

Abelson et al., "Conformational dynamics of single pre-mRNA molecules during in vitro splicing." Nat Struct Mol Biol. Apr. 2010; 17(4):504-12.

Adessi et al., "Solid phase DNA amplification: characterisation of primer attachment and amplification mechanisms." Nucleic acids research, 28(20): e87, 2000.

Albert L. Lehninger: Principles of Biochemistry, Worth Pub. 1982, pp. 793-800.

Allawi et al., "Thermodynamics and NMR of internal G.T mismatches in DNA." Biochemistry. Aug. 26, 1997; 36(34):10581-94.

Anderson & Young. "Quantitative Filter Hybridization in Nucleic Acid Hybridization: A Practical Approach, RD. Hames and SJ Higgens, editors." (1985), p. 80.

Beaucage et al., "Advances in the Synthesis of Oligonucleotides by the Phosphoramidite Approach" Tetrahedron Mar. 20, 1992, 48(12): 2223-2311.

Call et al., "Fabrication of DNA microarrays using unmodified oligonucleotide probes." Biotechniques. Feb. 2001; 30 (2):368-72.

Canny, "A Computational Approach to Edge Detection" IEEE Transactions on Pattern Analysis and Machine Intelligence. 8(6): 679-698, 1986.

Carrington et al., "Role of MicroRNAs in Plant and Animal Development" Science 2003, 301:336-338.

Chan et al., "Direct quantification of single-molecules of microRNA by total internal reflection fluorescence microscopy." Anal Chem. Aug. 15, 2010; 82(16):6911-8.

Cullen, "RNA interference: antiviral defense and genetic tool." Nat Immunol. Jul. 2002; 3(7):597-9.

Doty et al., "Strand Separation and Specific Recombination in Deoxyribonucleic Acids: Physical Chemical Studies." Proc Natl Acad Sci U S A. Apr. 1960; 46(4):461-76.

Elbashir, "Functional anatomy of siRNAs for mediating efficient RNAi in Drosophila melanogaster embryo lysate." EMBO J. Dec. 3, 2001; 20(23):6877-88.

Fodor et al., "Light-directed, spatially addressable parallel chemical synthesis." Science. Feb. 15, 1991; 251(4995):767-73.

Grishok et al., "Genes and mechanisms related to RNA interference regulate expression of the small temporal RNAs that control C. elegans developmental timing." Cell. Jul. 13, 2001; 106(1):23-34.

Gunnarsson et al., "Single-molecule detection and mismatch discrimination of unlabeled DNA targets." Nano Lett. Jan. 2008;8(1):183-8.

Guo et al., "Direct fluorescence analysis of genetic polymorphisms by hybridization with oligonucleotide arrays on glass supports." Nucleic Acids Res. Dec. 11, 1994; 22(24):5456-65.

Haugland, Richard P. The handbook: a guide to fluorescent probes and labeling technologies. Molecular probes, 2005.

Hutvágner et al., "A cellular function for the RNA-interference enzyme Dicer in the maturation of the let-7 small temporal RNA." Science. Aug. 3, 2001; 293(5531):834-8.

Iorio & Croce, "MicroRNA dysregulation in cancer: diagnostics, monitoring and therapeutics. A comprehensive review." EMBO Mol Med. Mar. 2012; 4(3):143-59.

Ketting et al., "Dicer functions in RNA interference and in synthesis of small RNA involved in developmental timing in C. elegans." Genes Dev. Oct. 15, 2001; 15(20):2654-9.

Khvorova et al., "Functional siRNAs and miRNAs exhibit strand bias." Cell. Oct. 17, 2003; 115(2):209-16.

Lagos-Quintana et al., "Identification of tissue-specific microRNAs from mouse." Curr Biol. Apr. 30, 2002; 12(9):735-9.

Lau et al., "An abundant class of tiny RNAs with probable regulatory roles in Caenorhabditis elegans." Science. Oct. 26, 2001; 294(5543):858-62.

Lee & Ambros, "An Extensive Class of Small RNAs in Caenorhabditis elegans" Science, Oct. 26, 2001, 294:862-864.

Lee et al., "MicroRNA maturation: stepwise processing and subcellular localization." EMBO J. Sep. 2, 2002; 21(17):4663-70.

Lin & Brown, "Synthesis and duplex stability of oligonucleotides containing cytosine-thymine analogues." Nucleic Acids Res. Dec. 25, 1989; 17(24):10373-83.

Lin & Brown, "Synthesis of oligodeoxyribonucleotides containing degenerate bases and their use as primers in the polymerase chain reaction." Nucleic Acids Res. Oct. 11, 1992; 20(19):5149-52.

Marmur & Lane, "Strand Separation and Specific Recombination in Deoxyribonucleic Acids: Biological Studies." Proc Natl Acad Sci U S A. Apr. 1960; 46(4):453-61.

Mead et al., Introduction to VLSI systems. vol. 802. Reading, MA: Addison-Wesley, 1980.

Michelotti et al., "A bird's eye view tracking slow nanometer-scale movements of single molecular nano-assemblies." Methods Enzymol. 2010; 475:121-48.

(56) References Cited

OTHER PUBLICATIONS

Mitchell et al., "Circulating microRNAs as stable blood-based markers for cancer detection." Proc Natl Acad Sci U S A. Jul. 29, 2008; 105(30):10513-8.
Østergaard & Hrdlicka, "Pyrene-functionalized oligonucleotides and locked nucleic acids (LNAs): tools for fundamental research, diagnostics, and materials science." Chem Soc Rev. Dec. 2011; 40(12):5771-88.
Paranjape et al., "MicroRNAs: tools for cancer diagnostics" Gut. Nov. 2009; 58(11): 1546-1554.
Pasquinelli et al., "Conservation of the sequence and temporal expression of let-7 heterochronic regulatory RNA." Nature. Nov. 2, 2000; 408(6808):86-9.
Paul et al., "Effective expression of small interfering RNA in human cells." Nat Biotechnol. May 2002;20(5):505-8.
Piliarik & Sandoghdar, "Direct optical sensing of single unlabelled proteins and super-resolution imaging of their binding sites." Nat Commun. Jul. 29, 2014; 5:4495.
Schwarzenbach et al., "Cell-free nucleic acids as biomarkers in cancer patients." Nat Rev Cancer. Jun. 2011; 11(6):426-37.
Schweitzer & Kool, "Aromatic Nonpolar Nucleosides as Hydrophobic Isosteres of Pyrimidine and Purine Nucleosides." J Org Chem. Dec. 1, 1994;59(24):7238-7242.
Schweitzer & Kool, "Hydrophobic, Non-Hydrogen-Bonding Bases and Base Pairs in DNA." J Am Chem Soc. Feb. 22, 1995; 117(7):1863-1872.
Stahlhut & Slack, "MicroRNAs and the cancer phenotype: profiling, signatures and clinical implications." Genome Med. Dec. 30, 2013; 5(12):111.
Sui et al., "An ultra-sensitive DNA assay based on single-molecule detection coupled with hybridization accumulation and its application." Analyst. Oct. 7, 2011; 136(19):3950-5.
Sze, VLSI technology, McGraw-Hill, 1983.
Tan et al., "Molecular beacons." Curr Opin Chem Biol. Oct. 2004; 8(5):547-53.
Trcek et al., "Single-mRNA counting using fluorescent in situ hybridization in budding yeast." Nat Protoc. Feb. 2, 2012; 7(2):408-19.
Xie et al., "miRCancer: a microRNA-cancer association database constructed by text mining on literature." Bioinformatics. Mar. 1, 2013; 29(5):638-44.
Zhang et al., "Optimizing the specificity of nucleic acid hybridization." Nat Chem. Jan. 22, 2012; 4(3):208-14.
Ditzler et al., "A rugged free energy landscape separates multiple functional RNA folds throughout denaturation." Nucleic Acids Res. Dec. 2008;36(22):7088-99.
Marek et al., "The shape-shifting quasispecies of RNA: one sequence, many functional folds." Phys Chem Chem Phys. Jun. 28, 2011;13(24):11524-37.
McKinney et al., "Structural dynamics of individual Holliday junctions." Nat Struct Biol. Feb. 2003;10(2):93-7.
Solomatin et al., "Multiple native states reveal persistent ruggedness of an RNA folding landscape." Nature. Feb. 4, 2010;463(7281):681-4.
Zhuang et al., "Correlating Structural Dynamics and Function in Single Ribozyme Molecules" Science. May 24, 2002;296(5572):1473-6.
Dupuis et al., "Single-molecule kinetics reveal cation-promoted DNA duplex formation through ordering of single-stranded helices." Biophys J. Aug. 6, 2013;105(3):756-66.
Palau et al., "Single-cycle kinetic analysis of ternary DNA complexes by surface plasmon resonance on a decaying surface." Biochimie. Sep. 2012;94(9):1891-9.
Taton et al., "Scanometric DNA array detection with nanoparticle probes." Science. Sep. 8, 2000;289(5485):1757-60.
Athamanolap et al., "Trainable high resolution melt curve machine learning classifier for large-scale reliable genotyping of sequence variants." PLoS One. Oct. 2, 2014;9(9):e109094.
Search Report of related EP 15832556.3, dated Feb. 13, 2018, 12 pages.
Nasef et al., "Melting temperature of surface-tethered DNA." Anal Biochem. Nov. 1, 2010;406(1):34-40.
Selleck et al., "Biophysical Characterization and Direct Delivery of S. pyogenesCas9 Ribonucleoprotein Complexes" Mol Ther, Apr. 27, 2015 (Apr. 27, 2015), vol. 23, Suppl. 1, p. S66.
Search Report of related PCT/US2017/016977, dated Apr. 25, 2017, 19 pages.
Anders et al., "Structural basis of PAM-dependent target DNA recognition by the Cas9 endonuclease" Nature. Sep. 25, 2014;513(7519):569-73.

\* cited by examiner let-7a let-7c

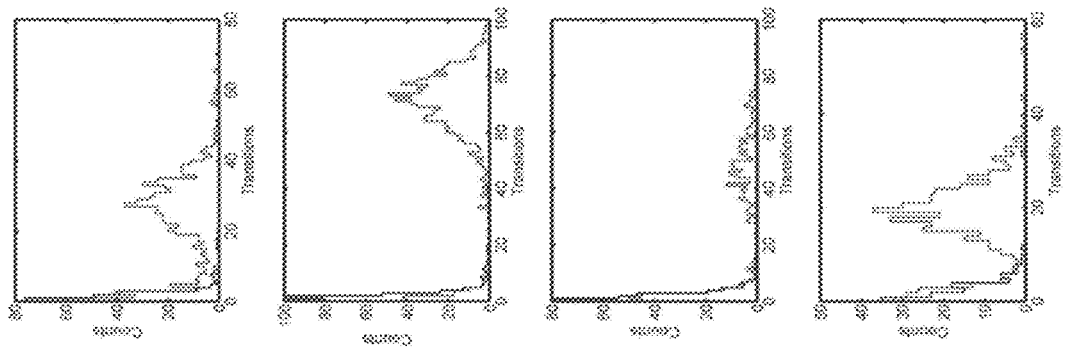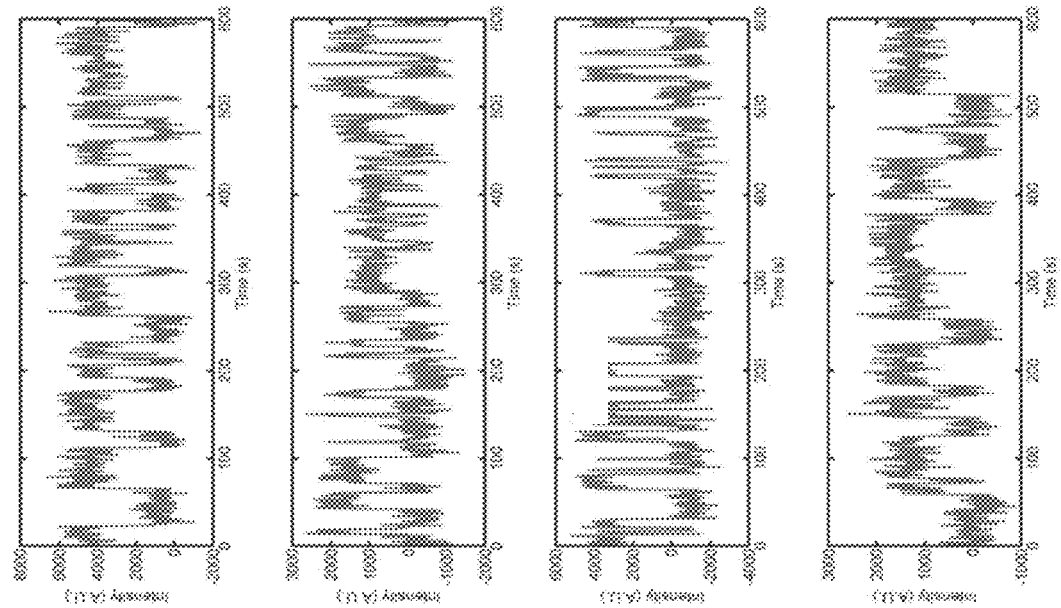

Fig. 5A
*hsa-let-7a*

(SEQ ID NO. 1) 5'-P/UGAGGUAGUAGGUUGUAUAGUU
/3-biotin/ACTCCATCAT CAACATATCA-Cy5
(SEQ ID NO. 10) (SEQ ID NO. 6)

Fig. 5B
*hsa-miR-16*

(SEQ ID NO. 3) 5'-P/UAGCAGCACGUAAAUAUUGGCG
/3-biotinTEG/ATCGTCGTGC TTATAACCGC-Cy5
(SEQ ID NO. 11) (SEQ ID NO. 7)

Fig. 5C
*hsa-miR-21*

(SEQ ID NO. 4) 5'-P/UAGCUUAUCAGACUGAUGUUGA
CTACAACT-Cy5
/3-biotinTEG/ATCGAATAGTC (SEQ ID NO. 8)
(SEQ ID NO. 12)

Fig. 5D
*cel-miR-39*

(SEQ ID NO. 5) 5'-P/UCACCGGGUGUAAAUCAGCUUG
/3-biotinTEG/AGTGGCCCA TTAGTCGAAC-Cy5
(SEQ ID NO. 13) (SEQ ID NO. 9)

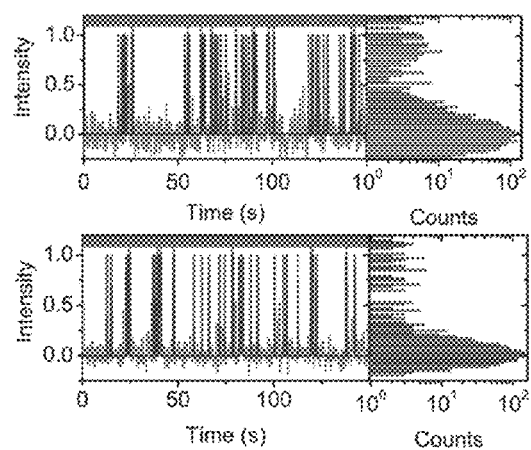 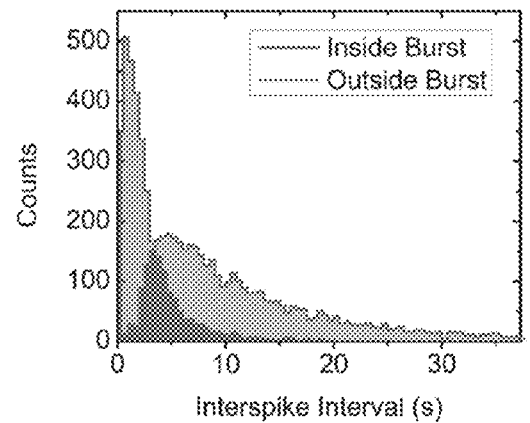
Fig. 7A                    Fig. 7B

SEQUENCE LISTING

```
<160> NUMBER OF SEQ ID NOS: 13

<210> SEQ ID NO 1
<211> LENGTH: 22
<212> TYPE: RNA
<213> ORGANISM: Homo sapiens

<400> SEQUENCE: 1
ugagguagua gguuguauag uu                                              22

<210> SEQ ID NO 2
<211> LENGTH: 22
<212> TYPE: RNA
<213> ORGANISM: Homo sapiens

<400> SEQUENCE: 2
ugagguagua gguuguaugg uu                                              22

<210> SEQ ID NO 3
<211> LENGTH: 22
<212> TYPE: RNA
<213> ORGANISM: Homo sapiens

<400> SEQUENCE: 3
uagcagcacg uaaauauugg cg                                              22

<210> SEQ ID NO 4
<211> LENGTH: 22
<212> TYPE: RNA
<213> ORGANISM: Homo sapiens

<400> SEQUENCE: 4
uagcuuauca gacugauguu ga                                              22

<210> SEQ ID NO 5
<211> LENGTH: 22
<212> TYPE: RNA
<213> ORGANISM: Caenorhabditis elegans

<400> SEQUENCE: 5 ucaccggguq uaaaucagcu ug                                              22

<210> SEQ ID NO 6
<211> LENGTH: 10
<212> TYPE: DNA
<213> ORGANISM: Homo sapiens
```

```
<400> SEQUENCE: 6
actatacaac                                                              10

<210> SEQ ID NO 7
<211> LENGTH: 9
<212> TYPE: DNA
<213> ORGANISM: Homo sapiens

<400> SEQUENCE: 7 gccaatatt                                                                9

<210> SEQ ID NO 8
<211> LENGTH: 8
<212> TYPE: DNA
<213> ORGANISM: Homo sapiens

<400> SEQUENCE: 8 tcaacatc                                                                 8

<210> SEQ ID NO 9
<211> LENGTH: 10
<212> TYPE: DNA
<213> ORGANISM: Caenorhabditis elegans

<400> SEQUENCE: 9
aagctgattt                                                              10

<210> SEQ ID NO 10
<211> LENGTH: 10
<212> TYPE: DNA
<213> ORGANISM: Homo sapiens

<400> SEQUENCE: 10
tactacctca                                                              10

<210> SEQ ID NO 11
<211> LENGTH: 10
<212> TYPE: DNA
<213> ORGANISM: Homo sapiens

<400> SEQUENCE: 11
cgtgctgcta                                                              10

<210> SEQ ID NO 12
<211> LENGTH: 11
<212> TYPE: DNA
<213> ORGANISM: Homo sapiens

<400> SEQUENCE: 12
ctgataagct a                                                            11

<210> SEQ ID NO 13
<211> LENGTH: 9
<212> TYPE: DNA
<213> ORGANISM: Caenorhabditis elegans

<400> SEQUENCE: 13 acccggtga                                                                9
```

DETECTION OF NUCLEIC ACIDS

This application claims priority to U.S. provisional patent application Ser. No. 62/036,480, filed Aug. 12, 2014, and U.S. provisional patent application Ser. No. 62/078,766, filed Nov. 12, 2014, each of which is incorporated herein by reference in its entirety.

STATEMENT REGARDING FEDERALLY SPONSORED RESEARCH OR DEVELOPMENT

This invention was made with government support under W911NF-12-1-0420 awarded by the U.S. Army/Army Research Office, and GM062357 awarded by the National Institutes of Health. The Government has certain rights in the invention.

FIELD

Provided herein is technology relating to detecting and identifying nucleic acids and particularly, but not exclusively, to compositions, methods, kits, and systems for detecting, identifying, and quantifying target nucleic acids with high confidence at single-molecule resolution.

BACKGROUND

Early detection is critical to the effective treatment of many diseases, especially cancer. Research related to identifying detectable biomarkers associated with early-stage disease has indicated that nucleic acids (e.g., DNA, RNA (e.g., microRNA, mRNA, ncRNA)) provide highly specific biomarkers of cancer and other maladies. In particular, microRNAs (miRNAs) are often dysregulated in disease (see, e.g., Schwarzenbach et al (2011) "Cell-free nucleic acids as biomarkers in cancer patients" Nat. Rev. Cancer 11: 426-437; Iorio & Croce (2012) "MicroRNA dysregulation in cancer: diagnostics, monitoring and therapeutics. A comprehensive review" EMBO Mol. Med. 4: 143-159). Further, miRNAs can be detected in several body fluids, including blood (Mitchell et al (2008) "Circulating microRNAs as stable blood-based markers for cancer detection" Proc. Natl. Acad. Sci. 105: 10513-10518), saliva, urine, and sputum (Iorio, supra). Thus, miRNAs provide an accessible biomarker useful for early diagnosis and treatment of diseases such as cancer.

However, despite their promise as diagnostic biomarkers, the sensitive and specific detection of miRNAs has proven challenging. For example, the low abundance of diagnostic miRNAs in a milieu of other nucleic acids hinders the reliable detection of the relevant diagnostic miRNAs. Existing assays based on polymerase chain reaction (PCR), while highly sensitive, require extraction and amplification steps that are associated with several hours of time to execute. Further, many methods based on nucleic acid amplification are known to introduce bias into results (e.g., amplification products do not accurately reflect the sequence, composition, and quantity of input samples). Other extant methods for amplification-free detection of nucleic acid targets typically utilize thermodynamic discrimination by a nucleic acid probe that hybridizes to a complementary sequence within the target (see, e.g., Tan et al (2004) "Molecular beacons" Curr. Opin. Chem. Biol. 8: 547-553; Sui et al (2011) "An ultra-sensitive DNA assay based on single-molecule detection coupled with hybridization accumulation and its application" The Analyst 136: 3950; Ostergaard & Hrdlicka (2011) "Pyrene-functionalized oligonucleotides and locked nucleic acids (LNAs): Tools for fundamental research, diagnostics, and nanotechnology" Chem Soc Rev 40: 5771-5788; Trcek et al (2012) "Single-mRNA counting using fluorescent in situ hybridization in budding yeast" Nat. Protoc. 7: 408-419; Zhang et al (2012) "Optimizing the specificity of nucleic acid hybridization" Nat. Chem. 4: 208-214). However, these existing methods face two main difficulties. First, in the absence of amplification, high-sensitivity detection generally requires single-molecule measurements that are frequently hampered by matrix-dependent background signals resulting in an incomplete discrimination of target sequences above background (see, e.g., Gunnarsson et al (2008) "Single-Molecule Detection and Mismatch Discrimination of Unlabeled DNA Targets" Nano Lett. 8: 183-188; Chan et al (2010) "Direct Quantification of Single-Molecules of MicroRNA by Total Internal Reflection Fluorescence Microscopy" Anal. Chem. 82: 6911-6918). Second, essentially all existing methods rely on thermodynamic discrimination, which places fundamental physical limits on the specificity of detection and thus results in the incomplete discrimination of target molecules relative to spurious non-target molecules (Zhang, supra). Thus, a sensitive and specific assay for the amplification-free detection of miRNAs in minimally treated native biofluids is needed to provide a rapid and reliable identification and/or quantification of miRNA biomarkers.

SUMMARY

Accordingly, provided herein is technology related to the amplification-free single-molecule detection of unlabeled nucleic acids (e.g., DNA, RNA (e.g., mRNA, miRNA, ncRNA)) that does not rely on thermodynamic discrimination for specificity. In some embodiments, the technology exploits the transient binding of a short detectably labeled (e.g., fluorescent) query probe (e.g., a nucleic acid (e.g., DNA or RNA) query probe) to nucleic acid (e.g., DNA, RNA (e.g., mRNA, miRNA, ncRNA)) targets that have been immobilized on a solid surface by hybridization to a capture probe (e.g., a nucleic acid capture probe, e.g., comprising a modified base such as in a locked nucleic acid (LNA oligonucleotide) capture probe). The repeated binding of multiple copies of the detectably labeled (e.g., fluorescent) query probe to the same immobilized target nucleic acid increases the confidence of the measurement. The binding of the query probes is a Poisson process and thus the discrimination factor compared to background or detection of spurious targets increases exponentially with increasing acquisition time. Consequently, the technology provides discrimination of multiple closely related targets in a sample with minimal, e.g., effectively or virtually zero, background signal. Experiments conducted during the development of the technology indicate that the approach is generally applicable (e.g., to detect DNA, RNA (e.g., microRNA, mRNA). In particular, embodiments of the technology identified and quantified five different miRNAs (from organisms such as *Homo sapiens* and *Caenorhabditis elegans*) present at sub-picomolar concentrations in buffer solutions and in complex biological matrices. Additional embodiments of the technology identified and quantified changes in the structure of a mRNA that were induced by the binding of a ligand to the mRNA. In some embodiments, the technology quantified the concentration of ligand in the assay mixtures, e.g., in some embodiments the technology quantified the ligand bound to a nucleic acid and/or quantified the ligand that was not bound (e.g., free in solution) to the nucleic acid.

Further, embodiments provided for high-confidence detection of nucleic acid binding partners at the single molecule level (e.g., detecting binding of a ligand to a nucleic acid, quantifying the concentration of a nucleic acid that binds a ligand, quantifying the concentration of a nucleic acid that does not bind a ligand, quantifying ligand in a bound state, and/or quantifying a ligand in an unbound state). In some embodiments, nucleic acid molecules bind ligands (e.g., metabolites, sugars, enzyme cofactors, proteins, and other nucleic acids) that are biomarkers. The nucleic acid responds to ligand binding, e.g., by changing shape (e.g., conformation, structure, etc.) or becomes (e.g., partially) covered in a way that changes the accessibility of a segment, e.g., to a ligand and/or a probe. Thus, in some embodiments the technology provides a platform for the specific and ultrasensitive detection of virtually any biomarker of interest through detecting changes (e.g., in accessibility, conformation, structure, etc.) in single target nucleic acid molecules. In some embodiments, this approach involves immobilizing an unlabeled nucleic acid (e.g., by a capture probe) onto a glass or fused silica surface, followed by observation of the repeated, transient binding of a query probe (e.g., a short fluorescently labeled DNA probe) to that segment of the captured nucleic acid that changes accessibility upon biomarker binding. The disclosed technology uses the unique kinetic "fingerprint" discussed herein and its modulation by biomarker capture to reach arbitrarily high discrimination against background signal with increased sampling time, essentially eliminating false positive signals. This platform is applicable without any need for biomarker amplification, utilizes no enzymes, and thus requires minimal pre-treatment of biological samples prior to biomarker detection and avoids or minimizes the introduction of sampling bias.

Accordingly, embodiments of the technology provide a detection complex for detecting a nucleic acid or a portion of a nucleic acid. In particular, some embodiments provide a complex for detecting a target nucleic acid comprising a first region and a second region; a capture probe (e.g., a nucleic acid capture probe) comprising a target binding region hybridized to the first region of the nucleic acid to form a thermodynamically stable duplex; and a detectably labeled (e.g., fluorescent) query probe that hybridizes to the second region of the target nucleic acid with a kinetic constant $k_{off}$ that is greater than 0.1 $min^{-1}$ and/or a kinetic rate constant $k_{on}$ that is greater than 0.1 $min^{-1}$. For example, in some embodiments, the kinetic rate constant $k_{off}$ is greater than 1 $min^{-1}$ and/or the kinetic rate constant $k_{on}$ is greater than 1 $min^{-1}$. In some embodiments, the kinetic rate constant $k_{on}$ describing the association of the query probe with the query region of the nucleic acid to form a hybrid and/or the kinetic rate constant $k_{off}$ describing the dissociation of the hybrid is/are greater than 0.1 $min^{-1}$, e.g., greater than 1 $min^{-1}$ (e.g., greater that approximately 0.002 $s^{-1}$, greater than approximately 0.02 $s^{-1}$). In some embodiments, the kinetic rate constant $k_{on}$ describing the association of the query probe with the query region of the nucleic acid to form a hybrid and/or the kinetic rate constant $k_{off}$ describing the dissociation of the hybrid is/are greater than 0.001 $s^{-1}$, e.g., greater than 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, or 8 $s^{-1}$.

Further, in some embodiments, the detectably labeled (e.g., fluorescent) query probe hybridizes to the target nucleic acid with a standard free energy that is greater than −12 kcal/mol at approximately 37° C., e.g., the fluorescent query probe hybridizes to the target nucleic acid with a standard free energy that is greater than −10 kcal/mol at approximately 37° C. In terms of melting temperatures, some embodiments comprise use of a fluorescent query probe that hybridizes to the target nucleic acid with a melting temperature of less than 35° C. to less than 40° C.

The technology contemplates various modifications of nucleic acid capture probes, e.g., to modify (e.g., strengthen) the hybridization of the capture probe and the target nucleic acid. For example, in some embodiments, the nucleic acid capture probe comprises a locked nucleic acid.

Particular aspects of the technology relate to the sizes of the capture probe, query probe, and nucleic acid (e.g., the target nucleic acid). For instance, in some embodiments, the first region of the nucleic acid consists of from 5 to 500 nucleotides. In some embodiments, the target binding region of the nucleic acid capture probe consists of from 5 to 500 nucleotides; in some embodiments, the first region of the target nucleic acid consists of 5 to 15 nucleotides; in some embodiments, the target binding region consists of 5 to 15 nucleotides; in some embodiments, the first region of the target nucleic acid consists of 6 to 12 nucleotides; in some embodiments, the target binding region consists of 6 to 12 nucleotides; in some embodiments, the first region of the target nucleic acid consists of 8 to 10 nucleotides; in some embodiments, the target binding region consists of 8 to 10 nucleotides; in some embodiments, the second region of the target nucleic acid consists of 5 to 15 nucleotides; in some embodiments, the fluorescent query probe consists of 5 to 15 nucleotides; in some embodiments, the second region of the target nucleic acid consists of 6 to 12 nucleotides; in some embodiments, the fluorescent query probe consists of 6 to 12 nucleotides; in some embodiments, the second region of the target nucleic acid consists of 8 to 10 nucleotides; and in some embodiments, the fluorescent query probe consists of 8 to 10 nucleotides.

Embodiments of the technology relate to the use of a solid support, e.g., comprising one or more capture probes. Accordingly, in some embodiments the complex described above further comprises a solid support. In some embodiments, the solid support comprises an array of capture probes. Embodiments provide various technologies for immobilizing the capture probe to the solid support. For example, some embodiments provide that the capture probe (e.g., a nucleic acid capture probe) comprises an immobilization moiety, e.g., in some embodiments, the nucleic acid capture probe is bound to a solid support by an immobilization moiety. Particular embodiments provide that the capture probe (e.g., a nucleic acid capture probe) comprises a biotin moiety and/or some embodiments provide a complex comprising a solid support comprising a streptavidin moiety.

The technology is related in some embodiments to fluorescent detection of a detectably labeled (e.g., fluorescent) query probe. For instance, in some embodiments, the detectably labeled (e.g., fluorescent) query probe comprises a fluorescent label (e.g., fluorescein, 6-carboxyfluorescein (6-FAM dye), 5-carboxyfluorescein (5-FAM dye), 5- or 6-carboxy-4, 7, 2', 7'-tetrachlorofluorescein (TET dye), 5- or 6-carboxy-4'5'2'4'5'7' hexachlorofluorescein (HEX dye), 5' or 6'-carboxy-4',5'-dichloro-2,'7'-dimethoxyfluorescein (JOE dye), 5-carboxy-2',4',5',7'-tetrachlorofluorescein (ZOE dye), rhodol, rhodamine, tetramethylrhodamine (TAMRA dye), 4,7-dlchlorotetramethyl rhodamine (DTAMRA dye), rhodamine X (ROX dye), TEXAS RED dye, CY3 dye, CY3.5 dye, CY5 dye, CY5.5 dye, CY7 dye, or CY7.5 dye, CY3B dye, ALEXA FLUOR 350 dye, ALEXA FLUOR 405 dye, ALEXA FLUOR 488, ALEXA FLUOR 546 dye, ALEXA FLUOR 555 dye, ALEXA FLUOR 568 dye, ALEXA FLUOR 594 dye, ALEXA FLUOR 633 dye, ALEXA FLUOR 647 dye, ALEXA FLUOR 680 dye, ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, or ATTO740).

In some embodiments, the fluorescent label comprises a dye that is CY3B dye, ALEXA FLUOR 405 dye, ALEXA FLUOR 555 dye, ALEXA FLUOR 633 dye, ALEXA FLUOR 647 dye, ATTO 565, ATTO 647, and ATTO 647N.

In some embodiments the target nucleic acid is a deoxyribonucleic acid (DNA) or a ribonucleic acid (RNA), e.g., a target nucleic acid consisting of less than 50 nucleotides, e.g., a target nucleic acid consisting of less than 25 nucleotides. In particular embodiments, the technology is related to a complex wherein the target nucleic acid is a mRNA or a microRNA. In embodiments, the target nucleic acid is a biomarker for a disease, e.g., a cancer.

Additional embodiments provide methods for detecting a nucleic acid. For example, in some embodiments, the technology is related to a method for detecting a target nucleic acid in a sample comprising immobilizing a target nucleic acid to a discrete region of a solid support, said target nucleic acid comprising a first region and a second region and said discrete region of said solid support comprising a capture probe (e.g., a nucleic acid capture probe) comprising a target binding region; adding a detectably labeled (e.g., fluorescent) query probe that hybridizes to the second region of the target nucleic acid with a kinetic rate constant $k_{off}$ that is greater than 0.1 $min^{-1}$ (e.g., greater than 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, or 8 $s^{-1}$) and/or a kinetic rate constant $k_{on}$ that is greater than 0.1 $min^{-1}$ (e.g., greater than 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, or 8 $s^{-1}$); and identifying the sample as comprising the target nucleic acid when the dwell time of the query probe in the discrete region of the solid support is greater than the dwell time of the query probe in the absence of the target nucleic acid; the fluorescence intensity of the query probe in the discrete region is greater than a fluorescence intensity detected in the absence of the target nucleic acid; and/or the number of binding events in the discrete region is greater than the number of binding events detected in the absence of the target nucleic acid. In some embodiments of the method, the kinetic rate constant $k_{off}$ is greater than 1 $min^{-1}$ (e.g., greater than 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, or 8 $s^{-1}$) and/or the kinetic rate constant $k_{on}$ is greater than 1 $min^{-1}$ (e.g., greater than 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, or 8 $s^{-1}$).

In some embodiments of the methods provided, the detectably labeled (e.g., fluorescent) query probe hybridizes to the target nucleic acid with a standard free energy that is greater than −12 kcal/mol at approximately 37° C., e.g., the fluorescent query probe hybridizes to the target nucleic acid with a standard free energy that is greater than −12 kcal/mol at approximately 37° C. In some embodiments of the methods, the fluorescent query probe hybridizes to the target nucleic acid with a melting temperature of less than 35° C. to less than 40° C. The methods provide in some embodiments that the nucleic acid capture probe comprises a modified base, e.g., comprises a locked nucleic acid.

In some embodiments of the methods, the first region of the target nucleic acid consists of 5 to 500 nucleotides; in some embodiments, the target binding region of the nucleic acid capture probe consists of from 5 to 500 nucleotides; in some embodiments, the first region of the target nucleic acid consists of 5 to 15 nucleotides; in some embodiments, the target binding region consists of 5 to 15 nucleotides; in some embodiments, the first region of the target nucleic acid consists of 6 to 12 nucleotides. In some embodiments, the target binding region consists of 6 to 12 nucleotides; in some embodiments, the first region of the target nucleic acid consists of 8 to 10 nucleotides; in some embodiments, the target binding region consists of 8 to 10 nucleotides; in some embodiments, the second region of the target nucleic acid consists of 5 to 15 nucleotides; in some embodiments, the fluorescent query probe consists of 5 to 15 nucleotides. In some embodiments, the second region of the target nucleic acid consists of 6 to 12 nucleotides; in some embodiments, the fluorescent query probe consists of 6 to 12 nucleotides; in some embodiments, the second region of the target nucleic acid consists of 8 to 10 nucleotides; in some embodiments, the fluorescent query probe consists of 8 to 10 nucleotides.

The technology provides methods related to solid supports and arrays. Accordingly, in some embodiments, the capture probe (e.g., the nucleic acid capture probe) comprises an immobilization moiety and in some embodiments the nucleic acid capture probe is bound to the solid support by an immobilization moiety. In exemplary embodiments, the capture probe (e.g., the nucleic acid capture probe) comprises a biotin moiety and/or the solid support comprises a streptavidin moiety.

Some embodiments of methods provide that the detectably labeled (e.g., fluorescent) query probe comprises a fluorescent label (e.g., fluorescein, 6-carboxyfluorescein (6-FAM dye), 5-carboxyfluorescein (5-FAM dye), 5- or 6-carboxy-4, 7, 2', 7'-tetrachlorofluorescein (TET dye), 5- or 6-carboxy-4'5'2'4'5'7' hexachlorofluorescein (HEX dye), 5' or 6'-carboxy-4',5'-dichloro-2,'7'-dimethoxyfluorescein (JOE dye), 5-carboxy-2',4',5',7'-tetrachlorofluorescein (ZOE dye), rhodol, rhodamine, tetramethylrhodamine (TAMRA dye), 4,7-dlchlorotetramethyl rhodamine (DTAMRA dye), rhodamine X (ROX dye), TEXAS RED dye, CY3 dye, CY3.5 dye, CY5 dye, CY5.5 dye, CY7 dye, or CY7.5 dye, CY3B dye, ALEXA FLUOR 350 dye, ALEXA FLUOR 405 dye, ALEXA FLUOR 488 dye, ALEXA FLUOR 546 dye, ALEXA FLUOR 555 dye, ALEXA FLUOR 568 dye, ALEXA FLUOR 594 dye, ALEXA FLUOR 633 dye, ALEXA FLUOR 647 dye, ALEXA FLUOR 680 dye, ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, or ATTO740).

In some embodiments, the fluorescent label comprises a dye that is CY3B dye, ALEXA FLUOR 405 dye, ALEXA FLUOR 555 dye, ALEXA FLUOR 633 dye, ALEXA FLUOR 647 dye, ATTO 565, ATTO 647, and ATTO 647N.

Some embodiments provide a method for the detection of a target nucleic acid that is a ribonucleic acid, e.g., a miRNA (e.g., a miRNA selected from Table 1). Some embodiments provide a method for detecting a target nucleic acid consisting of less than 50 nucleotides, e.g., a target nucleic acid consisting of less than 25 nucleotides. Some embodiments relate to detecting a disease, e.g., in some embodiments, the target nucleic acid is a biomarker for a disease such as, e.g., a cancer.

Some embodiments provide a method for the detection of a change in the conformation or accessibility of a nucleic acid. Some embodiments provide a method for the detection of binding of a ligand to a nucleic acid (e.g., a DNA, an RNA (e.g., a mRNA)). For example, in some embodiments the binding of a ligand to a nucleic acid causes a change in the conformation of the nucleic acid. Embodiments provide that a change in the conformation of a nucleic acid is detectable by a change in the kinetics of binding of a query probe to the target nucleic acid. Embodiments provide technology for quantifying the concentration of a ligand in an assay, e.g., in some embodiments the technology finds use in quantifying the bound and/or unbound ligand (e.g., bound to a nucleic acid and/or not bound to a nucleic acid) in an assay mixture.

Further embodiments relate to kits for detecting a nucleic acid. For example, in some embodiments, the technology provides a kit comprising a solid support comprising an immobilized capture probe and a detectably labeled (e.g., fluorescent) query probe consisting of 5 to 15 nucleotides, e.g., consisting of 6 to 12 nucleotides. In some embodiments, the kit comprises a solid support that is, e.g., a microscope slide, a bead, a coverslip, a biotin-conjugated microscope slide or coverslip, or a solid support comprising a zero mode waveguide array. Embodiments of kits comprise one or more positive controls and/or one or more negative controls (e.g., controls having known concentrations including, in some embodiments, a negative control with nominally a zero concentration).

In some embodiments, the kit comprises a capture probe that is complementary to a first region of a target nucleic acid (e.g., a DNA, an RNA (e.g., a miRNA, a mRNA, a ncRNA) and the query probe is complementary to a second region of a target nucleic acid (e.g., a DNA, an RNA (e.g., a miRNA, a mRNA, a ncRNA).

Additional embodiments provide a system for the detection of a nucleic acid. In some embodiments, the system comprises a solid support comprising an immobilized capture probe, a detectably labeled (e.g., fluorescent) query probe consisting of 5 to 15 nucleotides, and a detector (e.g., a fluorescence detector (e.g., a fluorescence microscope)). In some embodiments of systems, the fluorescence microscope comprises an illumination configuration to excite bound query probes. In some embodiments the fluorescence detector is a fluorescence microscope comprising an illumination configuration that is a prism-type total internal reflection fluorescence (TIRF) microscope, an objective-type TIRF microscope, a near-TIRF or HiLo microscope, a confocal laser scanning microscope, a zero-mode waveguide, and/or an illumination configuration capable of parallel monitoring of a large area of the slide or coverslip (>100 μm$^2$) while restricting illumination to a small region of space near the surface.

Further embodiments of systems comprise a detector (e.g., a fluorescence detector) comprising an intensified charge coupled device (ICCD), an electron-multiplying charge coupled device (EM-CCD), a complementary metal-oxide-semiconductor (CMOS), a photomultiplier tube (PMT), an avalanche photodiode (APD), and/or another detector capable of detecting fluorescence emission from single chromophores. Embodiments of systems comprise a computer and software encoding instructions for the computer to perform, e.g., instructions comprising the steps of a method for data processing and interpretation, instructions comprising the steps of a method for distinguishing a sample comprising a target nucleic acid from a non-target nucleic acid, and/or instructions comprising the steps for determining the concentration of a target nucleic acid in a sample.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 1A shows an embodiment comprising a capture probe attached or fixed to a solid support, e.g., the capture probe comprises a moiety that provides for the immobilization of the capture probe to a solid support by interaction of the moiety with a second moiety attached to the solid support. FIG. 1B shows an exemplary embodiment comprising a nucleic acid (e.g., a target nucleic acid) that is to be detected, identified, quantified, and/or characterized; a capture probe (e.g., a nucleic acid capture probe); and a detectably labeled (e.g., fluorescent) query probe. In some embodiments, one or more nucleotides of the capture probe comprise a modified nucleotide (e.g., a locked nucleic acid (LNA nucleotide)) (see, e.g., underlined nucleotides in exemplary capture probe sequence).

FIG. 3A shows data from an experiment using a fully complementary fluorescent probe to detect let-7a.

FIG. 5A shows the detection of *H. sapiens* hsa-let-7a. FIG. 5B shows the detection of *H. sapiens* hsa-miR-16. FIG. 5C shows the detection of *H. sapiens* hsa-miR-21. FIG. 5D shows the detection of *C. elegans* cel-miR-39.

FIG. 6 is a series of plots showing the effect of ligand (e.g., preQ$_1$) binding on the binding kinetics of a probe.

FIG. 7 is a series of plots showing the detection of changes in nucleic acid conformation using spike train analysis. FIG. 7A is a cumulative histogram displaying the interspike interval time inside and outside bursts. FIG. 7B shows the trajectory and the corresponding histogram in the absence of ligand that represents nucleic acids in multiple conformational states.

FIG. 8 is a series of plots showing ligand-dependent changes in bursting behavior of nucleic acids (e.g., comprising a riboswitche).

Figures 1A, 1B:
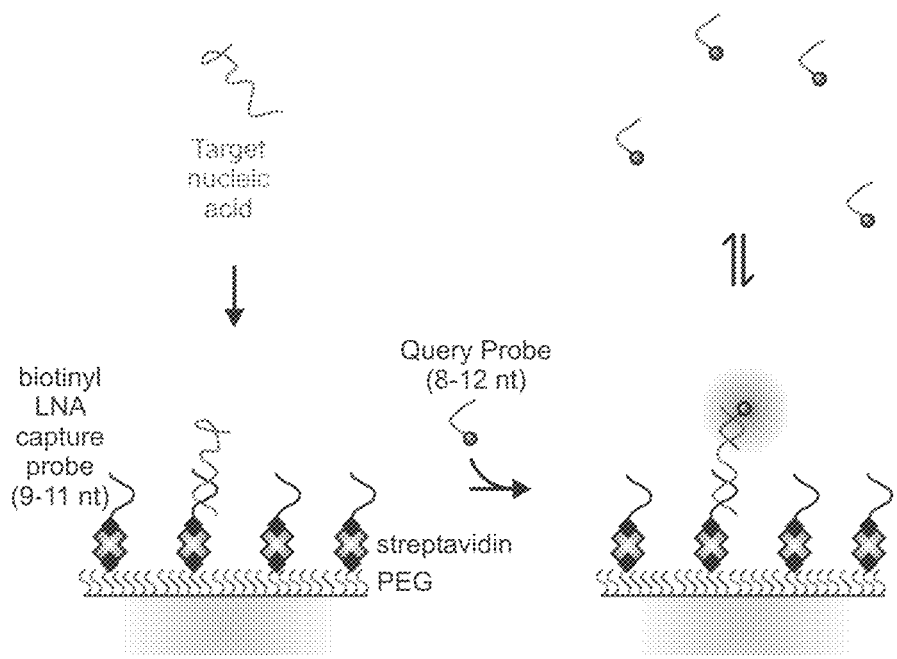
FIG. 1A and FIG. 1B are schematic drawings showing an exemplary embodiment of the technology as described herein.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Moreover, it should be appreciated that the drawings are not intended to limit the scope of the present teachings in any way.

DETAILED DESCRIPTION

Provided herein is technology related to single-molecule detection of nucleic acids (e.g., DNA, RNA (e.g., miRNA, mRNA, ncRNA)). In some embodiments, the technology is related to the detection of small nucleic acids (e.g., comprising less than 100 bases or base pairs, e.g., comprising less than 90, 80, 70, 60, 50, 45, 40, 39, 38, 37, 36, 35, 34, 33, 32, 31, 30, 29, 28, 27, 26, 25, 24, 23, 22, 21, 20, 19, 18, 17, 16, 15, or fewer than 15 bases or base pairs). In particular, embodiments of the technology provide a technique for the amplification-free, specific, and sensitive counting of single nucleic acid molecules (e.g., DNA, RNA (e.g., miRNA, mRNA, ncRNA)) in complex mixtures. The technology exploits the repeated, transient binding of short query probes (e.g., detectably labeled (e.g., fluorescently labeled) query probes) to an immobilized target nucleic acid to produce a time-resolved signal based on the kinetics of the query probe binding to and dissociating from the target nucleic acid. Binding events occur as a Poisson equilibrium sampling process; thus, in some embodiments, Poisson statistical treatment of the data is used to discriminate target nucleic acids from non-target nucleic acids.

During the development of embodiments of the technology provided herein, experiments were conducted in which the transient binding of query probes to immobilized targets nucleic acids was monitored using total internal reflection fluorescence (TIRF) microscopy. The data collected from experiments using five different miRNAs indicated that the technology provides a general technique for the high-confidence single-molecule detection of nucleic acids, in particular small nucleic acids such as miRNAs. Further, the technology provides a significantly improved discrimination of target nucleic acids over background relative to extant technologies based on thermodynamic probing. Further, closely related targets (e.g., differing at a single nucleotide) are discriminated by adjusting the time of observation, which effectively eliminated false positive signals.

In particular experiments, data collected indicated that the technology provides greater than a 50-fold discrimination between two members of the let-7 miRNA family that differ by a single-nucleotide polymorphism, let-7a and let-7c. Further, experiments demonstrated the specific detection of let-7a in both whole-cell lysate and in a total RNA extract produced from human cancer cells. The technology is not only applicable to detecting miRNA, but also finds broad application in the sensitive, high-confidence detection of specific nucleic acid biomarkers in both research and clinical settings.

Further, during the development of embodiments of the technology provided herein, experiments were conducted in which the technology was used to quantify conformational (e.g., structural) states of a nucleic acid (e.g., a mRNA), the effects of ligand binding to the mRNA on the conformational (e.g., structural) states of a nucleic acid, and the concentrations of ligand in the solution in the bound and/or unbound states. In particular, data were collected relating to the ligand-dependent structure and accessibility of a Shine-Dalgarno sequence of an mRNA comprising a ligand-binding riboswitch (e.g., a riboswitch that binds 7-aminomethyl-7-deazaguanine (preQ1)). The data indicated that decreases in both the probe binding and the probe dissociation rate constants were due to complex changes in nucleic acid sequence accessibility in single nucleic acid (e.g., mRNA) molecules. Spike train analysis indicated that individual nucleic acids (e.g., mRNAs) dynamically interconvert between multiple (e.g., at least two) conformational states, one manifesting as sudden bursts of probe binding and the other as infrequent but still detectable probe binding events.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages, are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, a "nucleic acid" or a "nucleic acid sequence" refers to a polymer or oligomer of pyrimidine and/or purine bases, preferably cytosine, thymine, and uracil, and adenine and guanine, respectively (See Albert L. Lehninger, Principles of Biochemistry, at 793-800 (Worth Pub. 1982)). The present technology contemplates any deoxyribonucleotide, ribonucleotide, or peptide nucleic acid component, and any chemical variants thereof, such as methylated, hydroxymethylated, or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. In some embodiments, a nucleic acid or nucleic acid sequence comprises other kinds of nucleic acid structures such as, for instance, a DNA/RNA helix, peptide nucleic acid (PNA), morpholino, locked nucleic acid (LNA nucleotide), and/or a ribozyme. Hence, the term "nucleic acid" or "nucleic acid sequence" may also encompass a chain comprising non-natural nucleotides, modified nucleotides, and/or non-nucleotide building blocks that can exhibit the same function as natural nucleotides (e.g., "nucleotide analogues"); further, the term "nucleic acid sequence" as used herein refers to an oligonucleotide, nucleotide or polynucleotide, and fragments or portions thereof, and to DNA or RNA of genomic or synthetic origin, which may be single or double stranded, and represent the sense or antisense strand.

The term "nucleotide analogue" as used herein refers to modified or non-naturally occurring nucleotides including but not limited to analogues that have altered stacking interactions such as 7-deaza purines (i.e., 7-deaza-dATP and 7-deaza-dGTP); base analogues with alternative hydrogen bonding configurations (e.g., such as Iso-C and Iso-G and other non-standard base pairs described in U.S. Pat. No. 6,001,983 to S. Benner and herein incorporated by reference); non-hydrogen bonding analogues (e.g., non-polar, aromatic nucleoside analogues such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872; each of which is herein incorporated by reference); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152).

Nucleotide analogues include nucleotides having modification on the sugar moiety, such as dideoxy nucleotides and 2'-O-methyl nucleotides. Nucleotide analogues include modified forms of deoxyribonucleotides as well as ribonucleotides.

"Peptide nucleic acid" means a DNA mimic that incorporates a peptide-like polyamide backbone.

As used herein, the term "% sequence identity" refers to the percentage of nucleotides or nucleotide analogues in a nucleic acid sequence that is identical with the corresponding nucleotides in a reference sequence after aligning the two sequences and introducing gaps, if necessary, to achieve the maximum percent identity. Hence, in case a nucleic acid according to the technology is longer than a reference sequence, additional nucleotides in the nucleic acid, that do not align with the reference sequence, are not taken into account for determining sequence identity. Methods and computer programs for alignment are well known in the art, including blastn, Align 2, and FASTA.

The term "homology" and "homologous" refers to a degree of identity. There may be partial homology or complete homology. A partially homologous sequence is one that is less than 100% identical to another sequence.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

As used herein, the terms "complementary" or "complementarity" are used in reference to polynucleotides (e.g., a sequence of nucleotides such as an oligonucleotide or a target nucleic acid) related by the base-pairing rules. For example, for the sequence "5'-A-G-T-3'" is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

In some contexts, the term "complementarity" and related terms (e.g., "complementary", "complement") refers to the nucleotides of a nucleic acid sequence that can bind to another nucleic acid sequence through hydrogen bonds, e.g., nucleotides that are capable of base pairing, e.g., by Watson-Crick base pairing or other base pairing. Nucleotides that can form base pairs, e.g., that are complementary to one another, are the pairs: cytosine and guanine, thymine and adenine, adenine and uracil, and guanine and uracil. The percentage complementarity need not be calculated over the entire length of a nucleic acid sequence. The percentage of complementarity may be limited to a specific region of which the nucleic acid sequences that are base-paired, e.g., starting from a first base-paired nucleotide and ending at a last base-paired nucleotide. The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Thus, in some embodiments, "complementary" refers to a first nucleobase sequence that is at least 60%, 65%, 70%, 75%, 80%, 85%, 90%, 95%, 97%, 98%, or 99% identical to the complement of a second nucleobase sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more nucleobases, or that the two sequences hybridize under stringent hybridization conditions. "Fully complementary" means each nucleobase of a first nucleic acid is capable of pairing with each nucleobase at a corresponding position in a second nucleic acid. For example, in certain embodiments, an oligonucleotide wherein each nucleobase has complementarity to a nucleic acid has a nucleobase sequence that is identical to the complement of the nucleic acid over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more nucleobases.

"Mismatch" means a nucleobase of a first nucleic acid that is not capable of pairing with a nucleobase at a corresponding position of a second nucleic acid.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41*(\% \text{ G+C})$, when a nucleic acid is in aqueous solution at 1 M NaCl (see e.g., Anderson and Young, Quantitative Filter Hybridization, in Nucleic Acid Hybridization (1985). Other references (e.g., Allawi and SantaLucia, Biochemistry 36: 10581-94 (1997) include more sophisticated computations which account for structural, environmental, and sequence characteristics to calculate $T_m$. For example, in some embodiments these computations provide an improved estimate of $T_m$ for short nucleic acid probes and targets (e.g., as used in the examples).

As used herein, a "non-coding RNA" or "ncRNA" is a functional RNA molecule that is not translated into a protein. Less-frequently used synonyms are non-protein-coding RNA (npcRNA), non-messenger RNA (nmRNA), small non-messenger RNA (snmRNA), and functional RNA (fRNA). The term small RNA (sRNA) is often used for bacterial ncRNAs. The DNA sequence from which a non-coding RNA is transcribed as the end product is often called an RNA gene or a non-coding RNA gene. Non-coding RNA genes include highly abundant and functionally important RNAs such as transfer RNA (tRNA) and ribosomal RNA (rRNA), as well as RNAs such as snoRNAs, microRNAs, siRNAs, and piRNAs. The number of ncRNAs encoded within the human genome is unknown, however recent transcriptomic and bioinformatic studies suggest the existence of thousands of ncRNAs. Since most of the newly identified ncRNAs have not been validated for their function, it is possible that many are non-functional.

As used herein, the term "miRNA" refers to micro RNA. As used herein, the term "miRNA target sequence" refers to a miRNA that is to be detected (e.g., in the presence of other nucleic acids). In some embodiments, a miRNA target sequence is a variant of a miRNA.

The term "siRNAs" refers to short interfering RNAs. In some embodiments, siRNAs comprise a duplex, or double-stranded region, where each strand of the double-stranded region is about 18 to 25 nucleotides long; the double-stranded region can be as short as 16, and as long as 29, base pairs long, where the length is determined by the antisense strand. Often siRNAs contain from about two to four unpaired nucleotides at the 3' end of each strand. SiRNAs appear to function as key intermediates in triggering RNA interference in invertebrates and in vertebrates, and in triggering sequence-specific RNA degradation during posttranscriptional gene silencing in plants. At least one strand of the duplex or double-stranded region of a siRNA is substantially homologous to or substantially complementary to a target RNA molecule. The strand complementary to a target RNA molecule is the "antisense" strand; the strand homologous to the target RNA molecule is the "sense" strand and is also complementary to the siRNA antisense strand. One strand of the double stranded region need not be the exact length of the opposite strand' thus, one strand may have at least one fewer nucleotides than the opposite complementary strand, resulting in a "bubble" or at least one unmatched base in the opposite strand. One strand of the double-stranded region need not be exactly complementary to the opposite strand; thus, the strand, preferably the sense strand, may have at least one mismatched base pair.

siRNAs may also contain additional sequences; non-limiting examples of such sequences include linking sequences, or loops, which connect the two strands of the duplex region. This form of siRNAs may be referred to "si-like RNA", "short hairpin siRNA" where the short refers to the duplex region of the siRNA, or "hairpin siRNA". Additional non-limiting examples of additional sequences present in siRNAs include stem and other folded structures. The additional sequences may or may not have known functions; non-limiting examples of such functions include increasing stability of an siRNA molecule, or providing a cellular destination signal.

"Pre-miRNA" or "pre-miR" means a non-coding RNA having a hairpin structure, which is the product of cleavage of a pri-miR by the double-stranded RNA-specific ribonuclease known as Drosha.

"Stem-loop sequence" means an RNA having a hairpin structure and containing a mature miRNA sequence. PremiRNA sequences and stem-loop sequences may overlap. Examples of stem-loop sequences are found in the miRNA database known as miRBase (available at the worldwide web at microrna.sanger.ac.uk).

"Pri-miRNA" or "pri-miR" means a non-coding RNA having a hairpin structure that is a substrate for the double-stranded RNA-specific ribonuclease Drosha. "miRNA precursor" means a transcript that originates from a genomic DNA and that comprises a non-coding, structured RNA comprising one or more miRNA sequences. For example, in certain embodiments a miRNA precursor is a pre-miRNA. In certain embodiments, a miRNA precursor is a pri-miRNA.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified," "mutant," or "polymorphic" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprising two or more deoxyribonucleotides or ribonucleotides, preferably at least 5 nucleotides, more preferably at least about 10 to 15 nucleotides and more preferably at least about 15 to 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

As used herein, the terms "subject" and "patient" refer to any organisms including plants, microorganisms, and animals (e.g., mammals such as dogs, cats, livestock, and humans).

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

As used herein, a "biological sample" refers to a sample of biological tissue or fluid. For instance, a biological sample may be a sample obtained from an animal (including a human); a fluid, solid, or tissue sample; as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagomorphs, rodents, etc. Examples of biological samples include sections of tissues, blood, blood fractions, plasma, serum, urine, or samples from other peripheral sources or cell cultures, cell colonies, single cells, or a collection of single cells. Furthermore, a biological sample includes pools or mixtures of the above mentioned samples. A biological sample may be provided by removing a sample of cells from a subject, but can also be provided by using a previously isolated sample. For example, a tissue sample can be removed from a subject suspected of having a disease by conventional biopsy techniques. In some embodiments, a blood sample is taken from a subject. A biological sample from a patient means a sample from a subject suspected to be affected by a disease.

Environmental samples include environmental material such as surface matter, soil, water, and industrial samples, as well as samples obtained from food and dairy processing instruments, apparatus, equipment, utensils, disposable and non-disposable items. These examples are not to be construed as limiting the sample types applicable to the present invention.

The term "label" as used herein refers to any atom or molecule that can be used to provide a detectable (preferably quantifiable) effect, and that can be attached to a nucleic acid or protein. Labels include, but are not limited to, dyes (e.g., fluorescent dyes or moities); radiolabels such as $^{32}P$; binding moieties such as biotin; haptens such as digoxgenin; luminogenic, phosphorescent, or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry; fluorescence polarization), and the like. A label may be a charged moiety (positive or negative charge) or, alternatively, may be charge neutral. Labels can include or consist of nucleic acid or protein sequence, so long as the sequence comprising the label is detectable.

"Support" or "solid support", as used herein, refers to a matrix on or in which nucleic acid molecules, microparticles, and the like may be immobilized, e.g., to which they may be covalently or noncovalently attached or in or on which they may be partially or completely embedded so that they are largely or entirely prevented from diffusing freely or moving with respect to one another.

As used herein, "moiety" refers to one of two or more parts into which something may be divided, such as, for example, the various parts of an oligonucleotide, a molecule, a chemical group, a domain, a probe, etc.

As used herein, a "query probe" is any entity (e.g., molecule, biomolecule, etc.) that recognizes a nucleic acid (e.g., binds to a nucleic acid, e.g., binds specifically to a nucleic acid). In exemplary embodiments, the query probe is a protein that recognizes a nucleic acid (e.g., a nucleic acid binding protein, an antibody, a transcription factor, or any other protein that binds to a particular sequence in a nucleic acid). In some other exemplary embodiments, the query probe is a nucleic acid (e.g., a DNA, an RNA, a nucleic acid comprising DNA and RNA, a nucleic acid comprising modified bases and/or modified linkages between bases; e.g., a nucleic acid as described hereinabove). In some embodiments, the query probe is labeled, e.g., with a detectable label such as, e.g., a fluorescent moiety as described herein. In some embodiments, the query probe comprises more than one type of molecule (e.g., more than one of a protein, a nucleic acid, a chemical linker or a chemical moiety).

As used herein, a "capture probe" is any entity (e.g., molecule, biomolecule, etc.) that recognizes a nucleic acid (e.g., binds to a nucleic acid, e.g., binds specifically to a nucleic acid). In exemplary embodiments, the capture probe is a protein that recognizes a nucleic acid (e.g., a nucleic acid binding protein, an antibody, a transcription factor, or any other protein that binds to a particular sequence in a nucleic acid). In some other exemplary embodiments, the capture probe is a nucleic acid (e.g., a DNA, an RNA, a nucleic acid comprising DNA and RNA, a nucleic acid comprising modified bases and/or modified linkages between bases; e.g., a nucleic acid as described hereinabove). In some embodiments, the capture probe is labeled, e.g., with a detectable label such as, e.g., a fluorescent moiety as described herein. In some embodiments, the capture probe comprises more than one type of molecule (e.g., more than one of a protein, a nucleic acid, a chemical linker or a chemical moiety).

Although the disclosure herein refers to certain illustrated embodiments, it is to be understood that these embodiments are presented by way of example and not by way of limitation.

DESCRIPTION

Provided herein are embodiments of a technique for the specific and ultrasensitive detection of single nucleic acids (e.g., DNA, RNA (e.g., microRNAs (miRNAs), mRNA, ncRNA)). In some embodiments, a labeled nucleic acid is detected, e.g., using an instrument to detect a signal produced by the label. For instance, some embodiments comprise use of a detectably labeled (e.g., fluorescently labeled) query probe and a detector of fluorescence emission such a fluorescent microscopy technique. In some embodiments, the technology finds use as a diagnostic tool for identifying mutant or aberrantly expressed nucleic acid targets in biological samples. In some embodiments, this approach involves the capture of unlabeled nucleic acids (e.g., DNA, RNA (e.g., microRNAs (miRNAs), mRNA, ncRNA)) on a solid support (e.g., glass or fused silica) using a capture probe (e.g., a locked nucleic acid (LNA oligonucleotide)) that specifically binds one segment of the target, followed by observation of the repeated, transient binding of a short detectably labeled (e.g., fluorescently labeled) nucleic acid (e.g., DNA) query probe to a second segment of the target.

Existing techniques for nucleic acid (e.g., DNA, RNA (e.g., microRNAs (miRNAs), mRNA, ncRNA)) detection utilize probes that form a thermodynamically stable complex with the target molecule, and are thus limited to weak and often unreliable thermodynamic discrimination against background signal or spurious targets. In contrast, the technology described herein utilizes probes that repeatedly bind to the target molecule and related methods to record the large number of independent binding events that occur for each observed target molecule. This repeated kinetic sampling provides a unique kinetic "fingerprint" for the target and provides for a highly specific and sensitive detection of nucleic acids, in particular short nucleic acids, e.g., nucleic acids comprising less than 100, less than 90, less than 80, less than 70, less than 60, less than 50, less than 45, less than 40, less than 35, less than 34, less than 33, less than 32, less than 31, less than 30, less than 29, less than 28, less than 27, or less than 25 bases or nucleotides (e.g., a miRNA). In some embodiments, the technology provides for the discrimination of two nucleic acid molecules that differ by as few as one nucleotide. In some embodiments, the technology provides for the discrimination of two nucleic acid molecules when one of the two nucleic acid molecules is present in a large excess (e.g., 10×; 100×; 1000×; 10,000×; or 1,000,000× or more in excess).

Poisson Processes

Embodiments of the technology are related to single-molecule recognition by recording the characteristic kinetics of a probe binding to a target. In particular embodiments, this process is a Poisson process. A Poisson process is a continuous-time stochastic process that counts the number of events and the time that events (e.g., transient binding of a detectably labeled (e.g., fluorescent) query probe to an immobilized target) occur in a given time interval. The time interval between each pair of consecutive events has an exponential distribution and each interval is assumed to be independent of other intervals. The Poisson distribution is a discrete probability distribution that expresses the probability of a given number of the events occurring in the given time interval if these events occur with a known average rate and independently of the time since the last event. The Poisson distribution can also be used for the number of events in other specified intervals such as distance, area, or volume.

A Poisson distribution is a special case of the general binomial distribution where the number of trials n is large, the probability of success p is small, and the product $np=\lambda$ is moderate. In a Poisson process, the probability that a number of events N is j at any arbitrary time t follows the Poisson probability distribution $P_j(t)$:

$$P_j(t) = \frac{e^{-\lambda t}(\lambda t)^j}{j!}, \quad (1)$$

$$j = 0, 1, 2, \ldots .$$

That is, the number N of events that occur up to time t has a Poisson distribution with parameter λt. Statistical and mathematical methods relevant to Poisson processes and Poisson distributions are known in the art. See, e.g., "Stochastic Processes (i): Poisson Processes and Markov Chains" in *Statistics for Biology and Health—Statistical Methods in Bioinformatics* (Ewans and Grant, eds.), Springer (New York, 2001), page 129 et seq., incorporated herein by reference in its entirety. Software packages such as MATLAB software and R may be used to perform mathematical and statistical methods associated with Poisson processes, probabilities, and distributions.

Kinetics of Detection

Particular embodiments of the technology are related to detecting a nucleic acid by analyzing the kinetics of the interaction of a query probe with a query region of a target nucleic acid to be detected. For the interaction of a query probe Q (e.g., at an equilibrium concentration [Q]) with a target nucleic acid T (e.g., at an equilibrium concentration [T]), the kinetic rate constant $k_{on}$ describes the time-dependent formation of the complex QT comprising the probe Q hybridized to the query region of the target nucleic acid T. In particular embodiments, while the formation of the QT complex is associated with a second order rate constant that is dependent on the concentration of query probe and has units of $M^{-1}min^{-1}$ (or the like), the formation of the QT complex is sufficiently described by a $k_{on}$ that is a pseudo-first order rate constant associated with the formation of the QT complex. Thus, as used herein, $k_{on}$ is an apparent ("pseudo") first-order rate constant.

Likewise, the kinetic rate constant $k_{off}$ describes the time-dependent dissociation of the complex QT into the probe Q and the target nucleic acid T. Kinetic rates are typically provided herein in units of $min^{-1}$ or $s^{-1}$. The "dwell time" of the query probe Q in the bound state ($\tau_{on}$) is the time interval (e.g., length of time) that the probe Q is hybridized to the query region of the target nucleic acid T during each instance of query probe Q binding to the query region of the target nucleic acid T to form the QT complex. The "dwell time" of the query probe Q in the unbound state ($\tau_{off}$) is the time interval (e.g., length of time) that the probe Q is not hybridized to the query region of the target nucleic acid T between each instance of query probe Q binding to the query region of the target nucleic acid T to form the QT complex (e.g., the time the query probe Q is dissociated from the target nucleic acid T between successive binding events of the query probe Q to the target nucleic acid T). Dwell times may be provided as averages or weighted averages integrating over numerous binding and non-binding events.

Further, in some embodiments, the repeated, stochastic binding of probes (e.g., detectably labeled query probes (e.g., fluorescent probes), e.g., nucleic acid probes such as DNA or RNA probes) to immobilized targets is modeled as a Poisson process occurring with constant probability per unit time and in which the standard deviation in the number of binding and dissociation events per unit time ($N_{b+d}$) increases as $(N_{b+d})^{1/2}$. Thus, the statistical noise becomes a smaller fraction of $N_{b+d}$ as the observation time is increased. Accordingly, the observation is lengthened as needed in some embodiments to achieve discrimination between target and off-target binding. And, as the acquisition time is increased, the signal and background peaks in the $N_{b+d}$ histogram become increasingly separated and the width of the signal distribution increases as the square root of $N_{b+d}$, consistent with kinetic Monte Carlo simulations. During the development of embodiments of the technology provided herein, data indicated that an acquisition time of approximately 10 minutes (e.g., approximately 1 to 100 minutes, e.g., 1, 2, 3, 4, 5, 6, 7, 8, 9, 10, 11, 12, 13, 14, 15, 16, 17, 18, 19, 20, 30, 40, 50, 60, 70, 80, 90, or 100 minutes) yields sufficient (e.g., complete) separation of the signal from background distributions of $N_{b+d}$, providing for substantially background-free quantification of the target.

Further, in some embodiments the probe length is chosen to provide sufficient separation of signal and background peaks on convenient experimental time scales. In particular, the kinetics of query probe exchange are related to the number of complementary bases between the query probe and target nucleic acid. For instance, in some embodiments, the interaction of a short DNA probe with its complement increases as an approximately exponential function of the number of base pairs formed, while the rate constant of binding is affected only weakly for interactions comprising at least 6 to 7 base pairs. Thus, varying query probe length provides for tuning the kinetic behavior to improve discrimination of query probe binding events to the target from background binding. During experiments conducted during the development of embodiments of the technology provided herein, data were collected indicating that a query (e.g., fluorescent) probe length of 9 nt to 10 nt (providing theoretical $T_m$ values of 17.5° C. to 25° C.) yields rapid target binding that is distinguished from background signal, as displayed in histograms of intensity transitions per candidate molecule in the presence and absence of target. Further, in some embodiments the kinetics of binding and dissociation are more closely correlated to probe length than to the melting temperature of the duplex. While some embodiments comprise use of a probe having a length of 9 to 10 nt, the technology is not limited by this length. Indeed, use of probes longer or shorter than 9 to 10 nt is contemplated by the technology, e.g., as discussed throughout.

Compositions

Some embodiments provide compositions, reaction mixtures, and complexes comprising a plurality of molecules for detecting one or more nucleic acids. These compositions, reaction mixtures, and complexes comprise, in some embodiments, a nucleic acid (e.g., a target nucleic acid) that is to be detected, identified, quantified, and/or characterized; a capture probe (e.g., a nucleic acid capture probe); and a detectably labeled (e.g., fluorescent) query probe (see, e.g., FIG. 1A and FIG. 1B).

The nucleic acid to be detected, characterized, quantified, and/or identified (e.g., the target nucleic acid) comprises two regions. One region (e.g., the capture region) is sufficiently complementary to a capture probe (e.g., for immobilization of the nucleic acid to a solid support) and the other region (e.g., the query region) is complementary to a labeled (e.g., fluorescently labeled) query probe (e.g., for kinetic detection of the nucleic acid) (see FIG. 1A and FIG. 1B). The query region is typically from 6 to 12 nucleotides (e.g., 6, 7, 8, 9, 10, 11, or 12 nucleotides) and the length is defined in part by the length and sequence of the query probe. The capture region typically comprises at least 10 nucleotides. Thus, the target nucleic acid typically comprises, e.g., at least 16 nucleotides, but may be shorter in some embodiments. The target nucleic acid may be RNA, DNA, or a modified form of RNA or DNA. The target nucleic acid may comprise a mixture of DNA and RNA.

The capture probe forms a thermodynamically stable hybrid with the nucleic acid capture region. The thermodynamically stable hybrid immobilizes the nucleic acid (e.g., to a solid support, e.g., a solid support to which the capture probe is attached) (see FIG. 1A). In some embodiments, the capture probe provides a preliminary specificity filter by capturing a subset of nucleic acid molecules in a sample, e.g., the capture probe captures the nucleic acid molecules that comprise a sequence within the capture region that is sufficiently complementary to the capture probe to effect formation of a thermodynamically stable complex. The capture probe, however, is not responsible for the kinetic fingerprinting that is the hallmark of the technology as described herein.

In some embodiments, one or more nucleotides of the capture probe comprise a modified nucleotide (e.g., a locked nucleic acid (LNA nucleotide)) (see FIG. 1B, underlined nucleotides in exemplary capture probe sequence). A locked nucleic acid is a modified RNA nucleotide wherein the ribose moiety of the nucleotide is modified to connect the 2' oxygen and 4' carbon. The connection "locks" the ribose in the 3'-endo ("North") conformation, which is often found in A-form duplexes. In some embodiments, LNA nucleotides are mixed with DNA or RNA residues in the oligonucleotide whenever desired. Such oligomers are synthesized chemically and are commercially available. The locked ribose conformation enhances base stacking and backbone pre-organization, which significantly increases the hybridization properties (e.g., increases thermodynamic stability and melting temperature) of oligonucleotides. Accordingly, LNA nucleotides increase the sensitivity and specificity of probes and other molecular biology techniques based on the hybridization of oligonucleotides.

In some embodiments, the capture probe is attached or fixed to a solid support. In some embodiments, the capture probe comprises a moiety that provides for the immobilization of the capture probe to a solid support by interaction of the moiety with a second moiety attached to the solid support. The capture probe may be fixed directly or indirectly to a solid support (FIG. 1A).

Any of a variety of materials may be used as a support for the capture probe, e.g., matrices or particles made of nitrocellulose, nylon, glass, polyacrylate, mixed polymers, polystyrene, silane polypropylene, and magnetically attractable materials. A planar surface is a preferred support for imaging by microscopy as described herein (see, e.g., the examples). A capture probe may be immobilized by linking it directly to the solid support, e.g., by using any of a variety of covalent linkages, chelation, or ionic interaction, or may be immobilized by linking it indirectly via one or more linkers joined to the support. In some embodiments, the linker is a nucleic acid; in some embodiments, the linker is a nucleic acid comprising one or more nucleotides that is/are not intended to hybridize (e.g., that do not hybridize) to the target nucleic acid capture region but that are intended to act as a spacer between the capture probe and its solid support.

In some embodiments, the capture probe comprises a biotin group (e.g., the capture probe is biotinylated) and the solid support comprises a streptavidin group (e.g., attached to the solid support by a linker moiety, e.g., a polyethylene glycol (PEG) linker). The specific interaction of the biotin and streptavidin thus immobilizes the capture probe to the solid support (FIG. 1A).

Various other chemical methods can be employed for the immobilization of probes to a solid support. An example of such a method is to use a combination of a maleimide group and a thiol (—SH) group. In this method, a thiol (—SH) group is bonded to the terminal of a probe, and the solid support comprises a maleimide group. Accordingly, the thiol group of the probe reacts with the maleimide group on the solid support to form a covalent bond, whereby the probe is immobilized. Introduction of the maleimide group can utilize a process of firstly allowing a reaction between a glass substrate and an aminosilane coupling agent and then introducing the maleimide group onto the glass substrate by a reaction of the amino group with an EMCS reagent (N-(6-maleimidocaproyloxy)succinimide, available from Dojindo). Introduction of the thiol group to a DNA can be carried out using 5'-Thiol-Modifier C6 (available from Glen Research) when the DNA is synthesized by an automatic DNA synthesizer.

Instead of the above-described combination of a thiol group and a maleimide group, a combination of, e.g., an epoxy group (on the solid support) and an amino group (nucleic acid probe terminal), is used in some embodiments as a combination of functional groups for immobilization. Surface treatments using various kinds of silane coupling agents are also effective. Other techniques for the attachment of nucleic acid molecules to solid supports and solid surfaces include those provided by, e.g., Adessi et al. (2003) "Solid Phase DNA Amplification: Characterization of Primer Attachment and Amplification Mechanisms" Nucleic Acids Res. 28: e87; Call et al. (2001) "Fabrication of DNA Microarrays Using Unmodified Oligonucleotide Probes" BioTechniques 30: 368-379; Guo et al. (1994) "Direct Fluorescence Analysis of Genetic Polymorphisms by Hybridization with Oligonucleotide Arrays on Glass Supports" Nucleic Acids Res. 22: 5456-5465, each of which is incorporated herein it its entirety.

In some embodiments, the capture probe is substantially or exactly complementary to at least a portion of the target nucleic acid (e.g., to at least a portion of the capture region of the target nucleic acid). In some embodiments related to capture probes that are nucleic acids, the capture probe may be any length of nucleotides, e.g., from approximately 10 to approximately 500 nucleotides or nucleobases (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 100, 150, 200, 250, 300, 350, 400, 450, or 500 or more nucleotides or nucleobases). The capture probe comprises a target binding region that is sufficiently complementary to the capture region of the target nucleic acid to form a thermodynamically stable hybrid and thus immobilize the target nucleic acid to the solid support. The target binding region and the capture region are sufficiently complementary and each typically comprises approximately 10 to 100 or more nucleotides or nucleobases (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 100, 150, 200, 250, 300, 350, 400, 450, or 500 or more nucleotides or nucleobases). The capture probe is typically provided in single-stranded form, or, if not, is denatured to single-stranded form before or during use.

The technology comprises use of a query probe to detect a nucleic acid. The query probe hybridizes to the query region of the target nucleic acid, but does not form a thermodynamically stable hybrid with the query region. In particular, the query probe hybridizes with the query region with a standard Gibbs free energy of greater than approximately −12 kcal/mol, e.g., a standard Gibbs free energy of greater than approximately −10 kcal/mol (e.g., at a standard temperature of 37° C.). In some embodiments, the hybridized complex comprising the query probe and the target nucleic acid has a melting temperature of approximately less than 40° C., e.g., less than 35° C. or even less than 25° C. (see FIG. 1B). Accordingly, in some embodiments the query probe does not comprise LNA nucleotides or other modifications that stabilize formation of thermodynamically stable hybrids. In some embodiments the query probe comprises a modification (e.g., an LNA nucleotide or other modification that tends to stabilize formation of thermodynamically stable hybrids), but the query probes retain their function as otherwise described herein.

The interaction of the query probe with the query region of the target nucleic acid is characterized by kinetic parameters. Thus, in some embodiments the kinetic rate constant $k_{on}$ describing the association of the query probe with the query region of the nucleic acid to form a hybrid and/or the kinetic rate constant $k_{off}$ describing the dissociation of the hybrid is/are greater than 0.1 min$^{-1}$ (e.g., greater that approximately 0.002 s$^{-1}$) or greater than 1 min$^{-1}$ (e.g., greater than approximately 0.02 s$^{-1}$). In some embodiments, the kinetic rate constant $k_{on}$ describing the association of the query probe with the query region of the nucleic acid to form a hybrid and/or the kinetic rate constant $k_{off}$ describing the dissociation of the hybrid is/are greater than 0.001 s$^{-1}$, e.g., greater than 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, or 8 s$^{-1}$.

In some embodiments, the query probe comprises a label, e.g., a fluorescent label as described below (see also, e.g., FIG. 1A and FIG. 1B).

In some embodiments, a label is detected by changes in light scattering (e.g., interferometric detection of scattering; see, e.g., Piliarik and Sandoghdar (2014) "Direct optical sensing of single unlabelled proteins and super-resolution imaging of their binding sites" Nature Communications 5: 4495).

In some embodiments, vibrational spectroscopy, photothermal detection, plasmonics and microcavities find use for the detection of query probe kinetics.

In some embodiments, the query probe is a probe (e.g., a DNA probe, an RNA probe) comprising 6 to 12 nucleotides (e.g., 6, 7, 8, 9, 10, 11, or 12 nucleotides). Without being bound by theory, a longer probe would form a thermodynamically stable hybrid and thus the technology would suffer from the problems associated with thermodynamic discrimination in existing technologies; and a shorter probe would bind with a low affinity and a low specificity that would compromise detection of the bound probe. The query probe is typically provided in single-stranded form, or, if not, is denatured to single-stranded form before or during use.

While certain embodiments described herein are related to or comprise a capture probe that is a nucleic acid and/or a query probe that is a nucleic acid, the technology is not limited to such embodiments (e.g., the technology is not limited by a capture probe that is a nucleic acid; the technology is not limited by a query probe that is a nucleic acid). Accordingly, in some embodiments the capture probe and/or query probe as described herein is/are any entity (e.g., molecule, biomolecule, etc.) that recognizes a nucleic acid. For example, in some embodiments the capture probe and/or query probe comprises an entity that recognizes a nucleic acid. In exemplary embodiments, the entity that recognizes a nucleic acid is a protein that recognizes a nucleic acid (e.g., a nucleic acid binding protein, an antibody, a transcription factor, or any other protein that binds to a particular sequence in a nucleic acid). In some embodiments, the capture probe and/or query probe comprises more than one type of molecule (e.g., a protein, a nucleic acid, a chemical linker or chemical moiety that recognizes a nucleic acid).

microRNA

In some embodiments, the nucleic acid to be detected, characterized, quantified, and/or identified (e.g., the target nucleic acid) is a microRNA. microRNAs (miRNA or μRNA) are single-stranded RNA molecules of approximately 21 to 23 nucleotides in length that regulate gene expression. miRNAs are encoded by genes from whose DNA they are transcribed, but miRNAs are not translated into protein (see, e.g., Carrington et al, 2003, which is hereby incorporated by reference). The genes encoding miRNAs are much longer than the processed mature miRNA molecule.

miRNAs are typically excised from 60- to 70-nucleotide foldback RNA precursor structures, which are sometimes detected at the onset of miRNA precursor expression (Grishok et al., (2001) Cell 106, 23-34; Hutvagner et al. (2001) Science 93, 834-838; Ketting et al., (2001) FGenes Dev. 15, 2654-2659) or during expression of very abundant miRNAs (Lagos-Quintana et al., supra; Lau et al., supra; Lee et al., supra). Generally, only one of the strands of the hairpin precursor molecule is excised and accumulates, presumably because it is protected by associated proteins from RNA degradation. These putative proteins may mediate the translational suppression. The miRNA precursor processing reaction requires Dicer RNase III and Argonaute family members (Grishok et al., supra; Hutvagner et al., supra; Ketting et al., supra).

miRNAs are first transcribed as primary transcripts or pri-miRNA with a cap and a poly-A tail and subsequently processed to short, 70-nucleotide stem-loop structures known as pre-miRNA in the cell nucleus. This processing is performed in animals by a protein complex known as the microprocessor complex comprising the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC. This strand is known as the guide strand and is selected by the Argonaute protein, the catalytically active RNase in the RISC, on the basis of the stability of the 5' end. The remaining strand, known as the miRNA*, anti-guide, or passenger strand, is degraded as a RISC substrate. Therefore, the miRNA*s are derived from the same hairpin structure like the "normal" miRNAs. So if the "normal" miRNA is then later called the "mature miRNA" or "guide strand", the miRNA* is the passenger strand.

The miRNA*s, also known as the anti-guide or passenger strand, are mostly complementary to the guide strand, but there are usually single-stranded overhangs on each end, there is usually one or a few mispairs and there are sometimes extra or missing bases causing single-stranded "bubbles". The miRNA*s are likely to act in a regulatory fashion as the miRNAs. It is understood that according to the present invention the term "miRNA" also includes the term "miRNA*".

A well established repository of validated miRNAs is the miRBase. The miRBase is a searchable database of published miRNA sequences and annotations and is available on the internet. Each entry in the miRBase sequence database represents a predicted hairpin portion of a miRNA transcript (termed mir in the database), with information on the location and sequence of the mature miRNA sequence (termed miR). Both hairpin and mature sequences are available for searching and browsing, and entries can also be retrieved by name, keyword, references, and annotation. All sequence and annotation data are also available for download.

Several miRNAs, such as let-7, miR-1, miR-34, miR-60, and miR-87, are highly conserved between invertebrates and vertebrates, implicating that they may recognize multiple sites and/or multiple targets of presumably conserved function (Lagos-Quintana et al., supra; Lau et al., supra; Lee et al., supra; Pasquinelli et al., (2000) Nature 408:86). The small temporal RNAs (stRNAs) lin-4 and let-7 represent a subclass of miRNAs identified by genetic analysis in *Caenorhabditis elegans*, which are developmentally regulated and themselves control developmental programs, such as timing of neuronal rewiring, Dauer larva formation, vulva formation, and the terminal differentiation of hypodermal cells. During the development of embodiments of the technology provided herein, experiments used the particular miRNAs let-7a, hsa-miR-16, hsa-miR-21, cel-miR-39, and hsa-miR-141. The sequences of these miRNAs and related information are available in miRBase.

Like miRNAs, small interfering RNAs (siRNAs) are small RNA molecules involved in cell defense, e.g. against viral RNA, via a response termed RNA interference (RNAi) (Cullen, B. R., Nature Immunology, 3: 597-599 (2002)). One class of siRNAs is produced through the action of the Dicer enzyme and RNA-induced silencing complex (RISC) protein complex as part of the RNAi response to the presence of double stranded RNA in cells (Khvorova, A. et al., Cell 115: 209-216 (2003)). Another class of siRNAs is synthetic and encompasses short duplexes, usually 21-23 nt with characteristic dinucleotide overhangs (Elbashir, S. M. et al., EMBO J. 20: 6877-6888 (2001)) introduced directly into cells via transfection or expression from an introduced vector (Paul, C. P. et al., Nature Biotechnology 20: 505-508 (2002), U.S. Patent Application Publication No. 2003/0148519A1, herein incorporated by reference in its entirety for all purposes). In some cases, siRNAs appear to persist as defined sequences, making them analogous in function and composition to miRNAs (Elbashir, S. M. et al., supra).

In addition to their impact on gene expression, these small RNAs, often in the range of 21-22 nucleotides, find utility in areas of therapeutics and drug discovery, e.g. as drug targets or as pharmaceutical agents. Thus, in some circumstances, it may be important to know approximately how much of each miRNA exists in cells. In some cases, it may further be important to compare levels of miRNA in different tissue types or before and after application of a stimulus, e.g. a chemical or physical intervention. Because related siRNAs and miRNAs may be present in low amounts in cells, it is desirable that methods of detection be both sensitive and specific. Moreover, for certain applications, it may be beneficial to identify methods suitable for high throughput screening, e.g., homogeneous methods, multiplexed methods, or those suitable to highly parallel automated manipulation and limited temperature changes.

Fluorescent Moieties

In some embodiments, a nucleic acid comprises a fluorescent moiety (e.g., a fluorogenic dye, also referred to as a "fluorophore" or a "fluor"). A wide variety of fluorescent moieties is known in the art and methods are known for linking a fluorescent moiety to a nucleotide prior to incorporation of the nucleotide into an oligonucleotide and for adding a fluorescent moiety to an oligonucleotide after synthesis of the oligonucleotide.

Examples of compounds that may be used as the fluorescent moiety include but are not limited to xanthene, anthracene, cyanine, porphyrin, and coumarin dyes. Examples of xanthene dyes that find use with the present technology include but are not limited to fluorescein, 6-carboxyfluorescein (6-FAM dye), 5-carboxyfluorescein (5-FAM dye), 5- or 6-carboxy-4, 7, 2', 7'-tetrachlorofluorescein (TET dye), 5- or 6-carboxy-4'5'2'4'5'7' hexachlorofluorescein (HEX dye), 5' or 6'-carboxy-4',5'-dichloro-2,'7'-dimethoxyfluorescein (JOE dye), 5-carboxy-2',4',5',7'-tetrachlorofluorescein (ZOE dye), rhodol, rhodamine, tetramethylrhodamine (TAMRA dye), 4,7-dlchlorotetramethyl rhodamine (DTAMRA dye), rhodamine X (ROX dye), and TEXAS RED dye. Examples of cyanine dyes that may find use with the present invention include but are not limited to CY3 dye, CY3B dye, CY3.5 dye, CY5 dye, CY5.5 dye, CY7 dye, and CY7.5 dye. Other fluorescent moieties and/or dyes that find use with the present technology include but are not limited to energy transfer dyes, composite dyes, and other aromatic compounds that give fluorescent signals. In some embodiments, the fluorescent moiety comprises a quantum dot.

Fluorescent dyes include, without limitation, d-Rhodamine acceptor dyes including CY5 dye, dichloro[R110], dichloro[R6G], dichloro[TAMRA], dichloro[ROX] or the like, fluorescein donor dyes including fluorescein, 6-FAM, 5-FAM, or the like; Acridine including Acridine orange, Acridine yellow, Proflavin, pH 7, or the like; Aromatic Hydrocarbons including 2-Methylbenzoxazole, Ethyl p-dimethylaminobenzoate, Phenol, Pyrrole, benzene, toluene, or the like; Arylmethine Dyes including Auramine O, Crystal violet, Crystal violet, glycerol, Malachite Green or the like; Coumarin dyes including 7-Methoxycoumarin-4-acetic acid, Coumarin 1, Coumarin 30, Coumarin 314, Coumarin 343, Coumarin 6 or the like; Cyanine Dyes including 1,1'-diethyl-2,2'-cyanine iodide, Cryptocyanine, Indocarbocyanine (C3) dye, Indodicarbocyanine (C5) dye, Indotricarbocyanine (C7) dye, Oxacarbocyanine (C3) dye, Oxadicarbocyanine (C5) dye, Oxatricarbocyanine (C7) dye, Pinacyanol iodide, Stains all, Thiacarbocyanine (C3) dye, ethanol, Thiacarbocyanine (C3) dye, n-propanol, Thiadicarbocyanine (C5) dye, Thiatricarbocyanine (C7) dye, or the like; Dipyrrin dyes including N,N'-Difluoroboryl-1,9-dimethyl-5-(4-iodophenyl)-dipyrrin, N,N'-Difluoroboryl-1,9-dimethyl-5-[(4-(2-trimethylsilylethynyl), N,N'-Difluoroboryl-1,9-dimethyl-5-phenydipyrrin, or the like; Merocyanines including 4-(dicyanomethylene)-2-methyl-6-(p-dimethylaminostyryl)-4H-pyran (DCM), acetonitrile, 4-(dicyanomethylene)-2-methyl-6-(p-dimethylaminostyryl)-4H-pyran (DCM), methanol, 4-Dimethylamino-4'-nitrostilbene, Merocyanine 540, or the like; Miscellaneous Dyes including 4',6-Diamidino-2-phenylindole (DAPI), dimethylsulfoxide, 7-Benzylamino-4-nitrobenz-2-oxa-1,3-diazole, Dansyl glycine, Dansyl glycine, dioxane, Hoechst 33258, DMF, Hoechst 33258, Lucifer yellow CH, Piroxicam, Quinine sulfate, Quinine sulfate, Squarylium dye III, or the like; Oligophenylenes including 2,5-Diphenyloxazole (PPO), Biphenyl, POPOP, p-Quaterphenyl, p-Terphenyl, or the like; Oxazines including Cresyl violet perchlorate, Nile Blue, methanol, Nile Red, ethanol, Oxazine 1, Oxazine 170, or the like; Polycyclic Aromatic Hydrocarbons including 9,10-Bis (phenylethynyl)anthracene, 9,10-Diphenylanthracene, Anthracene, Naphthalene, Perylene, Pyrene, or the like; polyene/polyynes including 1,2-diphenylacetylene, 1,4-diphenylbutadiene, 1,4-diphenylbutadiyne, 1, 6-Diphenylhexatriene, Beta-carotene, Stilbene, or the like; Redoxactive Chromophores including Anthraquinone, Azobenzene, Benzoquinone, Ferrocene, Riboflavin, Tris(2, 2'-bipyridypruthenium(II), Tetrapyrrole, Bilirubin, Chlorophyll a, diethyl ether, Chlorophyll a, methanol, Chlorophyll b, Diprotonated-tetraphenylporphyrin, Hematin, Magnesium octaethylporphyrin, Magnesium octaethylporphyrin (MgOEP), Magnesium phthalocyanine (MgPc), PrOH, Magnesium phthalocyanine (MgPc), pyridine, Magnesium tetramesitylporphyrin (MgTMP), Magnesium tetraphenylporphyrin (MgTPP), Octaethylporphyrin, Phthalocyanine (Pc), Porphin, ROX dye, TAMRA dye, Tetra-t-butylazaporphine, Tetra-t-butylnaphthalocyanine, Tetrakis(2,6-dichlorophenyDporphyrin, Tetrakis(o-aminophenyl)porphyrin, Tetramesitylporphyrin (TMP), Tetraphenylporphyrin (TPP), Vitamin B12, Zinc octaethylporphyrin (ZnOEP), Zinc phthalocyanine (ZnPc), pyridine, Zinc tetramesitylporphyrin (ZnTMP), Zinc tetramesitylporphyrin radical cation, Zinc tetraphenylporphyrin (ZnTPP), or the like; Xanthenes including Eosin Y, Fluorescein, basic ethanol, Fluorescein, ethanol, Rhodamine 123, Rhodamine 6G, Rhodamine B, Rose bengal, Sulforhodamine 101, or the like; or mixtures or combination thereof or synthetic derivatives thereof.

Several classes of fluorogenic dyes and specific compounds are known that are appropriate for particular embodiments of the technology: xanthene derivatives such as fluorescein, rhodamine, Oregon green, eosin, and TEXAS RED dye; cyanine derivatives such as cyanine, indocarbocyanine, oxacarbocyanine, thiacarbocyanine, and merocyanine; naphthalene derivatives (dansyl and prodan derivatives); coumarin derivatives; oxadiazole derivatives such as pyridyloxazole, nitrobenzoxadiazole, and benzoxadiazole; pyrene derivatives such as cascade blue; oxazine derivatives such as Nile red, Nile blue, cresyl violet, and oxazine 170; acridine derivatives such as proflavin, acridine orange, and acridine yellow; arylmethine derivatives such as auramine, crystal violet, and malachite green; and tetrapyrrole derivatives such as porphin, phtalocyanine, bilirubin. In some embodiments the fluorescent moiety a dye that is xanthene, fluorescein, rhodamine, BODIPY, cyanine, coumarin, pyrene, phthalocyanine, phycobiliprotein, ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700, ALEXA FLUOR® 750, or a squaraine dye. In some embodiments, the label is a fluorescently detectable moiety as described in, e.g., Haugland (September 2005) MOLECULAR PROBES HANDBOOK OF FLUORESCENT PROBES AND RESEARCH CHEMICALS (10th ed.), which is herein incorporated by reference in its entirety.

In some embodiments the label (e.g., a fluorescently detectable label) is one available from ATTO-TEC GmbH (Am Eichenhang 50, 57076 Siegen, Germany), e.g., as described in U.S. Pat. Appl. Pub. Nos. 20110223677, 20110190486, 20110172420, 20060179585, and 20030003486; and in U.S. Pat. No. 7,935,822, all of which are incorporated herein by reference (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO740).

One of ordinary skill in the art will recognize that dyes having emission maxima outside these ranges may be used as well. In some cases, dyes ranging between 500 nm to 700 nm have the advantage of being in the visible spectrum and can be detected using existing photomultiplier tubes. In some embodiments, the broad range of available dyes allows selection of dye sets that have emission wavelengths that are spread across the detection range. Detection systems capable of distinguishing many dyes are known in the art.

Methods

The technology is related in some embodiments to methods for the detection of a nucleic acid, e.g., a short nucleic acid such as a miRNA, in a sample. First, the nucleic acid is immobilized to a solid support by binding the nucleic acid to an immobilized capture probe (e.g., an immobilized capture probe (e.g., a biotinylated capture probe) comprising a LNA nucleotide). Binding the target nucleic acid to the immobilized capture probes provides a solid support comprising a plurality of immobilized target nucleic acids on its surface. Then, a composition comprising a query probe (e.g., a fluorescently labeled query probe) of 6 to 12 nucleotides (e.g., 6, 7, 8, 9, 10, 11, or 12 nucleotides) is added to the sample. Then, the binding of query probes to each immobilized target nucleic acid is observed.

Some embodiments are related to use of a solid support comprising multiple immobilized capture probes. The multiple immobilized capture probes may bind the same or different targets. In some embodiments, the multiple immobilized capture probes are arranged as an array on a solid support. Each capture probe in array comprises a region that binds to a target and a region that links the capture probe to the solid support. The capture probe oligonucleotides contain DNA, RNA, and/or mixtures and/or modifications thereof.

Methods for synthesizing or obtaining oligonucleotide probe molecules are well known in the art. For example, probes (e.g., capture probes, query probes) can be made using an automated DNA synthesizer, e.g., an Applied Biosystems, Inc. (Foster City, Calif.) model 392 or 394 DNA/RNA Synthesizer, and standard chemical methods, such as phosphoramidite chemistry, which can be adapted as needed for incorporation of modified or nonstandard bases, if desired (see, e.g., Beaucage et al., Tetrahedron 48:2223-2311, 1992; Molko et al., U.S. Pat. No. 4,980,460; Koster et al., U.S. Pat. No. 4,725,677; Caruthers et al., U.S. Pat. Nos. 4,415,732, 4,458,066, and 4,973,679). Alternative chemistries that result in non-natural backbone groups, such as phosphorothioate, methylphosphonate, or phosphoramidate backbones, can also be employed to make capture probes, provided that the resulting oligonucleotides are capable of hybridization to a target as described herein. In some embodiments, oligonucleotides include nucleotides that permit processing or manipulation by enzymes, or non-naturally occurring nucleotide analogs, such as peptide nucleic acids or locked nucleic acid, that promote the formation of more stable duplexes than standard nucleotides.

Capture probes of an array are bound to a solid support in discrete, predetermined areas often referred to as "features". The number of probes bound to each feature (and thus the number of probes per array) will vary, depending on the type of capture probe used and the specific application, and can readily be determined by one of skill in this art. For example, an individual feature of an array, which includes identical probes, may include more than 10,000 probes/pmt. Also, the size of each feature can vary according to the particular use, and can range, for example, from several $\mu m^2$, e.g., 10 to 20, to several thousand $\mu m^2$, e.g., 1,000 to 30,000 $\mu m^2$. Preferably, the features are spatially discrete, so that signals generated by events, such as fluorescent emissions, at adjacent features can be resolved by use of a standard detection method.

Capture probe arrays are fabricated on solid supports, such as, for example, glass (e.g., glass microscope slides or coverslips), plastic, alkanethiolate-derivatized gold, cellulose, polystyrene, silica gel, polyamide, functionalized glass, Si, Ge, GaAs, GaP, $SiO_2$, $SIN_4$, modified silicone, polymerized Langmuir Blodgett film, or any one of a wide variety of polymers, such as (poly)tetrafluoroethylene, (poly)vinylidenedifluoride, or combinations thereof. For example, the solid support can be a flat glass or single-crystal silicon with surface features of less than 10 angstroms.

The solid support can be coated with a surface material, such as a polymer, plastic, resin, polysaccharide, silica, silica-based material, carbon, metal, inorganic glass, or membrane, as can be selected by one of skill in this art. It may be desirable for the surface of the solid support to include a layer of crosslinking groups. For example, when thiols are used to link probes to the surface, solid supports coated with an intermediate linker layer such as aryl acetylenes, ethylene glycol oligomers, diamines, diacids, amino acids, or combinations thereof, can be used (see, e.g., U.S. Pat. No. 5,412,087).

The capture probes can be synthesized directly on a feature of a solid support or synthesized elsewhere, and then added as an intact species that is covalently linked to the feature of the substrate. Numerous methods (e.g., photolithographic methods; see, e.g., Sze, VLSI Technology, McGraw-Hill, 1983; Mead et al., Introduction to VLSI Systems, Addison-Wesley, 1980) for attaching biological polymers, such as oligonucleotides (DNA or RNA), proteins, peptides, and carbohydrates, to solid supports are known in the art, and can be used to make the capture arrays of the invention. For example, McGall et al. (U.S. Pat. No. 5,412,087) describes a process in which a substrate is coated with compounds having thiol functional groups that are protected with photoremovable protecting groups. Probes, such as oligonucleotide probes or other biological polymers, can be linked to different regions of such a substrate by spatial irradiation, which results in removal of protecting groups at pre-defined regions of the surface.

Additional methods for attaching molecules, such as oligonucleotides, onto solid supports are described, for example, in U.S. Pat. No. 5,601,980, U.S. Pat. No. 4,542, 102, WO 90/07582, U.S. Pat. No. 4,937,188, U.S. Pat. No. 5,011,770, WO 91/00868, U.S. Pat. No. 5,436,327, U.S. Pat. No. 5,143,854, WO 90/15070, Fodor et al., Science 251: 767-773, 1991, Dower et al., Ann. Rev. Med. Chem. 26:271-280, 1991, U.S. Pat. No. 5,252,743, WO 91/07087, U.S. Pat. No. 5,445,934, U.S. Pat. No. 5,744,305, and U.S. Pat. No. 5,624,711. Also see U.S. Pat. Nos. 5,604,097, 5,635,400, 5,654,413, and 5,695,934.

In some embodiments, the detectable (e.g., fluorescent) query probe produces a fluorescence emission signal when it is close to the surface of the solid support (e.g., within about 100 nm of the surface of the solid support). When unbound, query probes quickly diffuse and thus are not individually detected; accordingly, when in the unbound state, the query probes produce a low level of diffuse background fluorescence. Consequently, in some embodiments detection of bound query probes comprises use of total internal reflection fluorescence microscopy (TIRO, HiLo microscopy (see, e.g., US20090084980, EP2300983 B1, WO2014018584 A1, WO2014018584 A1, incorporated herein by reference), confocal scanning microscopy, or other technologies comprising illumination schemes that illuminate (e.g., excite) only those query probe molecules near or on the surface of the solid support. Thus, in some embodiments, only query probes that are bound to an immobilized target near or on the surface produce a point-like emission signal (e.g., a "spot") that can be confirmed as originating from a single molecule.

In general terms, the observation comprises monitoring fluorescence emission at a number of discrete locations on the solid support where the target nucleic acids are immobilized (e.g., at a number of fluorescent "spots" that blink, e.g., that can be in "on" and "off" states). The presence of fluorescence emission (spot is "on") and absence of fluorescence emission (spot is "off") at each discrete location (e.g., at each "spot" on the solid support) are recorded. Each spot "blinks"—e.g., a spot alternates between "on" and "off" states, respectively, as a query probe binds to the immobilized target nucleic acid at that spot and as the query probe dissociates from the immobilized target nucleic acid at that spot.

The data collected provide for the determination of the number of times a query probe binds to each immobilized target (e.g., the number of times each spot blinks "on") and a measurement of the amount of time a query probe remains bound (e.g., the length of time a spot remains "on" before turning "off").

In some embodiments, the query probe comprises a fluorescent label having an emission wavelength. Detection of fluorescence emission at the emission wavelength of the fluorescent label indicates that the query probe is bound to an immobilized target nucleic acid. Binding of the query probe to the target nucleic acid is a "binding event". In some embodiments of the technology, a binding event has a fluorescence emission having a measured intensity greater than a defined threshold. For example, in some embodiments a binding event has a fluorescence intensity that is above the background fluorescence intensity (e.g., the fluorescence intensity observed in the absence of a target nucleic acid). In some embodiments, a binding event has a fluorescence intensity that is at least 1, 2, 3, 4 or more standard deviations above the background fluorescence intensity (e.g., the fluorescence intensity observed in the absence of a target nucleic acid). In some embodiments, a binding event has a fluorescence intensity that is at least 2 standard deviations above the background fluorescence intensity (e.g., the fluorescence intensity observed in the absence of a target nucleic acid). In some embodiments, a binding event has a fluorescence intensity that is at least 1.5, 2, 3, 4, or 5 times the background fluorescence intensity (e.g., the mean fluorescence intensity observed in the absence of a target nucleic acid).

Accordingly, in some embodiments detecting fluorescence at the emission wavelength of the fluorescent probe that has an intensity above the defined threshold (e.g., at least 2 standard deviations greater than background intensity) indicates that a binding event has occurred (e.g., at a discrete location on the solid support where a target nucleic acid is immobilized). Also, in some embodiments detecting fluorescence at the emission wavelength of the fluorescent probe that has an intensity above the defined threshold (e.g., at least 2 standard deviations greater than background intensity) indicates that a binding event has started. Accordingly, in some embodiments detecting an absence of fluorescence at the emission wavelength of the fluorescent probe that has an intensity above the defined threshold (e.g., at least 2 standard deviations greater than background intensity) indicates that a binding event has ended (e.g., the query probe has dissociated from the target nucleic acid). The length of time between when the binding event started and when the binding event ended (e.g., the length of time that fluorescence at the emission wavelength of the fluorescent probe having an intensity above the defined threshold (e.g., at least 2 standard deviations greater than background intensity) is detected) is the dwell time of the binding event. A "transition" refers to the binding and dissociation of a query probe to the target nucleic acid (e.g., an on/off event).

Methods according to the technology comprise counting the number of query probe binding events that occur at each discrete location on the solid support during a defined time interval that is the "acquisition time" (e.g., a time interval that is tens to hundreds to thousands of seconds, e.g., 5, 10, 15, 20, 25, 30, 35, 40, 45, 50, 55, or 60 seconds; e.g., 5, 10, 15, 20, 25, 30, 35, 40, 45, 50, 55, or 0 minutes; e.g., 1, 1.5, 2, 2.5, or 3 hours). In some embodiments, the acquisition time is approximately 10 minutes (e.g., approximately 1 to 100 minutes, e.g., 1, 2, 3, 4, 5, 6, 7, 8, 9, 10, 11, 12, 13, 14, 15, 16, 17, 18, 19, 20, 30, 40, 50, 60, 70, 80, 90, or 100 minutes).

Further, the length of time the query probe remains bound to the target nucleic acid during a binding event is the "dwell time" of the binding event. The number of binding events detected during the acquisition time and/or the lengths of the dwell times recorded for the binding events is/are characteristic of a query probe binding to a target nucleic acid and thus provide an indication that the target nucleic acid is immobilized at said discrete location and thus that the target nucleic acid is present in the sample.

Binding of the query probe to the immobilized target nucleic acid and/or and dissociation of the query probe from the immobilized target nucleic acid is/are monitored (e.g., using a light source to excite the fluorescent probe and detecting fluorescence emission from a bound query probe, e.g., using a fluorescence microscope) and/or recorded during a defined time interval (e.g., during the acquisition time). The number of times the query probe binds to the nucleic acid during the acquisition time and/or the length of time the query probe remains bound to the nucleic acid during each binding event and the length of time the query probe remains unbound to the nucleic acid between each binding event (e.g., the "dwell times" in the bound and unbound states, respectively) are determined, e.g., by the use of a computer and software (e.g., to analyze the data using a hidden Markov model and Poisson statistics).

In some embodiments, control samples are measured (e.g., in absence of target). Fluorescence detected in a control sample is "background fluorescence" or "background (fluorescence) intensity" or "baseline".

In some embodiments, data comprising measurements of fluorescence intensity at the emission wavelength of the query probe are recorded as a function of time. In some embodiments, the number of binding events and the dwell times of binding events (e.g. for each immobilized nucleic acid) are determined from the data (e.g., by determining the number of times and the lengths of time the fluorescence intensity is above a threshold background fluorescence intensity). In some embodiments, transitions (e.g., binding and dissociation of a query probe) are counted for each discrete location on the solid support where a target nucleic acid is immobilized. In some embodiments, a threshold number of transitions is used to discriminate the presence of a target nucleic acid at a discrete location on the solid support from background signal, non-target nucleic acid, and/or spurious binding of the query probe. In some embodiments, a number of transitions greater than 10 recorded during the acquisition time indicates the presence of a target nucleic acid at the discrete location on the solid support.

In some embodiments, a distribution of the number of transitions for each immobilized target is determined—e.g., the number of transitions is counted for each immobilized nucleic acid target observed. In some embodiments a histogram is produced. In some embodiments, characteristic parameters of the distribution are determined, e.g., the mean, median, peak, shape, etc. of the distribution are determined. In some embodiments, the distribution produced from a target nucleic acid is significantly different than a distribution produced from a non-target nucleic acid or the distribution produced in the absence of a target nucleic acid. In some embodiments, a mean number of transitions is determined for the plurality of immobilized target nucleic acids. In some embodiments, the mean number of transitions observed for a sample comprising a target nucleic acid is approximately linearly related as a function of time and has a positive slope (e.g., the mean number of transitions increases approximately linearly as a function of time).

In some embodiments, the data are treated using statistics (e.g., Poisson statistics) to determine the probability of a transition occurring as a function of time at each discrete location on the solid support. In some particular embodiments, a relatively constant probability of a transition event occurring as a function of time at a discrete location on the solid support indicates the presence of a target nucleic acid at said discrete location on the solid support. In some embodiments, a correlation coefficient relating event number and elapsed time is calculated from the probability of a transition event occurring as a function of time at a discrete location on the solid support. In some embodiments, a correlation coefficient relating event number and elapsed time greater than 0.95 when calculated from the probability of a transition event occurring as a function of time at a discrete location on the solid support indicates the presence of a target nucleic acid at said discrete location on the solid support.

In some embodiments, dwell times of bound query probe ($\tau_{on}$) and unbound query probe ($\tau_{off}$) are used to identify the presence of a target nucleic acid in a sample and/or to distinguish a sample comprising a target nucleic acid from a sample comprising a non-target nucleic acid and/or not comprising the target nucleic acid. For example, the $\tau_{on}$ for a target nucleic acid is greater than the $\tau_{on}$ for a non-target nucleic acid; and, the $\tau_{off}$ for a target nucleic acid is smaller than the $\tau_{off}$ for a non-target nucleic acid. In some embodiments, measuring $\tau_{on}$ and $\tau_{off}$ for a negative control and for a sample indicates the presence or absence of the target nucleic acid in the sample. In some embodiments, a plurality of $\tau_{on}$ and $\tau_{off}$ values is determined for each of a plurality of spots imaged on a solid support, e.g., for a control (e.g., positive and/or negative control) and a sample suspected of comprising a target nucleic acid. In some embodiments, a mean $\tau_{on}$ and/or $\tau_{off}$ is determined for each of a plurality of spots imaged on a solid support, e.g., for a control (e.g., positive and/or negative control) and a sample suspected of comprising a target nucleic acid. In some embodiments, a plot of $\tau_{on}$ versus $\tau_{off}$ (e.g., mean $\tau_{on}$ and $\tau_{off}$, time-averaged $\tau_{on}$ and $\tau_{off}$, etc.) for all imaged spots indicates the presence or absence of the target nucleic acid in the sample.

For instance, an exemplary embodiment of the methods according to the technology provided comprises the following steps:

1. Slide Preparation and Sample Addition
    A. Passivate the surface of a microscope slide or coverslip to prevent nonspecific binding, while providing functionalization for the immobilization of capture probes to the solid support (e.g., providing biotin groups on the surface for streptavidin-mediated coupling of capture probes to the surface).
        i. Covalently modify the surface, e.g., with poly(ethylene glycol) and biotinyl poly(ethylene glycol). See, e.g., Abelson, J. et al. "Conformational dynamics of single pre-mRNA molecules during in vitro splicing." Nat. Struct. Mol. Biol. 17, 504-512 (2010).
  a. Clean a quartz or glass microscope slide or coverslip, e.g., with strong base (ammonium hydroxide) and hydrogen peroxide, e.g., to remove fluorescent impurities and prepare the glass surface for covalent modification.
  b. Covalently functionalize the glass surface, e.g., with an aminosilane (e.g., (3-aminopropyl)triethoxysilane). Rinse thoroughly with deionized water and dry under a stream of air or nitrogen.
  c. Passivate the surface, e.g., to minimize nonspecific binding of probes, RNA, and other biomolecules (e.g., proteins) to the surface. Further modify the aminosilane surface with a 1:10 mixture of succinimidyl ester conjugates of poly(ethylene glycol) and biotinylated poly(ethylene glycol). Rinse thoroughly with deionized water and dry under a stream of air or nitrogen.
  d. Quench unreacted amino groups on the surface, e.g., with a succinimidyl ester such as disulfosuccinimidyl tartrate. Rinse thoroughly with deionized water. Rinse thoroughly with deionized water and dry under a stream of air or nitrogen.
 ii. Alternatively, in some embodiments, one of skill in the art can noncovalently modify the surface according to techniques known in the art, e.g., as follows:
  a. Incubate a bare glass slide with >1 mg/mL of biotinylated bovine serum albumin.
  b. Flush out the excess biotinylated bovine serum albumin using a near-neutral pH buffer.
 iii. Alternatively, some embodiments comprise use of a commercially prepared biotin-conjugated microscope slide or coverslip, or a slide incorporating a zero-mode waveguide array.
B. Incubate the surface with a saturating concentration of streptavidin, avidin, and/or neutravidin, which binds to the biotin groups on a fraction of the surface poly(ethylene glycol) molecules and provides additional binding sites for a biotinylated capture probe. Wash away excess unbound protein with a near neutral pH buffer (we use T50=10 mM Tris-HCl, 50 mM NaCl, 1 mM EDTA, pH 8.0).
C. Incubate the surface with a saturating concentration of biotinylated capture probe(s) for the nucleic acid (e.g., miRNA) target(s) of interest. Wash away excess unbound probe with a near neutral pH buffer (e.g., 1x phosphate-buffered saline, or PBS).
D. Incubate the surface with a solution containing the target nucleic acids (e.g., miRNA(s)) to be quantified. Incubate until binding reaction reaches completion.
E. Replace sample with imaging buffer containing oxygen scavenger system (OSS) and the fluorescent probe(s) of interest, e.g., 4×PBS as the buffer and an OSS comprising 25 nM protocatechuate dioxygenase, 2.5 mM protocatechuate, and 1 mM Trolox. In some embodiments, the fluorescent probe concentration is approximately 1 nM to 1 µM (e.g., approximately 25 nM) depending on the illumination configuration of the microscope, the speed and sensitivity of the detector, and the kinetics of probe binding and dissociation.

2. Fluorescence Microscopy
A. Mount the microscope slide on a fluorescence microscope, e.g., a microscope configured to provide one of the following illumination configurations, e.g., to minimize or eliminate background signal from freely diffusing (e.g., not bound to the surface or surface-bound targets) fluorescent query probes:
  i. Prism-type total internal reflection fluorescence (TIRF)
  ii. Objective-type TIRF
  iii. Near-TIRF or HiLo
  iv. Confocal laser scanning
  v. Zero-mode waveguide
  vi. Other illumination configurations capable of parallel monitoring of a large area of a slide or a coverslip (>100 pmt) while restricting illumination to a small region of space near the surface.
B. Illuminate the surface with light of an appropriate wavelength and sufficient intensity to excite and reliably detect an individual surface-bound fluorescent query probe, but not so intense that the probe photobleaches before its binding can be observed and counted.
C. Using appropriate optics (chromatic filters, dichroic mirrors, etc.), isolate the emission signal of the fluorescent query probe from other background signal, monitor the fluorescence emission of the probe near the surface (that is, within several tens or hundreds of nanometers) using an appropriate detector, e.g:
  i. Intensified charge coupled device (ICCD)
  ii. Electron-multiplying charge coupled device (EM-CCD)
  iii. Complementary metal-oxide-semiconductor (CMOS)
  iv. Photomultiplier tube (PMT)
  v. Avalanche photodiode (APD)
  vi. Other detectors capable of detecting fluorescence emission from single chromophores.
D. Collect fluorescence emission continuously for a period of time having sufficient temporal resolution to allow observation of several consecutive binding and dissociation events of fluorescent query probes to a typical surface-bound nucleic acid target (e.g., miRNA). During experiments conducted during the development of embodiments of the technology provided herein, a typical temporal resolution was 0.5 seconds and the length of observation was 10 minutes)

3. Data Processing and Interpretation
A. Within the movie resulting from fluorescence microscopy, locate the regions of the image in which binding events of fluorescent probes are observed. These are "candidate targets" or "candidates."
  i. Generate an intensity or fluctuation map to locate the sites of probe binding with high signal-to-noise.
    a. Intensity map: for each pixel in the movie frame, calculate the mean fluorescence intensity over a specified time interval comprising a significant fraction (e.g., from 10-100%) of the movie.
    b. Fluctuation map: for each pixel in the movie frame, calculate the mean absolute frame-to-frame difference in intensity over a specified time interval comprising a significant fraction (e.g., from 10-100%) of the movie.
  ii. Within the intensity or fluctuation map, search for locally maximal intensity values. Filter out those maxima resulting from noise or uneven background using an empirically determined noise threshold. The remaining local maxima represent sites of fluorescent probe binding.

B. For each candidate identified in step (A), calculate the intensity of fluorescent signal as a function of time. This is the "intensity trace" of the corresponding candidate.
   i. Identify a square (e.g., 5 pixel×5 pixel) region, centered on the local intensity maximum, that encompasses the vast majority of the fluorescent signal emitted from a single fluorescent probe (determined by the point-spread function of the microscope) while excluding as much nearby fluorescent signal (e.g., from nearby surface-bound probes) as possible.
   ii. For each frame in the movie, calculate the total intensity of the square region identified in (i), correcting for the local background intensity. Local background is calculated, for example, as the median intensity value of the pixels immediately adjacent to the square region under analysis.
C. For each intensity trace, determine the number of times a fluorescent probe binds or dissociates throughout the course of the movie. This value is the number of transitions N
   i. Using hidden Markov modeling software such as QuB, vbFRET, or HaMMy, calculate an idealized (noise-free) two-state intensity trace that identifies transitions between high and low intensity (e.g., binding and dissociation events) for each candidate.
   ii. In some embodiments, methods comprise use of an edge detection algorithm to determine the number of transitions between high and low intensity within each intensity trace. See, e.g., Canny, J. 1986. A computational approach to edge detection. IEEE Trans. Pattern Anal. Mach. Intell. 8, 6 (November 1986), 679-698.
   iii. Identify and distinguish targets from spurious candidates as follows:
      a. Exclude candidates whose intensity transitions are smaller than an empirically determined threshold. For example, in some embodiments the threshold is chosen to exclude background noise and fluctuations but to include a majority of fluorescent query probes, which will exhibit slight variations in intensity depending on the homogeneity of illumination across the field of view.
      b. Exclude candidates whose signal-to-noise is lower than an empirically determined threshold. The signal-to-noise is calculated as the difference in intensity between the probe-bound and unbound states, divided by the standard deviation of the signal in the unbound state.
      c. Exclude candidates whose median dwell time in the high-intensity ("probe-bound") or low-intensity ("unbound") state is shorter than a specified value. This serves to distinguish genuine probe binding events to the target from brief, but repetitive, nonspecific binding events to the slide surface, or rapid blinking of surface-bound fluorescent probes.
      d. Exclude candidates exhibiting a number of transitions (N) smaller than a threshold number of transitions, $N_{min}$. The value $N_{min}$ is determined using negative control experiments in which the target analyte is omitted, resulting in purely non-specific binding of the surface. Specifically, in some embodiments, $N_{min}$ excludes the vast majority of spurious background candidates while including the vast majority of true target molecules in a positive experiment. In some embodiments, $N_{min}$ is calculated as a given number of standard deviations above the mean number of transitions in a background experiment (e.g., 6 standard deviations above the mean value of N in a set of negative control experiments).
      e. Optionally: include only candidates exhibiting median or mean dwell times in the probe-bound or unbound states that are within a certain range of values that distinguish the target from related, but spurious targets, such as single-nucleotide mutants.
D. Count the number of target molecules that pass the filtering described above within one or several fields of view. This is $N_{accept}$.
E. To determine the target concentration, compare $N_{accept}$ to a standard curve prepared by using the assay to quantify a set of known concentrations of target(s) (see, e.g., FIG. 2D).

Multiplex Assays

Some embodiments are related to multiplex assays. For example, some embodiments are related to detecting more than one target nucleic acid (e.g., two or more target nucleic acids comprising different nucleotide sequences). In some embodiments, the two or more nucleic acids comprising different nucleotide sequences comprise nucleotide sequences that differ by a single nucleotide or base. In some embodiments, the two or more nucleic acids include one or more DNA and/or one or more RNA (e.g., a miRNA, a mRNA, a ncRNA).

Some embodiments are related to the use of more than one query probe—e.g., two or more query probes comprising different sequences and/or comprising different detectable (e.g., fluorescent) moieties. In some embodiments comprising use of two or more detectable (e.g., fluorescent) moieties, the technology comprises use of two or more excitation light sources (e.g., to excite the fluorescent moieties of the two or more query probes) and/or use of two or more fluorescence emission detectors. In some embodiments comprising use of two or more query probes comprising the same fluorophore, the query probes are distinguishable by their kinetic fingerprints detected by the technology provided herein.

Some embodiments are related to the use of one or more capture probe—e.g., two or more capture probes comprising different sequences.

Some embodiments comprise use of more than one query probe and one capture probe and some embodiments comprise use of more than one capture probe and one query probe. Some embodiments comprise use of more than one query probe and more than one capture probe.

In particular embodiments, a multiplex assay detects two or more target nucleic acids having similar but not identical sequences (e.g., two or more DNAs, two or more RNAs, e.g., two or more miRNAs, e.g., two or more miRNA biomarkers associated with a disease such as cancer). For example, in some embodiments, the two or more target nucleic acids comprise sequences that differ at 1, 2, 3, 4, or 5 nucleotides. The two or more nucleic acids comprise a common sequence that is complementary to an immobilized capture probe and the sequence difference is in a region bound by a query probe (e.g., a region not bound by the capture probe). Thus, in some embodiments, two or more target nucleic acids are immobilized to the solid support by hybridization to the immobilized capture probes. Then, two or more query probes are added to the detection composition. In some embodiments, the two or more query probes comprise different sequences and each sequence is complementary to a query region of one of the two or more target nucleic acids. In some embodiments, the two or more query probes further each comprises a different detectable (e.g., fluorescent) moiety. In some embodiments, one, two, or more excitation light sources are used to excite the two or more fluorescent moieties and two or more fluorescence emission detectors are used to detect binding events and dwell times as described herein for each of the two or more query probes. The different emission wavelengths (e.g., spectra) are used to differentiate the binding events and dwell times of the two query probes.

In some embodiments related to multiplex assays, the technology comprises use of two or more query probes comprising the same detectable label (e.g., the same fluorophore), wherein the query probes are distinguishable by their kinetic fingerprints as detected by the technology provided herein.

In some embodiments, each query probe comprises a distinct plurality of detectable (e.g., fluorescent) moieties to provide a complex emission spectrum as an "emission barcode" associated with each query probe and that serves to identify each query probe.

In some embodiments, combinations of any two or more approaches described above are used.

Cancer Biomarkers

In some embodiments, the technology finds use in diagnosing diseases for which a differential expression of nucleic acid biomarkers (e.g., mRNAs, miRNAs) compared to healthy controls or other diseases exists. In some embodiments, the technology finds use in diagnosing diseases associated with a mutant nucleic acid. For instance, the technology is related to diagnosing a cancer, e.g., bladder cancer, brain cancer, breast cancer, colon cancer, endometrium cancer, gastrointestinal stromal cancer, glioma, head and neck cancer, kidney cancer, leukemia, liver cancer, lung cancer, lymph node cancer, melanoma, meninges cancer, ovarian cancer, pancreas cancer, prostate cancer, sarcoma, stomach cancer, testicular cancer, thyroid cancer, thymus cancer, Wilms' tumor, and/or COPD. The diagnosis may comprise determining type, rate, and/or stage of cancer. The course of the disease and the success of therapy such as chemotherapy may be monitored. The technology provides a prognosis on the survivor rate and enables one of skill in the art to determine a patient's response to a therapy such as one or more drugs.

Thus, in some embodiments, the technology relates to detecting a nucleic acid (e.g., a DNA, an RNA (e.g., a miRNA, a mRNA, a ncRNA)) associated with cancer, an amount of a nucleic acid (e.g., a DNA, an RNA (e.g., a miRNA, a mRNA, a ncRNA)) associated with cancer, a mutation in a nucleic acid (e.g., a DNA, an RNA (e.g., a miRNA, a mRNA, a ncRNA)) associated with cancer, and/or the presence or absence of a nucleic acid (e.g., a DNA, an RNA (e.g., a miRNA, a mRNA, a ncRNA)) associated with cancer. Some cancer-associated nucleic acids (e.g., a DNA, an RNA (e.g., a miRNA, a mRNA, a ncRNA)) promote the initiation and progression of cancers through, e.g., uncontrolled growth, increased invasiveness, and resistance to cell death pathways. Some cancer-associated nucleic acid (e.g., a DNA, an RNA (e.g., a miRNA, a mRNA, a ncRNA)) inhibit or decrease these cancer-associated activities.

In some embodiments, the cancer biomarker is a ncRNA. In some embodiments, the cancer biomarker is a miRNA. In some embodiments, the cancer biomarker is a miRNA from the miR-17~mir-92 cluster, e.g., the six miRNAs miR-17, miR-18a, miR-19a, miR-20a, miR-19b-1, and miR-92a-1. These miRNAs are biomarkers for cancers such as lung, breast, pancreas, and colon cancer. These miRNAs are also biomarkers for B-cell lymphoma (e.g., in particular miR-19a and miR-19b), retinoblastoma, and glioblastoma. In particular, the miR-17~mir-92 cluster is overexpressed in lung cancer and the locus encoding the miR-17~mir-92 cluster is amplified in lymphomas and solid tumors. Transcription factors that are aberrantly expressed or that have aberrant activities in cancers, such as E2F and MYC, activate the expression of the miR-17~mir-92 cluster.

miR-21 is a biomarker associated with lung and breast cancers, and with lymphoma and glioblastoma. miR-155 is associated with lung and breast cancers, and with lymphoma. miR-221 or miR-222 is associated with lung cancer and glioblastoma. let-7 acts as a tumor suppressor and it associated with lung cancer, lymphoma, gastric cancer, prostate cancer, breast cancer, and ovarian cancer. miR-34 acts as a tumor suppressor and is associated with lung cancer, lymphoma, pancreatic cancer, colon cancer, neuroblastoma, and glioblastoma. miR-15/16 acts as a tumor suppressor and is associated with chronic lymphocytic leukemia, multiple myeloma, prostate cancer, and pancreatic cancer. miR-200 acts as a tumor suppressor and is a biomarker associated with breast cancer, renal cancer, gastric cancer, and bladder cancer. miR-181 acts as a tumor suppressor and is a biomarker associated with glioma and lymphoma. miR-29 is a tumor suppressor and is a biomarker associated with chronic lymphocytic leukemia, hepatocellular carcinoma, and breast cancer. See, e.g., Stahlhut and Slack (2013) "MicroRNAs and the cancer phenotype: profiling, signatures and clinical implications" Genome Medicine 5: 111, incorporated herein by reference.

miR-21, miR-20b, miR-20a, miR-17-5p, miR-106a, miR-18a, miR-106b, miR-18b, miR-135b, miR-183, miR-421, miR-340*, miR-19a and miR-658 are all overexpressed in gastric cancer compared with adjacent non-tumorous tissue. Further, miR-21 is overexpressed in 92% of gastric cancer; and miR-106a is overexpressed in gastric carcinoma. miR-21 is overexpressed in colon cancer. miR-143, miR-145, let-7a-1, miR-16, miR-125b, miR-31, miR-133b, miR-96, and miR-14531 are significantly downregulated in colorectal cancers. The tumour suppressor miRNA, miR-34a, is lower in human CRC tissue. miR-196a, miR-196b, miR-301, miR-155, miR-221, and miR-376a are increased and miR-217, miR-345, miR-139, and miR-142-P are decreased in pancreatic ductal adenocarcinoma (PDAC). miR-196a, miR-190, miR-186, miR-221, miR-222, miR-200b, miR-15b, and miR-95, are upregulated in pancreatic cancer. miR-25 and miR-223 are biomarkers for NSCLC. miR-485-5p, miR-361-3p, miR-326, and miR-487b are specific biomarkers for CRC. miR-221/222 are biomarkers for papillary thyroid cancer. See, e.g., Paranjape, et al (2009) "MicroRNAs: tools for cancer diagnostics" Gut 58(11): 1546, incorporated herein by reference.

Further, an increase in hsa-miR-141 (e.g., an increase in the hsa-miR-141 concentration in blood serum or plasma) is associated with prostate cancer. See, e.g., Mitchell et al. (2008) Proc Natl. Acad. Sci. U.S.A. 105(30). Accordingly, hsa-miR-141 provides a biomarker (e.g., available in blood (e.g., serum)) for prostate cancer diagnosis.

Table 1 provides a list of miRNA biomarkers reported in published studies as associated with human cancers. The upregulation or downregulation of the biomarker in the cancer is indicated in the column labeled "profile". See Xie et al (2013) "miRCancer: a microRNA-cancer association database constructed by text mining on literature" Bioinformatics 29(5): 638, incorporated herein by reference.

TABLE 1 miRNA biomarkers of human cancers

| miRNA | cancer | profile |
|---|---|---|
| hsa-let-7a | breast cancer | down |
| hsa-let-7a | colorectal cancer | down |
| hsa-let-7a | gastric cancer | down |
| hsa-let-7a | glioma | down |
| hsa-let-7a | nasopharyngeal carcinoma | down |
| hsa-let-7a | non-small cell lung cancer | down |
| hsa-let-7a | renal cell carcinoma | down |
| hsa-let-7a-1 | bronchioloalveolar carcinoma | down |
| hsa-let-7a-1 | colon cancer | down |
| hsa-let-7a-1 | esophageal squamous cell carcinoma | down |
| hsa-let-7a-1 | hepatocellular carcinoma | down |
| hsa-let-7a-1 | lung cancer | down |
| hsa-let-7a-1 | nasopharyngeal carcinoma | down |
| hsa-let-7a-1 | neuroblastoma | down |
| hsa-let-7a-1 | pancreatic ductal adenocarcinoma | down |
| hsa-let-7a-2 | bronchioloalveolar carcinoma | down |
| hsa-let-7a-2 | colon cancer | down |
| hsa-let-7a-2 | esophageal squamous cell carcinoma | down |
| hsa-let-7a-2 | hepatocellular carcinoma | down |
| hsa-let-7a-2 | lung cancer | down |
| hsa-let-7a-2 | nasopharyngeal carcinoma | down |
| hsa-let-7a-2 | neuroblastoma | down |
| hsa-let-7a-2 | pancreatic ductal adenocarcinoma | down |
| hsa-let-7a-3 | bronchioloalveolar carcinoma | down |
| hsa-let-7a-3 | colon cancer | down |
| hsa-let-7a-3 | esophageal squamous cell carcinoma | down |
| hsa-let-7a-3 | hepatocellular carcinoma | down |
| hsa-let-7a-3 | lung cancer | down |
| hsa-let-7a-3 | nasopharyngeal carcinoma | down |
| hsa-let-7a-3 | neuroblastoma | down |
| hsa-let-7a-3 | pancreatic ductal adenocarcinoma | down |
| hsa-let-7a-3p | prostate cancer | down |
| hsa-let-7b | acute lymphoblastic leukemia | down |
| hsa-let-7b | breast cancer | down |
| hsa-let-7b | bronchioloalveolar carcinoma | down |
| hsa-let-7b | colon cancer | down |
| hsa-let-7b | esophageal squamous cell carcinoma | down |
| hsa-let-7b | hepatocellular carcinoma | down |
| hsa-let-7b | lung cancer | down |
| hsa-let-7b | malignant melanoma | down |
| hsa-let-7b | nasopharyngeal carcinoma | down |
| hsa-let-7b | neuroblastoma | down |
| hsa-let-7b | pancreatic ductal adenocarcinoma | down |
| hsa-let-7c | acute myeloid leukemia | down |
| hsa-let-7c | acute promyelocytic leukemia | down |
| hsa-let-7c | bronchioloalveolar carcinoma | down |
| hsa-let-7c | colon cancer | down |
| hsa-let-7c | esophageal squamous cell carcinoma | down |
| hsa-let-7c | hepatocellular carcinoma | down |
| hsa-let-7c | lung cancer | down |
| hsa-let-7c | nasopharyngeal carcinoma | down |
| hsa-let-7c | neuroblastoma | down |
| hsa-let-7c | non-small cell lung cancer | down |
| hsa-let-7c | pancreatic ductal adenocarcinoma | down |
| hsa-let-7c | prostate cancer | down |
| hsa-let-7d | bronchioloalveolar carcinoma | down |
| hsa-let-7d | colon cancer | down |
| hsa-let-7d | esophageal squamous cell carcinoma | down |
| hsa-let-7d | head and neck squamous cell carcinoma | down |
| hsa-let-7d | hepatocellular carcinoma | down |
| hsa-let-7d | lung cancer | down |
| hsa-let-7d | nasopharyngeal carcinoma | down |
| hsa-let-7d | neuroblastoma | down |
| hsa-let-7d | oral cancer | down |
| hsa-let-7d | pancreatic ductal adenocarcinoma | down |
| hsa-let-7e | bronchioloalveolar carcinoma | down |
| hsa-let-7e | colon cancer | down |
| hsa-let-7e | esophageal squamous cell carcinoma | down |
| hsa-let-7e | hepatocellular carcinoma | down |
| hsa-let-7e | lung cancer | down |
| hsa-let-7e | nasopharyngeal carcinoma | down |
| hsa-let-7e | neuroblastoma | down |
| hsa-let-7e | pancreatic ductal adenocarcinoma | down |
| hsa-let-7e | papillary thyroid carcinoma | up |
| hsa-let-7f-1 | bronchioloalveolar carcinoma | down |
| hsa-let-7f-1 | colon cancer | down |
| hsa-let-7f-1 | esophageal squamous cell carcinoma | down |
| hsa-let-7f-1 | hepatocellular carcinoma | down |
| hsa-let-7f-1 | lung cancer | down |
| hsa-let-7f-1 | nasopharyngeal carcinoma | down |
| hsa-let-7f-1 | neuroblastoma | down |
| hsa-let-7f-1 | pancreatic ductal adenocarcinoma | down |
| hsa-let-7f-2 | bronchioloalveolar carcinoma | down |
| hsa-let-7f-2 | colon cancer | down |
| hsa-let-7f-2 | esophageal squamous cell carcinoma | down |
| hsa-let-7f-2 | hepatocellular carcinoma | down |
| hsa-let-7f-2 | lung cancer | down |
| hsa-let-7f-2 | nasopharyngeal carcinoma | down |
| hsa-let-7f-2 | neuroblastoma | down |
| hsa-let-7f-2 | pancreatic ductal adenocarcinoma | down |
| hsa-let-7g | breast cancer | down |
| hsa-let-7g | bronchioloalveolar carcinoma | down |
| hsa-let-7g | colon cancer | down |
| hsa-let-7g | esophageal squamous cell carcinoma | down |
| hsa-let-7g | hepatocellular carcinoma | down |
| hsa-let-7g | lung cancer | down |
| hsa-let-7g | nasopharyngeal carcinoma | down |
| hsa-let-7g | neuroblastoma | down |
| hsa-let-7g | pancreatic ductal adenocarcinoma | down |
| hsa-let-7i | bronchioloalveolar carcinoma | down |
| hsa-let-7i | colon cancer | down |
| hsa-let-7i | esophageal squamous cell carcinoma | down |
| hsa-let-7i | hepatocellular carcinoma | down |
| hsa-let-7i | lung cancer | down |
| hsa-let-7i | nasopharyngeal carcinoma | down |
| hsa-let-7i | neuroblastoma | down |
| hsa-let-7i | ovarian cancer | down |
| hsa-let-7i | pancreatic ductal adenocarcinoma | down |
| hsa-mir-1 | head and neck squamous cell carcinoma | down |
| hsa-mir-1 | hepatocellular carcinoma | down |
| hsa-mir-1 | lung cancer | down |
| hsa-mir-1 | non-small cell lung cancer | down |
| hsa-mir-1 | renal cell carcinoma | down |
| hsa-mir-1 | bladder cancer | down |
| hsa-mir-100 | breast cancer | down |
| hsa-mir-100 | cervical carcinoma | down |
| hsa-mir-100 | esophageal squamous cell carcinoma | down |
| hsa-mir-100 | gastric cancer | up |
| hsa-mir-100 | glioblastoma | down |
| hsa-mir-100 | hepatocellular carcinoma | down |
| hsa-mir-100 | mesenchymal cancer | down |
| hsa-mir-100 | non-small cell lung cancer | down |
| hsa-mir-100 | oral squamous cell carcinoma | down |
| hsa-mir-100 | osteosarcoma | down |
| hsa-mir-100 | ovarian cancer | down |
| hsa-mir-100 | ovarian carcinoma | down |
| hsa-mir-100 | renal cell carcinoma | up |
| hsa-mir-101 | bladder cancer | down |
| hsa-mir-101 | cervical carcinoma | down |
| hsa-mir-101 | cholangiocarcinoma | down |
| hsa-mir-101 | colon cancer | down |
| hsa-mir-101 | gastric cancer | down |
| hsa-mir-101 | glioblastoma | down |
| hsa-mir-101 | hepatocellular carcinoma | down |
| hsa-mir-101 | liver cancer | down |
| hsa-mir-101 | lung cancer | down |
| hsa-mir-101 | malignant melanoma | down |
| hsa-mir-101 | non-small cell lung cancer | down |
| hsa-mir-101 | prostate cancer | down |
| hsa-mir-103 | gastric cancer | up |
| hsa-mir-103 | colorectal cancer | up |
| hsa-mir-103a-3p | bladder cancer | up |
| hsa-mir-105 | prostate cancer | down |
| hsa-mir-106a | cervical squamous cell carcinoma | down |
| hsa-mir-106a | colorectal cancer | up |
| hsa-mir-106a | endometrial cancer | up |
| hsa-mir-106a | gastric cancer | up |
| hsa-mir-106a | glioblastoma | down |

TABLE 1-continued miRNA biomarkers of human cancers

| miRNA | cancer | profile |
|---|---|---|
| hsa-mir-106a | glioma | down |
| hsa-mir-106a | non-small cell lung cancer | down |
| hsa-mir-106a | ovarian cancer | up |
| hsa-mir-106b | gastric cancer | up |
| hsa-mir-106b | glioma | up |
| hsa-mir-106b | head and neck squamous cell carcinoma | up |
| hsa-mir-106b | hepatocellular carcinoma | up |
| hsa-mir-106b | laryngeal carcinoma | up |
| hsa-mir-106b-5p | glioma | up |
| hsa-mir-107 | acute promyelocytic leukemia | down |
| hsa-mir-107 | breast cancer | down |
| hsa-mir-107 | gastric cancer | up |
| hsa-mir-107 | glioma | down |
| hsa-mir-107 | head and neck squamous cell carcinoma | down |
| hsa-mir-107 | prostate carcinoma | down |
| hsa-mir-10a | chronic myelogenous leukemia | down |
| hsa-mir-10a | gastric cancer | down |
| hsa-mir-10a | pancreatic cancer | up |
| hsa-mir-10a | cervical cancer | up |
| hsa-mir-10b | bladder cancer | up |
| hsa-mir-10b | breast cancer | down |
| hsa-mir-10b | esophageal cancer | up |
| hsa-mir-10b | gastric cancer | up |
| hsa-mir-10b | gastric cancer | down |
| hsa-mir-10b | glioblastoma | up |
| hsa-mir-10b | glioma | up |
| hsa-mir-10b | hepatocellular carcinoma | up |
| hsa-mir-10b | nasopharyngeal carcinoma | up |
| hsa-mir-10b | oral cancer | up |
| hsa-mir-10b | pancreatic cancer | up |
| hsa-mir-10b | pancreatic ductal adenocarcinoma | up |
| hsa-mir-1179 | colorectal cancer | up |
| hsa-mir-1207-5p | gastric cancer | down |
| hsa-mir-122 | breast cancer | down |
| hsa-mir-122 | gastric cancer | down |
| hsa-mir-122 | hepatocellular carcinoma | down |
| hsa-mir-122 | hepatocellular carcinoma | up |
| hsa-mir-122 | liver cancer | down |
| hsa-mir-122 | pituitary carcinoma | up |
| hsa-mir-122 | renal clear cell carcinoma | up |
| hsa-mir-1228* | gastric cancer | down |
| hsa-mir-122a | hepatocellular carcinoma | down |
| hsa-mir-122a | gastrointestinal cancer | down |
| hsa-mir-1233 | renal cell carcinoma | up |
| hsa-mir-124 | anaplastic astrocytoma | down |
| hsa-mir-124 | breast cancer | down |
| hsa-mir-124 | cervical squamous cell carcinoma | down |
| hsa-mir-124 | colorectal cancer | down |
| hsa-mir-124 | gastric cancer | down |
| hsa-mir-124 | glioblastoma | down |
| hsa-mir-124 | glioma | down |
| hsa-mir-124 | hepatocellular carcinoma | down |
| hsa-mir-124 | medulloblastoma | down |
| hsa-mir-124 | neuroblastoma | down |
| hsa-mir-124 | oral squamous cell carcinoma | down |
| hsa-mir-124 | ovarian cancer | down |
| hsa-mir-124 | pancreatic cancer | down |
| hsa-mir-124-3p | bladder cancer | down |
| hsa-mir-124-5p | glioma | down |
| hsa-mir-1247 | pancreatic cancer | down |
| hsa-mir-124a | glioblastoma | down |
| hsa-mir-124a | mantle cell lymphoma | up |
| hsa-mir-124a | acute lymphoblastic leukemia | down |
| hsa-mir-1258 | breast cancer | down |
| hsa-mir-1259 | gastric cancer | up |
| hsa-mir-125a | glioblastoma | down |
| hsa-mir-125a | colorectal cancer | down |
| hsa-mir-125a-3p | non-small cell lung cancer | down |
| hsa-mir-125a-3p | gastric cancer | down |
| hsa-mir-125a-5p | non-small cell lung cancer | down |
| hsa-mir-125a-5p | breast cancer | down |
| hsa-mir-125b | acute myeloid leukemia | up |
| hsa-mir-125b | bladder cancer | down |
| hsa-mir-125b | breast cancer | down |
| hsa-mir-125b | chronic lymphocytic leukemia | down |
| hsa-mir-125b | follicular cancer | up |
| hsa-mir-125b | gastric cancer | up |
| hsa-mir-125b | glioblastoma | down |
| hsa-mir-125b | glioblastoma | up |
| hsa-mir-125b | glioma | up |
| hsa-mir-125b | hepatocellular carcinoma | down |
| hsa-mir-125b | malignant melanoma | down |
| hsa-mir-125b | neuroblastoma | up |
| hsa-mir-125b | oral squamous cell carcinoma | down |
| hsa-mir-125b | osteosarcoma | down |
| hsa-mir-125b | ovarian cancer | down |
| hsa-mir-125b | prostate cancer | up |
| hsa-mir-125b-1-3p | mesenchymal cancer | up |
| hsa-mir-125b-2* | colorectal cancer | up |
| hsa-mir-126 | breast cancer | down |
| hsa-mir-126 | colon cancer | down |
| hsa-mir-126 | colorectal cancer | down |
| hsa-mir-126 | gastric cancer | down |
| hsa-mir-126 | gastric cancer | up |
| hsa-mir-126 | hepatocellular carcinoma | down |
| hsa-mir-126 | malignant melanoma | up |
| hsa-mir-126 | malignant mesothelioma | down |
| hsa-mir-126 | non-small cell lung cancer | down |
| hsa-mir-126 | oral squamous cell carcinoma | up |
| hsa-mir-126 | osteosarcoma | down |
| hsa-mir-126 | pancreatic ductal adenocarcinoma | down |
| hsa-mir-126 | small cell lung cancer | down |
| hsa-mir-126* | non-small cell lung cancer | down |
| hsa-mir-1260b | renal cell carcinoma | up |
| hsa-mir-1266 | gastric cancer | down |
| hsa-mir-127 | breast cancer | down |
| hsa-mir-127 | gastric cancer | down |
| hsa-mir-127 | hepatocellular carcinoma | down |
| hsa-mir-127-3p | osteosarcoma | down |
| hsa-mir-127-3p | glioblastoma | down |
| hsa-mir-1271 | hepatocellular carcinoma | down |
| hsa-mir-128 | acute lymphoblastic leukemia | up |
| hsa-mir-128 | acute myeloid leukemia | up |
| hsa-mir-128 | glioblastoma | down |
| hsa-mir-128 | glioma | down |
| hsa-mir-128 | osteosarcoma | up |
| hsa-mir-128 | prostate cancer | down |
| hsa-mir-1280 | bladder cancer | down |
| hsa-mir-1285 | renal cell carcinoma | down |
| hsa-mir-128a | medulloblastoma | down |
| hsa-mir-129 | colorectal cancer | down |
| hsa-mir-129 | glioblastoma | down |
| hsa-mir-129 | breast cancer | down |
| hsa-mir-129-1-3p | gastric cancer | down |
| hsa-mir-129-2-3p | gastric cancer | down |
| hsa-mir-129-3p | gastric cancer | down |
| hsa-mir-129-5p | laryngeal squamous cell carcinoma | down |
| hsa-mir-129-5p | gastric cancer | down |
| hsa-mir-1290 | colon cancer | up |
| hsa-mir-1291 | renal cell carcinoma | down |
| hsa-mir-1296 | prostate cancer | down |
| hsa-mir-1297 | lung adenocarcinoma | down |
| hsa-mir-130a | hepatocellular carcinoma | up |
| hsa-mir-130b | colorectal cancer | down |
| hsa-mir-130b | colorectal cancer | up |
| hsa-mir-130b | hepatocellular carcinoma | up |
| hsa-mir-130b | ovarian cancer | down |
| hsa-mir-130b | papillary thyroid carcinoma | down |
| hsa-mir-130b* | gastric cancer | up |
| hsa-mir-132 | osteosarcoma | down |
| hsa-mir-132 | pancreatic cancer | up |
| hsa-mir-132 | pancreatic carcinoma | down |
| hsa-mir-133a | bladder cancer | down |
| hsa-mir-133a | breast cancer | down |
| hsa-mir-133a | colorectal cancer | down |
| hsa-mir-133a | esophageal squamous cell carcinoma | down |
| hsa-mir-133a | head and neck squamous cell carcinoma | down |
| hsa-mir-133a | lung squamous cell carcinoma | down |
| hsa-mir-133a | osteosarcoma | down |
| hsa-mir-133a | ovarian cancer | down |
| hsa-mir-133a | renal cell carcinoma | down |
| hsa-mir-133a-1 | prostate cancer | down |

TABLE 1-continued miRNA biomarkers of human cancers

| miRNA | cancer | profile |
|---|---|---|
| hsa-mir-133a-2 | prostate cancer | down |
| hsa-mir-133b | bladder cancer | down |
| hsa-mir-133b | cervical carcinoma | up |
| hsa-mir-133b | colorectal cancer | up |
| hsa-mir-133b | colorectal cancer | down |
| hsa-mir-133b | esophageal squamous cell carcinoma | down |
| hsa-mir-133b | gastric cancer | down |
| hsa-mir-133b | lung cancer | down |
| hsa-mir-133b | prostate cancer | down |
| hsa-mir-134 | hepatocellular carcinoma | down |
| hsa-mir-134 | head and neck squamous cell carcinoma | up |
| hsa-mir-135a | breast cancer | up |
| hsa-mir-135a | colorectal cancer | up |
| hsa-mir-135a | renal cell carcinoma | down |
| hsa-mir-135a-1 | colorectal cancer | up |
| hsa-mir-135a-2 | colorectal cancer | up |
| hsa-mir-135b | colorectal cancer | up |
| hsa-mir-135b | gastric cancer | up |
| hsa-mir-135b | lung cancer | up |
| hsa-mir-136 | glioma | down |
| hsa-mir-136 | non-small cell lung cancer | up |
| hsa-mir-136 | glioblastoma | down |
| hsa-mir-137 | anaplastic astrocytoma | down |
| hsa-mir-137 | colorectal cancer | down |
| hsa-mir-137 | gastric cancer | down |
| hsa-mir-137 | glioblastoma | down |
| hsa-mir-137 | neuroblastoma | down |
| hsa-mir-137 | ovarian cancer | down |
| hsa-mir-137 | squamous carcinoma | up |
| hsa-mir-137 | uveal melanoma | down |
| hsa-mir-138 | anaplastic thyroid carcinoma | down |
| hsa-mir-138 | chronic myelogenous leukemia | down |
| hsa-mir-138 | colorectal cancer | down |
| hsa-mir-138 | esophageal squamous cell carcinoma | down |
| hsa-mir-138 | gastric cancer | up |
| hsa-mir-138 | head and neck squamous cell carcinoma | down |
| hsa-mir-138 | hepatocellular carcinoma | down |
| hsa-mir-138 | nasopharyngeal carcinoma | down |
| hsa-mir-138 | non-small cell lung cancer | down |
| hsa-mir-138 | ovarian cancer | down |
| hsa-mir-138 | papillary thyroid carcinoma | down |
| hsa-mir-138 | renal cell carcinoma | down |
| hsa-mir-138 | renal clear cell carcinoma | down |
| hsa-mir-139 | colorectal cancer | down |
| hsa-mir-139 | colorectal carcinoma | down |
| hsa-mir-139 | glioma | down |
| hsa-mir-139 | hepatocellular carcinoma | down |
| hsa-mir-139-3p | colorectal cancer | up |
| hsa-mir-140 | non-small cell lung cancer | down |
| hsa-mir-140 | non-small cell lung cancer | up |
| hsa-mir-140-5p | hepatocellular carcinoma | down |
| hsa-mir-140-5p | liver cancer | down |
| hsa-mir-141 | bladder cancer | up |
| hsa-mir-141 | bladder cancer | down |
| hsa-mir-141 | breast cancer | up |
| hsa-mir-141 | gastric cancer | down |
| hsa-mir-141 | hepatocellular carcinoma | down |
| hsa-mir-141 | lung adenocarcinoma | down |
| hsa-mir-141 | malignant melanoma | up |
| hsa-mir-141 | mesenchymal cancer | down |
| hsa-mir-141 | non-small cell lung cancer | up |
| hsa-mir-141 | osteosarcoma | down |
| hsa-mir-141 | ovarian cancer | down |
| hsa-mir-141 | ovarian cancer | up |
| hsa-mir-141 | pancreatic cancer | down |
| hsa-mir-141 | renal cell carcinoma | down |
| hsa-mir-141 | renal clear cell carcinoma | down |
| hsa-mir-141 | prostate cancer | up |
| hsa-mir-142-3p | acute lymphoblastic leukemia | down |
| hsa-mir-142-3p | colon cancer | down |
| hsa-mir-142-3p | hepatocellular carcinoma | down |
| hsa-mir-142-3p | mantle cell lymphoma | down |
| hsa-mir-142-3p | non-small cell lung cancer | up |
| hsa-mir-142-5p | malt lymphoma | up |
| hsa-mir-142-5p | mantle cell lymphoma | down |
| hsa-mir-142-5p | osteosarcoma | down |
| hsa-mir-142-5p | lung cancer | down |
| hsa-mir-143 | bladder cancer | down |
| hsa-mir-143 | breast cancer | down |
| hsa-mir-143 | cervical cancer | down |
| hsa-mir-143 | colon cancer | down |
| hsa-mir-143 | colorectal cancer | down |
| hsa-mir-143 | colorectal carcinoma | down |
| hsa-mir-143 | esophageal squamous cell carcinoma | down |
| hsa-mir-143 | gastric cancer | up |
| hsa-mir-143 | glioblastoma | down |
| hsa-mir-143 | glioma | down |
| hsa-mir-143 | nasopharyngeal carcinoma | down |
| hsa-mir-143 | osteosarcoma | down |
| hsa-mir-143 | prostate cancer | down |
| hsa-mir-143 | renal cell carcinoma | down |
| hsa-mir-144 | nasopharyngeal carcinoma | up |
| hsa-mir-144 | bladder cancer | down |
| hsa-mir-145 | bladder cancer | down |
| hsa-mir-145 | breast cancer | down |
| hsa-mir-145 | cervical cancer | down |
| hsa-mir-145 | colon cancer | down |
| hsa-mir-145 | colorectal cancer | down |
| hsa-mir-145 | colorectal carcinoma | down |
| hsa-mir-145 | esophageal squamous cell carcinoma | down |
| hsa-mir-145 | esophageal squamous cell carcinoma | up |
| hsa-mir-145 | glioblastoma | down |
| hsa-mir-145 | glioma | down |
| hsa-mir-145 | hepatocellular carcinoma | down |
| hsa-mir-145 | kidney cancer | down |
| hsa-mir-145 | liver cancer | down |
| hsa-mir-145 | lung adenocarcinoma | down |
| hsa-mir-145 | lung cancer | down |
| hsa-mir-145 | nasopharyngeal carcinoma | down |
| hsa-mir-145 | neuroblastoma | down |
| hsa-mir-145 | non-small cell lung cancer | down |
| hsa-mir-145 | oral squamous cell carcinoma | down |
| hsa-mir-145 | osteosarcoma | down |
| hsa-mir-145 | ovarian cancer | down |
| hsa-mir-145 | primary cns lymphomas | down |
| hsa-mir-145 | prostate cancer | down |
| hsa-mir-145 | renal cell carcinoma | down |
| hsa-mir-146a | breast cancer | down |
| hsa-mir-146a | gastric cancer | down |
| hsa-mir-146a | gastric cancer | up |
| hsa-mir-146a | glioma | down |
| hsa-mir-146a | hepatocellular carcinoma | down |
| hsa-mir-146a | hepatocellular carcinoma | up |
| hsa-mir-146a | malignant melanoma | down |
| hsa-mir-146a | non-small cell lung cancer | down |
| hsa-mir-146a | oral squamous cell carcinoma | up |
| hsa-mir-146a | pancreatic cancer | down |
| hsa-mir-146a | papillary thyroid carcinoma | down |
| hsa-mir-146a | prostate cancer | down |
| hsa-mir-146a | renal cell carcinoma | up |
| hsa-mir-146b | anaplastic thyroid carcinoma | up |
| hsa-mir-146b | breast cancer | down |
| hsa-mir-146b | esophageal cancer | up |
| hsa-mir-146b | glioma | down |
| hsa-mir-146b | malignant melanoma | down |
| hsa-mir-146b | non-small cell lung cancer | down |
| hsa-mir-146b | oral squamous cell carcinoma | up |
| hsa-mir-146b | papillary thyroid carcinoma | up |
| hsa-mir-146b | primary thyroid lymphoma | up |
| hsa-mir-146b | renal cell carcinoma | up |
| hsa-mir-146b-5p | glioma | down |
| hsa-mir-146b-5p | papillary thyroid carcinoma | up |
| hsa-mir-146b-5p | glioblastoma | down |
| hsa-mir-147 | gastric cancer | up |
| hsa-mir-147 | breast cancer | down |
| hsa-mir-148a | breast cancer | down |
| hsa-mir-148a | cervical squamous cell carcinoma | down |
| hsa-mir-148a | colorectal cancer | down |
| hsa-mir-148a | gastric cancer | down |
| hsa-mir-148a | gastric cancer | up |
| hsa-mir-148a | gastrointestinal cancer | down |
| hsa-mir-148a | glioblastoma | up |

TABLE 1-continued miRNA biomarkers of human cancers

| miRNA | cancer | profile |
|---|---|---|
| hsa-mir-148a | hepatocellular carcinoma | down |
| hsa-mir-148a | non-small cell lung cancer | down |
| hsa-mir-148a | ovarian cancer | down |
| hsa-mir-148a | pancreatic cancer | down |
| hsa-mir-148a | pancreatic ductal adenocarcinoma | down |
| hsa-mir-148b | gastric cancer | down |
| hsa-mir-148b | ovarian cancer | up |
| hsa-mir-148b | ovarian carcinoma | up |
| hsa-mir-148b | pancreatic cancer | down |
| hsa-mir-148b | colorectal cancer | down |
| hsa-mir-149 | gastric cancer | down |
| hsa-mir-149 | head and neck squamous cell carcinoma | down |
| hsa-mir-149 | nasopharyngeal carcinoma | up |
| hsa-mir-149 | non-small cell lung cancer | down |
| hsa-mir-150 | chronic myelogenous leukemia | down |
| hsa-mir-150 | esophageal squamous cell carcinoma | down |
| hsa-mir-150 | gastric cancer | up |
| hsa-mir-150 | lung adenocarcinoma | up |
| hsa-mir-150 | lung cancer | up |
| hsa-mir-150 | mantle cell lymphoma | down |
| hsa-mir-150 | breast cancer | up |
| hsa-mir-150* | colorectal cancer | up |
| hsa-mir-150* | pancreatic cancer | down |
| hsa-mir-150-5p | pancreatic cancer | down |
| hsa-mir-151 | chronic myelogenous leukemia | down |
| hsa-mir-151-3p | osteosarcoma | up |
| hsa-mir-151-5p | papillary thyroid carcinoma | up |
| hsa-mir-152 | breast cancer | down |
| hsa-mir-152 | endometrial cancer | down |
| hsa-mir-152 | gastrointestinal cancer | down |
| hsa-mir-152 | glioma | down |
| hsa-mir-152 | ovarian cancer | down |
| hsa-mir-152 | pancreatic cancer | down |
| hsa-mir-153 | prostate cancer | up |
| hsa-mir-153 | glioblastoma | down |
| hsa-mir-154 | prostate cancer | down |
| hsa-mir-154 | colorectal cancer | down |
| hsa-mir-155 | bladder cancer | down |
| hsa-mir-155 | breast cancer | up |
| hsa-mir-155 | chronic lymphocytic leukemia | up |
| hsa-mir-155 | chronic myelogenous leukemia | down |
| hsa-mir-155 | clear cell renal cell cancer | up |
| hsa-mir-155 | colorectal cancer | up |
| hsa-mir-155 | cutaneous t-cell lymphoma | up |
| hsa-mir-155 | diffuse large B-cell lymphoma | up |
| hsa-mir-155 | endometrial cancer | up |
| hsa-mir-155 | gallbladder carcinoma | up |
| hsa-mir-155 | gastric cancer | down |
| hsa-mir-155 | glioma | up |
| hsa-mir-155 | hepatocellular carcinoma | up |
| hsa-mir-155 | lung adenocarcinoma | up |
| hsa-mir-155 | lung cancer | up |
| hsa-mir-155 | malignant melanoma | down |
| hsa-mir-155 | malt lymphoma | up |
| hsa-mir-155 | mantle cell lymphoma | up |
| hsa-mir-155 | nasopharyngeal carcinoma | up |
| hsa-mir-155 | non-small cell lung cancer | down |
| hsa-mir-155 | oral squamous cell carcinoma | up |
| hsa-mir-155 | ovarian cancer | down |
| hsa-mir-155 | papillary thyroid carcinoma | up |
| hsa-mir-155 | rectal cancer | up |
| hsa-mir-155 | renal clear cell carcinoma | up |
| hsa-mir-155 | squamous carcinoma | up |
| hsa-mir-15a | breast cancer | down |
| hsa-mir-15a | chronic lymphocytic leukemia | down |
| hsa-mir-15a | colorectal cancer | down |
| hsa-mir-15a | lung cancer | down |
| hsa-mir-15a | neuroblastoma | up |
| hsa-mir-15a | pancreatic cancer | down |
| hsa-mir-15a | pancreatic cancer | up |
| hsa-mir-15a | pancreatic ductal adenocarcinoma | down |
| hsa-mir-15a | squamous carcinoma | down |
| hsa-mir-15b | chronic lymphocytic leukemia | down |
| hsa-mir-15b | colorectal cancer | down |
| hsa-mir-15b | glioma | down |
| hsa-mir-15b | hepatocellular carcinoma | down |
| hsa-mir-15b | lung cancer | down |
| hsa-mir-15b | malignant melanoma | up |
| hsa-mir-15b | neuroblastoma | up |
| hsa-mir-15b | tongue cancer | down |
| hsa-mir-16 | bladder cancer | down |
| hsa-mir-16 | breast cancer | down |
| hsa-mir-16 | chronic lymphocytic leukemia | down |
| hsa-mir-16 | colorectal cancer | down |
| hsa-mir-16 | esophageal squamous cell carcinoma | up |
| hsa-mir-16 | glioma | down |
| hsa-mir-16 | head and neck squamous cell carcinoma | up |
| hsa-mir-16 | hepatocellular carcinoma | down |
| hsa-mir-16 | laryngeal carcinoma | up |
| hsa-mir-16 | non-small cell lung cancer | down |
| hsa-mir-16 | osteosarcoma | down |
| hsa-mir-16 | pancreatic ductal adenocarcinoma | down |
| hsa-mir-16 | papillary thyroid carcinoma | down |
| hsa-mir-16 | squamous carcinoma | down |
| hsa-mir-16-1 | chronic lymphocytic leukemia | down |
| hsa-mir-16-1 | lung cancer | down |
| hsa-mir-16-1 | neuroblastoma | up |
| hsa-mir-16-1-3p | chronic lymphocytic leukemia | down |
| hsa-mir-16-2 | chronic lymphocytic leukemia | down |
| hsa-mir-16-2 | lung cancer | down |
| hsa-mir-16-2 | neuroblastoma | up |
| hsa-mir-17 | acute myeloid leukemia | down |
| hsa-mir-17 | b-cell lymphoma | up |
| hsa-mir-17 | breast carcinoma | up |
| hsa-mir-17 | colorectal cancer | up |
| hsa-mir-17 | colorectal carcinoma | up |
| hsa-mir-17 | esophageal squamous cell carcinoma | up |
| hsa-mir-17 | gastric cancer | up |
| hsa-mir-17 | glioma | up |
| hsa-mir-17 | lung cancer | up |
| hsa-mir-17 | malignant melanoma | up |
| hsa-mir-17 | mantle cell lymphoma | up |
| hsa-mir-17 | medulloblastoma | up |
| hsa-mir-17 | nasopharyngeal cancer | up |
| hsa-mir-17-5p | bladder cancer | up |
| hsa-mir-17-5p | breast cancer | up |
| hsa-mir-17-5p | breast cancer | down |
| hsa-mir-17-5p | cervical cancer | down |
| hsa-mir-17-5p | gastric cancer | up |
| hsa-mir-17-5p | hepatocellular carcinoma | up |
| hsa-mir-17-5p | malignant melanoma | up |
| hsa-mir-17-5p | non-small cell lung cancer | down |
| hsa-mir-17-5p | pancreatic cancer | up |
| hsa-mir-181a | acute myeloid leukemia | down |
| hsa-mir-181a | breast cancer | down |
| hsa-mir-181a | breast cancer | up |
| hsa-mir-181a | cervical cancer | up |
| hsa-mir-181a | chronic lymphocytic leukemia | down |
| hsa-mir-181a | gastric cancer | up |
| hsa-mir-181a | glioma | down |
| hsa-mir-181a | hepatocellular carcinoma | up |
| hsa-mir-181a | oral squamous cell carcinoma | down |
| hsa-mir-181a | osteosarcoma | up |
| hsa-mir-181a | pancreatic cancer | up |
| hsa-mir-181a-1 | papillary thyroid carcinoma | up |
| hsa-mir-181a-1 | hepatocellular carcinoma | up |
| hsa-mir-181a-2 | papillary thyroid carcinoma | up |
| hsa-mir-181a-2 | hepatocellular carcinoma | up |
| hsa-mir-181a-2* | gastric cancer | up |
| hsa-mir-181a-5p | gastric cancer | up |
| hsa-mir-181b | breast cancer | up |
| hsa-mir-181b | cervical cancer | up |
| hsa-mir-181b | chronic lymphocytic leukemia | down |
| hsa-mir-181b | gastric adenocarcinoma | down |
| hsa-mir-181b | gastric cancer | down |
| hsa-mir-181b | glioma | down |
| hsa-mir-181b | hepatocellular carcinoma | up |
| hsa-mir-181b | non-small cell lung cancer | down |
| hsa-mir-181b | osteosarcoma | up |
| hsa-mir-181b | prostate cancer | up |
| hsa-mir-181b-1 | papillary thyroid carcinoma | up |
| hsa-mir-181b-1 | hepatocellular carcinoma | up |

TABLE 1-continued miRNA biomarkers of human cancers

| miRNA | cancer | profile |
|---|---|---|
| hsa-mir-181b-2 | papillary thyroid carcinoma | up |
| hsa-mir-181b-2 | hepatocellular carcinoma | up |
| hsa-mir-181c | gastric cancer | up |
| hsa-mir-181c | hepatocellular carcinoma | up |
| hsa-mir-181c | neuroblastoma | down |
| hsa-mir-181c | osteosarcoma | up |
| hsa-mir-181c | papillary thyroid carcinoma | up |
| hsa-mir-181d | glioma | down |
| hsa-mir-181d | hepatocellular carcinoma | up |
| hsa-mir-181d | papillary thyroid carcinoma | up |
| hsa-mir-182 | bladder cancer | up |
| hsa-mir-182 | breast cancer | up |
| hsa-mir-182 | colorectal cancer | up |
| hsa-mir-182 | endometrial cancer | up |
| hsa-mir-182 | gallbladder carcinoma | up |
| hsa-mir-182 | gastric adenocarcinoma | down |
| hsa-mir-182 | glioma | up |
| hsa-mir-182 | hepatocellular carcinoma | up |
| hsa-mir-182 | lung cancer | up |
| hsa-mir-182 | malignant melanoma | up |
| hsa-mir-182 | ovarian cancer | up |
| hsa-mir-182 | ovarian carcinoma | up |
| hsa-mir-182 | prostate cancer | up |
| hsa-mir-182 | uveal melanoma | down |
| hsa-mir-182-5p | prostate cancer | up |
| hsa-mir-182-5p | bladder cancer | up |
| hsa-mir-1826 | kidney cancer | down |
| hsa-mir-1826 | breast cancer | down |
| hsa-mir-183 | bladder cancer | up |
| hsa-mir-183 | breast cancer | down |
| hsa-mir-183 | colorectal cancer | up |
| hsa-mir-183 | glioma | up |
| hsa-mir-183 | hepatocellular carcinoma | up |
| hsa-mir-183 | medullary thyroid carcinoma | up |
| hsa-mir-183 | osteosarcoma | down |
| hsa-mir-183 | prostate cancer | up |
| hsa-mir-183 | retinoblastoma | down |
| hsa-mir-184 | hepatocellular carcinoma | up |
| hsa-mir-184 | malignant melanoma | down |
| hsa-mir-184 | neuroblastoma | down |
| hsa-mir-184 | glioma | down |
| hsa-mir-185 | bladder cancer | up |
| hsa-mir-185 | esophageal squamous cell carcinoma | down |
| hsa-mir-185 | gastric cancer | down |
| hsa-mir-185 | gastric cancer | up |
| hsa-mir-185 | glioma | down |
| hsa-mir-185 | malignant melanoma | down |
| hsa-mir-186 | non-small cell lung cancer | down |
| hsa-mir-186 | colon carcinoma | down |
| hsa-mir-18a | b-cell lymphoma | up |
| hsa-mir-18a | bladder cancer | down |
| hsa-mir-18a | breast carcinoma | up |
| hsa-mir-18a | colon cancer | up |
| hsa-mir-18a | colorectal cancer | up |
| hsa-mir-18a | esophageal squamous cell carcinoma | up |
| hsa-mir-18a | gastric cancer | up |
| hsa-mir-18a | lung cancer | up |
| hsa-mir-18a | malignant melanoma | up |
| hsa-mir-18a | mantle cell lymphoma | up |
| hsa-mir-18a | medulloblastoma | up |
| hsa-mir-18a | nasopharyngeal carcinoma | up |
| hsa-mir-18a | non-small cell lung cancer | up |
| hsa-mir-18a | pancreatic cancer | up |
| hsa-mir-18a | pancreatic ductal adenocarcinoma | up |
| hsa-mir-18b | malignant melanoma | down |
| hsa-mir-18b | breast cancer | up |
| hsa-mir-190b | hepatocellular carcinoma | up |
| hsa-mir-191 | breast cancer | down |
| hsa-mir-191 | breast cancer | up |
| hsa-mir-191 | colorectal cancer | down |
| hsa-mir-191 | colorectal carcinoma | up |
| hsa-mir-191 | gastric cancer | up |
| hsa-mir-191 | hepatocellular carcinoma | up |
| hsa-mir-191 | osteosarcoma | up |
| hsa-mir-192 | colon cancer | down |
| hsa-mir-192 | colorectal cancer | down |
| hsa-mir-192 | gastric cancer | up |
| hsa-mir-192 | lung cancer | down |
| hsa-mir-192 | pancreatic ductal adenocarcinoma | up |
| hsa-mir-192 | bladder cancer | down |
| hsa-mir-193a-3p | breast cancer | down |
| hsa-mir-193b | breast cancer | down |
| hsa-mir-193b | glioma | up |
| hsa-mir-193b | malignant melanoma | down |
| hsa-mir-193b | malignant melanoma | up |
| hsa-mir-193b | non-small cell lung cancer | down |
| hsa-mir-193b | primary cns lymphomas | down |
| hsa-mir-194 | lung cancer | down |
| hsa-mir-194 | pancreatic ductal adenocarcinoma | up |
| hsa-mir-194 | colorectal cancer | down |
| hsa-mir-195 | adrenal cortical carcinoma | down |
| hsa-mir-195 | bladder cancer | down |
| hsa-mir-195 | breast cancer | down |
| hsa-mir-195 | chronic lymphocytic leukemia | down |
| hsa-mir-195 | colorectal cancer | down |
| hsa-mir-195 | esophageal squamous cell carcinoma | down |
| hsa-mir-195 | gastric cancer | down |
| hsa-mir-195 | glioblastoma | down |
| hsa-mir-195 | glioma | down |
| hsa-mir-195 | hepatocellular carcinoma | down |
| hsa-mir-195 | lung cancer | down |
| hsa-mir-195 | neuroblastoma | up |
| hsa-mir-195 | non-small cell lung cancer | down |
| hsa-mir-195 | osteosarcoma | down |
| hsa-mir-196a | cervical cancer | up |
| hsa-mir-196a | colorectal cancer | down |
| hsa-mir-196a | esophageal adenocarcinoma | up |
| hsa-mir-196a | gastric cancer | up |
| hsa-mir-196a | gastrointestinal stromal tumor | up |
| hsa-mir-196a | glioblastoma | up |
| hsa-mir-196a | non-small cell lung cancer | up |
| hsa-mir-196a | pancreatic cancer | up |
| hsa-mir-196a | pancreatic ductal adenocarcinoma | up |
| hsa-mir-196a | squamous carcinoma | up |
| hsa-mir-196a* | gastric cancer | up |
| hsa-mir-196a-1 | oral squamous cell carcinoma | up |
| hsa-mir-196a-1 | glioblastoma | up |
| hsa-mir-196a-2 | oral squamous cell carcinoma | up |
| hsa-mir-196a-2 | glioblastoma | up |
| hsa-mir-196b | gastric cancer | up |
| hsa-mir-196b | glioblastoma | up |
| hsa-mir-196b | oral squamous cell carcinoma | up |
| hsa-mir-197 | gastric cancer | down |
| hsa-mir-197 | lung cancer | up |
| hsa-mir-197 | follicular thyroid carcinoma | up |
| hsa-mir-1974 | adrenal cortical carcinoma | down |
| hsa-mir-198 | lung cancer | down |
| hsa-mir-198 | pancreatic cancer | down |
| hsa-mir-198 | hepatocellular carcinoma | down |
| hsa-mir-199a | gastric cancer | up |
| hsa-mir-199a | hepatocellular carcinoma | down |
| hsa-mir-199a | kidney cancer | down |
| hsa-mir-199a | non-small cell lung cancer | down |
| hsa-mir-199a | ovarian cancer | down |
| hsa-mir-199a | primary cns lymphomas | down |
| hsa-mir-199a-3p | gastric cancer | down |
| hsa-mir-199a-3p | osteosarcoma | down |
| hsa-mir-199a-3p | esophageal adenocarcinoma | up |
| hsa-mir-199a-5p | esophageal adenocarcinoma | up |
| hsa-mir-199a-5p | hepatocellular carcinoma | down |
| hsa-mir-199a-5p | colorectal cancer | down |
| hsa-mir-199b | choriocarcinoma | down |
| hsa-mir-199b | hepatocellular carcinoma | down |
| hsa-mir-199b | prostate cancer | down |
| hsa-mir-199b-3p | esophageal adenocarcinoma | up |
| hsa-mir-199b-5p | hepatocellular carcinoma | down |
| hsa-mir-199b-5p | medulloblastoma | down |
| hsa-mir-199b-5p | mesenchymal cancer | down |
| hsa-mir-199b-5p | breast cancer | down |
| hsa-mir-19a | b-cell lymphoma | up |
| hsa-mir-19a | breast carcinoma | up |
| hsa-mir-19a | cervical cancer | up |

TABLE 1-continued miRNA biomarkers of human cancers

| miRNA | cancer | profile |
|---|---|---|
| hsa-mir-19a | colorectal cancer | up |
| hsa-mir-19a | esophageal squamous cell carcinoma | up |
| hsa-mir-19a | gastric cancer | up |
| hsa-mir-19a | glioma | up |
| hsa-mir-19a | lung cancer | up |
| hsa-mir-19a | mantle cell lymphoma | up |
| hsa-mir-19a | medulloblastoma | up |
| hsa-mir-19a | non-small cell lung cancer | up |
| hsa-mir-19a-3p | breast cancer | down |
| hsa-mir-19b | b-cell lymphoma | up |
| hsa-mir-19b | breast carcinoma | up |
| hsa-mir-19b | cervical cancer | up |
| hsa-mir-19b | colorectal cancer | up |
| hsa-mir-19b | esophageal squamous cell carcinoma | up |
| hsa-mir-19b | gastric cancer | up |
| hsa-mir-19b | glioma | up |
| hsa-mir-19b | lung cancer | up |
| hsa-mir-19b | mantle cell lymphoma | up |
| hsa-mir-19b | medulloblastoma | up |
| hsa-mir-200a | bladder cancer | down |
| hsa-mir-200a | breast cancer | up |
| hsa-mir-200a | esophageal adenocarcinoma | up |
| hsa-mir-200a | gastric adenocarcinoma | down |
| hsa-mir-200a | glioma | down |
| hsa-mir-200a | hepatocellular carcinoma | down |
| hsa-mir-200a | lung adenocarcinoma | down |
| hsa-mir-200a | malignant melanoma | up |
| hsa-mir-200a | meningioma | down |
| hsa-mir-200a | mesenchymal cancer | down |
| hsa-mir-200a | non-small cell lung cancer | up |
| hsa-mir-200a | ovarian cancer | down |
| hsa-mir-200b | bladder cancer | down |
| hsa-mir-200b | breast cancer | down |
| hsa-mir-200b | breast cancer | up |
| hsa-mir-200b | cholangiocarcinoma | down |
| hsa-mir-200b | esophageal squamous cell carcinoma | down |
| hsa-mir-200b | gastric cancer | up |
| hsa-mir-200b | gastric cancer | down |
| hsa-mir-200b | glioma | down |
| hsa-mir-200b | lung adenocarcinoma | down |
| hsa-mir-200b | malignant melanoma | up |
| hsa-mir-200b | mesenchymal cancer | down |
| hsa-mir-200b | nasopharyngeal carcinoma | down |
| hsa-mir-200b | ovarian cancer | down |
| hsa-mir-200b | prostate cancer | down |
| hsa-mir-200b | tongue cancer | down |
| hsa-mir-200c | bladder cancer | down |
| hsa-mir-200c | breast cancer | up |
| hsa-mir-200c | cholangiocarcinoma | down |
| hsa-mir-200c | colon cancer | down |
| hsa-mir-200c | colorectal cancer | down |
| hsa-mir-200c | colorectal cancer | up |
| hsa-mir-200c | endometrial cancer | up |
| hsa-mir-200c | gastric cancer | down |
| hsa-mir-200c | head and neck squamous cell carcinoma | down |
| hsa-mir-200c | hepatocellular carcinoma | down |
| hsa-mir-200c | lung adenocarcinoma | down |
| hsa-mir-200c | malignant melanoma | up |
| hsa-mir-200c | malignant melanoma | down |
| hsa-mir-200c | mesenchymal cancer | down |
| hsa-mir-200c | non-small cell lung cancer | up |
| hsa-mir-200c | ovarian cancer | down |
| hsa-mir-200c | ovarian cancer | up |
| hsa-mir-200c | rectal cancer | up |
| hsa-mir-200c | renal clear cell carcinoma | down |
| hsa-mir-202-3p | gastric cancer | down |
| hsa-mir-202-3p | colorectal carcinoma | down |
| hsa-mir-203 | basal cell carcinoma | down |
| hsa-mir-203 | bladder cancer | down |
| hsa-mir-203 | bladder cancer | up |
| hsa-mir-203 | breast cancer | up |
| hsa-mir-203 | cervical cancer | down |
| hsa-mir-203 | colorectal cancer | up |
| hsa-mir-203 | esophageal adenocarcinoma | down |
| hsa-mir-203 | esophageal cancer | down |
| hsa-mir-203 | esophageal squamous cell carcinoma | down |
| hsa-mir-203 | glioma | down |
| hsa-mir-203 | hepatocellular carcinoma | down |
| hsa-mir-203 | lung cancer | down |
| hsa-mir-203 | malignant melanoma | down |
| hsa-mir-203 | pancreatic adenocarcinoma | up |
| hsa-mir-203 | pancreatic cancer | down |
| hsa-mir-203 | pancreatic ductal adenocarcinoma | up |
| hsa-mir-203 | rhabdomyosarcoma | down |
| hsa-mir-203 | squamous carcinoma | down |
| hsa-mir-203 | squamous carcinoma | up |
| hsa-mir-204 | glioma | down |
| hsa-mir-204 | malignant melanoma | down |
| hsa-mir-204 | prostate cancer | up |
| hsa-mir-204 | renal clear cell carcinoma | down |
| hsa-mir-204 | gastric cancer | down |
| hsa-mir-205 | bladder cancer | up |
| hsa-mir-205 | bladder cancer | down |
| hsa-mir-205 | breast cancer | down |
| hsa-mir-205 | cervical cancer | up |
| hsa-mir-205 | cervical squamous cell carcinoma | up |
| hsa-mir-205 | endometrial cancer | up |
| hsa-mir-205 | glioma | down |
| hsa-mir-205 | head and neck squamous cell carcinoma | down |
| hsa-mir-205 | hepatocellular carcinoma | down |
| hsa-mir-205 | kidney cancer | down |
| hsa-mir-205 | laryngeal squamous cell carcinoma | down |
| hsa-mir-205 | lung cancer | up |
| hsa-mir-205 | malignant melanoma | down |
| hsa-mir-205 | non-small cell lung cancer | up |
| hsa-mir-205 | prostate cancer | down |
| hsa-mir-205 | squamous carcinoma | down |
| hsa-mir-205-3p | non-small cell lung cancer | up |
| hsa-mir-205-5p | non-small cell lung cancer | up |
| hsa-mir-206 | gastric cancer | down |
| hsa-mir-206 | laryngeal squamous cell carcinoma | down |
| hsa-mir-206 | malignant melanoma | down |
| hsa-mir-206 | breast cancer | down |
| hsa-mir-20a | acute myeloid leukemia | down |
| hsa-mir-20a | b-cell lymphoma | up |
| hsa-mir-20a | breast cancer | up |
| hsa-mir-20a | breast carcinoma | up |
| hsa-mir-20a | cervical cancer | up |
| hsa-mir-20a | colorectal cancer | up |
| hsa-mir-20a | esophageal squamous cell carcinoma | up |
| hsa-mir-20a | gastric cancer | up |
| hsa-mir-20a | glioma | up |
| hsa-mir-20a | hepatocellular carcinoma | down |
| hsa-mir-20a | lung cancer | up |
| hsa-mir-20a | malignant melanoma | up |
| hsa-mir-20a | mantle cell lymphoma | up |
| hsa-mir-20a | medulloblastoma | up |
| hsa-mir-20a | nasopharyngeal cancer | up |
| hsa-mir-20a | ovarian cancer | up |
| hsa-mir-20a | prostate cancer | up |
| hsa-mir-20a-5p | colorectal cancer | up |
| hsa-mir-20b | hepatocellular carcinoma | up |
| hsa-mir-21 | adrenal cortical carcinoma | up |
| hsa-mir-21 | breast cancer | up |
| hsa-mir-21 | cervical carcinoma | up |
| hsa-mir-21 | cholangiocarcinoma | up |
| hsa-mir-21 | colorectal cancer | up |
| hsa-mir-21 | colorectal carcinoma | up |
| hsa-mir-21 | diffuse large B-cell lymphoma | up |
| hsa-mir-21 | endometrial cancer | up |
| hsa-mir-21 | esophageal squamous cell carcinoma | up |
| hsa-mir-21 | esophageal squamous cell carcinoma | down |
| hsa-mir-21 | gastric cancer | up |
| hsa-mir-21 | glioblastoma | up |
| hsa-mir-21 | glioblastoma | down |
| hsa-mir-21 | head and neck cancer | up |
| hsa-mir-21 | head and neck squamous cell carcinoma | up |
| hsa-mir-21 | hepatocellular carcinoma | up |
| hsa-mir-21 | hypopharyngeal squamous cell carcinoma | up |
| hsa-mir-21 | kidney cancer | up |
| hsa-mir-21 | laryngeal carcinoma | up |
| hsa-mir-21 | laryngeal squamous cell carcinoma | up |

TABLE 1-continued miRNA biomarkers of human cancers

| miRNA | cancer | profile |
|---|---|---|
| hsa-mir-21 | liver cancer | up |
| hsa-mir-21 | lung cancer | up |
| hsa-mir-21 | malignant melanoma | up |
| hsa-mir-21 | non-small cell lung cancer | up |
| hsa-mir-21 | oral cancer | up |
| hsa-mir-21 | osteosarcoma | up |
| hsa-mir-21 | ovarian cancer | up |
| hsa-mir-21 | pancreatic cancer | up |
| hsa-mir-21 | pancreatic ductal adenocarcinoma | up |
| hsa-mir-21 | papillary thyroid carcinoma | up |
| hsa-mir-21 | renal cell carcinoma | up |
| hsa-mir-21 | squamous carcinoma | up |
| hsa-mir-21-3p | hepatocellular carcinoma | down |
| hsa-mir-210 | adrenal cortical carcinoma | up |
| hsa-mir-210 | bladder cancer | up |
| hsa-mir-210 | esophageal squamous cell carcinoma | down |
| hsa-mir-210 | gastric cancer | down |
| hsa-mir-210 | glioma | up |
| hsa-mir-210 | hepatocellular carcinoma | up |
| hsa-mir-210 | kidney cancer | up |
| hsa-mir-210 | lung cancer | up |
| hsa-mir-210 | malignant melanoma | up |
| hsa-mir-210 | osteosarcoma | up |
| hsa-mir-210 | renal cell carcinoma | up |
| hsa-mir-210 | renal clear cell carcinoma | up |
| hsa-mir-211 | malignant melanoma | down |
| hsa-mir-211 | colorectal cancer | up |
| hsa-mir-212 | colorectal cancer | down |
| hsa-mir-212 | gastric cancer | down |
| hsa-mir-212 | hepatocellular carcinoma | down |
| hsa-mir-212 | non-small cell lung cancer | up |
| hsa-mir-212 | non-small cell lung cancer | down |
| hsa-mir-212 | pancreatic cancer | up |
| hsa-mir-214 | cervical cancer | down |
| hsa-mir-214 | cervical squamous cell carcinoma | down |
| hsa-mir-214 | esophageal squamous cell carcinoma | down |
| hsa-mir-214 | gastric cancer | up |
| hsa-mir-214 | hepatocellular carcinoma | down |
| hsa-mir-214 | hepatocellular carcinoma | up |
| hsa-mir-214 | malignant melanoma | up |
| hsa-mir-214 | multiple myeloma | down |
| hsa-mir-214 | nasopharyngeal carcinoma | up |
| hsa-mir-214 | osteosarcoma | up |
| hsa-mir-214 | ovarian cancer | up |
| hsa-mir-214 | pancreatic cancer | down |
| hsa-mir-214 | pancreatic cancer | up |
| hsa-mir-214 | primary cns lymphomas | down |
| hsa-mir-215 | colon cancer | down |
| hsa-mir-215 | colorectal cancer | down |
| hsa-mir-215 | gastric cancer | up |
| hsa-mir-215 | hepatocellular carcinoma | up |
| hsa-mir-216a | hepatocellular carcinoma | up |
| hsa-mir-216a | pancreatic cancer | down |
| hsa-mir-216b | nasopharyngeal carcinoma | down |
| hsa-mir-217 | pancreatic ductal adenocarcinoma | down |
| hsa-mir-217 | hepatocellular carcinoma | up |
| hsa-mir-218 | breast cancer | down |
| hsa-mir-218 | cervical cancer | down |
| hsa-mir-218 | cervical squamous cell carcinoma | down |
| hsa-mir-218 | colorectal cancer | down |
| hsa-mir-218 | gastric cancer | down |
| hsa-mir-218 | gastrointestinal stromal tumor | down |
| hsa-mir-218 | glioma | down |
| hsa-mir-218 | head and neck squamous cell carcinoma | down |
| hsa-mir-218 | lung cancer | down |
| hsa-mir-218 | lung squamous cell carcinoma | down |
| hsa-mir-218 | nasopharyngeal cancer | down |
| hsa-mir-218 | oral cancer | down |
| hsa-mir-218 | osteosarcoma | down |
| hsa-mir-218 | pancreatic ductal adenocarcinoma | down |
| hsa-mir-218 | renal cell carcinoma | down |
| hsa-mir-218 | renal clear cell carcinoma | down |
| hsa-mir-219-5p | glioma | down |
| hsa-mir-219-5p | hepatocellular carcinoma | down |
| hsa-mir-219-5p | glioblastoma | down |
| hsa-mir-22 | colon cancer | down |
| hsa-mir-22 | colorectal cancer | down |
| hsa-mir-22 | esophageal squamous cell carcinoma | down |
| hsa-mir-22 | gastric cancer | down |
| hsa-mir-22 | hepatocellular carcinoma | down |
| hsa-mir-22 | lung cancer | down |
| hsa-mir-22 | medulloblastoma | down |
| hsa-mir-22 | non-small cell lung cancer | up |
| hsa-mir-22 | t-cell lymphoma | down |
| hsa-mir-221 | anaplastic thyroid carcinoma | up |
| hsa-mir-221 | bladder cancer | up |
| hsa-mir-221 | breast cancer | up |
| hsa-mir-221 | colon carcinoma | up |
| hsa-mir-221 | colorectal cancer | up |
| hsa-mir-221 | gastric cancer | up |
| hsa-mir-221 | gastrointestinal stromal tumor | down |
| hsa-mir-221 | glioma | up |
| hsa-mir-221 | hepatocellular carcinoma | up |
| hsa-mir-221 | malignant melanoma | up |
| hsa-mir-221 | non-small cell lung cancer | down |
| hsa-mir-221 | non-small cell lung cancer | up |
| hsa-mir-221 | oral squamous cell carcinoma | up |
| hsa-mir-221 | osteosarcoma | up |
| hsa-mir-221 | ovarian cancer | up |
| hsa-mir-221 | pancreatic cancer | up |
| hsa-mir-221 | papillary thyroid carcinoma | up |
| hsa-mir-221 | prostate cancer | up |
| hsa-mir-221 | squamous carcinoma | up |
| hsa-mir-221 | thyroid carcinoma | up |
| hsa-mir-221* | gastric cancer | up |
| hsa-mir-222 | anaplastic thyroid carcinoma | up |
| hsa-mir-222 | breast cancer | up |
| hsa-mir-222 | gastric cancer | up |
| hsa-mir-222 | gastrointestinal stromal tumor | down |
| hsa-mir-222 | glioblastoma | down |
| hsa-mir-222 | glioma | up |
| hsa-mir-222 | hepatocellular carcinoma | up |
| hsa-mir-222 | malignant melanoma | up |
| hsa-mir-222 | non-small cell lung cancer | up |
| hsa-mir-222 | oral squamous cell carcinoma | up |
| hsa-mir-222 | papillary thyroid carcinoma | up |
| hsa-mir-222 | thyroid carcinoma | up |
| hsa-mir-223 | acute myeloid leukemia | down |
| hsa-mir-223 | bladder cancer | up |
| hsa-mir-223 | chronic lymphocytic leukemia | down |
| hsa-mir-223 | colorectal cancer | up |
| hsa-mir-223 | esophageal adenocarcinoma | up |
| hsa-mir-223 | esophageal squamous cell carcinoma | up |
| hsa-mir-223 | gastric cancer | up |
| hsa-mir-223 | glioblastoma | up |
| hsa-mir-223 | hepatocellular carcinoma | up |
| hsa-mir-223 | hepatocellular carcinoma | down |
| hsa-mir-223 | lung cancer | down |
| hsa-mir-223 | mantle cell lymphoma | down |
| hsa-mir-223 | nasopharyngeal cancer | down |
| hsa-mir-223 | splenic marginal zone lymphoma | down |
| hsa-mir-224 | breast cancer | up |
| hsa-mir-224 | cervical cancer | up |
| hsa-mir-224 | colorectal cancer | up |
| hsa-mir-224 | glioma | up |
| hsa-mir-224 | hepatocellular carcinoma | up |
| hsa-mir-224 | prostate cancer | down |
| hsa-mir-23a | bladder cancer | up |
| hsa-mir-23a | breast cancer | up |
| hsa-mir-23a | colon carcinoma | up |
| hsa-mir-23a | gastric adenocarcinoma | up |
| hsa-mir-23a | gastric cancer | up |
| hsa-mir-23a | glioma | up |
| hsa-mir-23a | hepatocellular carcinoma | up |
| hsa-mir-23a | neuroblastoma | up |
| hsa-mir-23b | bladder cancer | down |
| hsa-mir-23b | bladder cancer | up |
| hsa-mir-23b | gastric cancer | up |
| hsa-mir-23b | glioma | down |
| hsa-mir-23b | ovarian cancer | up |
| hsa-mir-23b | prostate cancer | down |
| hsa-mir-24 | breast carcinoma | up |

TABLE 1-continued miRNA biomarkers of human cancers

| miRNA | cancer | profile |
|---|---|---|
| hsa-mir-24 | glioma | up |
| hsa-mir-24 | laryngeal squamous cell carcinoma | down |
| hsa-mir-24 | lung cancer | up |
| hsa-mir-24 | non-small cell lung cancer | up |
| hsa-mir-24 | oral squamous cell carcinoma | up |
| hsa-mir-24 | osteosarcoma | down |
| hsa-mir-24-2-5p | breast cancer | up |
| hsa-mir-24-3p | glioma | up |
| hsa-mir-25 | colon cancer | down |
| hsa-mir-25 | colorectal cancer | up |
| hsa-mir-25 | endometrial cancer | up |
| hsa-mir-25 | esophageal squamous cell carcinoma | up |
| hsa-mir-25 | gastric cancer | up |
| hsa-mir-25 | head and neck squamous cell carcinoma | up |
| hsa-mir-25 | hepatocellular carcinoma | up |
| hsa-mir-25 | ovarian cancer | up |
| hsa-mir-26a | acute myeloid leukemia | down |
| hsa-mir-26a | bladder cancer | down |
| hsa-mir-26a | breast cancer | down |
| hsa-mir-26a | cholangiocarcinoma | up |
| hsa-mir-26a | gastric cancer | down |
| hsa-mir-26a | glioma | up |
| hsa-mir-26a | hepatocellular carcinoma | down |
| hsa-mir-26a | malignant melanoma | down |
| hsa-mir-26a | osteosarcoma | down |
| hsa-mir-26a | ovarian cancer | up |
| hsa-mir-26a | papillary thyroid carcinoma | down |
| hsa-mir-26a | primary thyroid lymphoma | down |
| hsa-mir-26a | prostate cancer | down |
| hsa-mir-26b | breast cancer | down |
| hsa-mir-26b | colorectal cancer | down |
| hsa-mir-26b | glioma | down |
| hsa-mir-26b | prostate cancer | down |
| hsa-mir-26b | bladder cancer | up |
| hsa-mir-27a | acute leukemia | down |
| hsa-mir-27a | breast cancer | up |
| hsa-mir-27a | esophageal squamous cell carcinoma | down |
| hsa-mir-27a | gastric adenocarcinoma | up |
| hsa-mir-27a | gastric cancer | up |
| hsa-mir-27a | non-small cell lung cancer | down |
| hsa-mir-27a | osteosarcoma | up |
| hsa-mir-27a | ovarian cancer | up |
| hsa-mir-27a | pancreatic cancer | up |
| hsa-mir-27a | small cell lung cancer | down |
| hsa-mir-27a | squamous carcinoma | up |
| hsa-mir-27a* | head and neck squamous cell carcinoma | down |
| hsa-mir-27a-3p | glioma | up |
| hsa-mir-27b | glioma | up |
| hsa-mir-27b | ovarian cancer | up |
| hsa-mir-27b | gastric cancer | up |
| hsa-mir-28-3p | colorectal cancer | down |
| hsa-mir-28-5p | colorectal cancer | down |
| hsa-mir-296-5p | gastric cancer | up |
| hsa-mir-29a | acute myeloid leukemia | up |
| hsa-mir-29a | acute myeloid leukemia | down |
| hsa-mir-29a | breast cancer | up |
| hsa-mir-29a | cervical squamous cell carcinoma | down |
| hsa-mir-29a | colorectal cancer | up |
| hsa-mir-29a | gastric cancer | down |
| hsa-mir-29a | head and neck squamous cell carcinoma | down |
| hsa-mir-29a | hepatocellular carcinoma | down |
| hsa-mir-29a | mantle cell lymphoma | down |
| hsa-mir-29a | mesenchymal cancer | down |
| hsa-mir-29a | non-small cell lung cancer | down |
| hsa-mir-29a | oral squamous cell carcinoma | down |
| hsa-mir-29b | glioblastoma | down |
| hsa-mir-29b | lung adenocarcinoma | down |
| hsa-mir-29b | mantle cell lymphoma | down |
| hsa-mir-29b | non-small cell lung cancer | down |
| hsa-mir-29b | osteosarcoma | down |
| hsa-mir-29b | prostate cancer | down |
| hsa-mir-29b | chronic lymphocytic leukemia | down |
| hsa-mir-29b-1 | gastric cancer | down |
| hsa-mir-29b-1 | head and neck squamous cell carcinoma | down |
| hsa-mir-29b-1 | hepatocellular carcinoma | down |
| hsa-mir-29b-1 | mesenchymal cancer | down |
| hsa-mir-29b-1-5p | mesenchymal cancer | down |
| hsa-mir-29b-2 | head and neck squamous cell carcinoma | down |
| hsa-mir-29b-2 | hepatocellular carcinoma | down |
| hsa-mir-29b-2 | mesenchymal cancer | down |
| hsa-mir-29b-2 | gastric cancer | down |
| hsa-mir-29c | esophageal squamous cell carcinoma | down |
| hsa-mir-29c | gastric cancer | down |
| hsa-mir-29c | glioma | down |
| hsa-mir-29c | head and neck squamous cell carcinoma | down |
| hsa-mir-29c | hepatocellular carcinoma | down |
| hsa-mir-29c | lung cancer | down |
| hsa-mir-29c | mantle cell lymphoma | down |
| hsa-mir-29c | mesenchymal cancer | down |
| hsa-mir-29c | nasopharyngeal cancer | down |
| hsa-mir-29c | nasopharyngeal carcinoma | down |
| hsa-mir-29c | non-small cell lung cancer | up |
| hsa-mir-29c | non-small cell lung cancer | down |
| hsa-mir-301a | gastric cancer | up |
| hsa-mir-301a | hepatocellular carcinoma | up |
| hsa-mir-301a | pancreatic adenocarcinoma | up |
| hsa-mir-301a | pancreatic cancer | up |
| hsa-mir-301b | pancreatic carcinoma | up |
| hsa-mir-302b | gastric adenocarcinoma | down |
| hsa-mir-302b | hepatocellular carcinoma | down |
| hsa-mir-302b | esophageal squamous cell carcinoma | down |
| hsa-mir-302f | gastric cancer | up |
| hsa-mir-30a | breast cancer | down |
| hsa-mir-30a | colorectal carcinoma | down |
| hsa-mir-30a | non-small cell lung cancer | down |
| hsa-mir-30a | prostate cancer | down |
| hsa-mir-30a-3p | hepatocellular carcinoma | down |
| hsa-mir-30a-3p | colorectal cancer | down |
| hsa-mir-30a-5p | colon carcinoma | down |
| hsa-mir-30a-5p | esophageal squamous cell carcinoma | up |
| hsa-mir-30a-5p | gastric cancer | down |
| hsa-mir-30a-5p | glioma | up |
| hsa-mir-30a-5p | head and neck squamous cell carcinoma | up |
| hsa-mir-30b | medulloblastoma | up |
| hsa-mir-30b | prostate cancer | down |
| hsa-mir-30b | colorectal cancer | down |
| hsa-mir-30b-5p | pancreatic ductal adenocarcinoma | up |
| hsa-mir-30c | acute myeloid leukemia | down |
| hsa-mir-30c | endometrial cancer | down |
| hsa-mir-30c | renal cell carcinoma | down |
| hsa-mir-30c-1 | prostate cancer | down |
| hsa-mir-30c-2 | prostate cancer | down |
| hsa-mir-30d | hepatocellular carcinoma | up |
| hsa-mir-30d | lung cancer | up |
| hsa-mir-30d | medulloblastoma | up |
| hsa-mir-30d | non-small cell lung cancer | down |
| hsa-mir-30d | prostate cancer | down |
| hsa-mir-30d | renal cell carcinoma | down |
| hsa-mir-30e* | prostate cancer | down |
| hsa-mir-30e* | glioma | up |
| hsa-mir-30e-5p | non-small cell lung cancer | down |
| hsa-mir-31 | breast cancer | down |
| hsa-mir-31 | chronic myelogenous leukemia | down |
| hsa-mir-31 | colon cancer | up |
| hsa-mir-31 | colorectal cancer | up |
| hsa-mir-31 | esophageal squamous cell carcinoma | up |
| hsa-mir-31 | gastric cancer | down |
| hsa-mir-31 | glioblastoma | down |
| hsa-mir-31 | hepatocellular carcinoma | up |
| hsa-mir-31 | lung adenocarcinoma | up |
| hsa-mir-31 | malignant melanoma | down |
| hsa-mir-31 | non-small cell lung cancer | up |
| hsa-mir-31 | oral carcinoma | up |
| hsa-mir-31 | oral squamous cell carcinoma | up |
| hsa-mir-31 | pancreatic ductal adenocarcinoma | up |
| hsa-mir-31 | prostate cancer | up |
| hsa-mir-31 | prostate cancer | down |
| hsa-mir-32 | colorectal cancer | up |
| hsa-mir-32 | acute myeloid leukemia | up |
| hsa-mir-320 | osteosarcoma | down |
| hsa-mir-320a | colon cancer | down |
| hsa-mir-320a | colorectal cancer | down |

TABLE 1-continued miRNA biomarkers of human cancers

| miRNA | cancer | profile |
|---|---|---|
| hsa-mir-324-3p | nasopharyngeal carcinoma | down |
| hsa-mir-326 | glioblastoma | down |
| hsa-mir-326 | glioma | down |
| hsa-mir-326 | chronic myelogenous leukemia | down |
| hsa-mir-328 | colorectal cancer | down |
| hsa-mir-328 | gastric cancer | down |
| hsa-mir-328 | glioma | up |
| hsa-mir-328 | non-small cell lung cancer | up |
| hsa-mir-330 | prostate cancer | down |
| hsa-mir-330 | glioblastoma | down |
| hsa-mir-331-3p | glioblastoma | down |
| hsa-mir-331-3p | prostate cancer | down |
| hsa-mir-331-3p | gastric cancer | down |
| hsa-mir-335 | adrenal cortical carcinoma | down |
| hsa-mir-335 | astrocytoma | up |
| hsa-mir-335 | breast cancer | down |
| hsa-mir-335 | glioma | up |
| hsa-mir-335 | hepatocellular carcinoma | down |
| hsa-mir-335 | meningioma | up |
| hsa-mir-335 | mesenchymal cancer | down |
| hsa-mir-335 | neuroblastoma | down |
| hsa-mir-335 | non-small cell lung cancer | down |
| hsa-mir-335 | osteosarcoma | down |
| hsa-mir-335 | ovarian cancer | down |
| hsa-mir-335 | primary gallbladder carcinoma | down |
| hsa-mir-335 | renal clear cell carcinoma | down |
| hsa-mir-337-3p | gastric cancer | up |
| hsa-mir-338-3p | colorectal carcinoma | down |
| hsa-mir-338-3p | gastric cancer | down |
| hsa-mir-338-3p | hepatocellular carcinoma | down |
| hsa-mir-338-3p | liver cancer | down |
| hsa-mir-338-3p | neuroblastoma | down |
| hsa-mir-339 | non-small cell lung cancer | up |
| hsa-mir-339-5p | breast cancer | down |
| hsa-mir-33a | hepatocellular carcinoma | down |
| hsa-mir-340 | osteosarcoma | down |
| hsa-mir-340* | gastric cancer | up |
| hsa-mir-342 | colorectal cancer | down |
| hsa-mir-342 | glioblastoma | down |
| hsa-mir-342 | acute promyelocytic leukemia | down |
| hsa-mir-345 | colorectal cancer | down |
| hsa-mir-346 | ovarian cancer | up |
| hsa-mir-346 | follicular thyroid carcinoma | up |
| hsa-mir-34a | b-cell lymphoma | down |
| hsa-mir-34a | breast cancer | down |
| hsa-mir-34a | cervical carcinoma | down |
| hsa-mir-34a | choriocarcinoma | down |
| hsa-mir-34a | colon cancer | down |
| hsa-mir-34a | colorectal cancer | down |
| hsa-mir-34a | endometrial cancer | down |
| hsa-mir-34a | gastric cancer | up |
| hsa-mir-34a | gastric cancer | down |
| hsa-mir-34a | glioblastoma | down |
| hsa-mir-34a | glioma | down |
| hsa-mir-34a | head and neck squamous cell carcinoma | down |
| hsa-mir-34a | hepatocellular carcinoma | down |
| hsa-mir-34a | lung cancer | down |
| hsa-mir-34a | malignant melanoma | down |
| hsa-mir-34a | neuroblastoma | down |
| hsa-mir-34a | non-small cell lung cancer | down |
| hsa-mir-34a | non-small cell lung cancer | up |
| hsa-mir-34a | osteosarcoma | down |
| hsa-mir-34a | ovarian cancer | down |
| hsa-mir-34a | pancreatic cancer | down |
| hsa-mir-34a | papillary thyroid carcinoma | up |
| hsa-mir-34a | prostate cancer | down |
| hsa-mir-34a | rectal cancer | up |
| hsa-mir-34a | renal cell carcinoma | down |
| hsa-mir-34a | retinoblastoma | down |
| hsa-mir-34a | squamous carcinoma | up |
| hsa-mir-34a | uveal melanoma | down |
| hsa-mir-34b | breast cancer | down |
| hsa-mir-34b | chronic lymphocytic leukemia | down |
| hsa-mir-34b | endometrial serous adenocarcinoma | down |
| hsa-mir-34b | gastric cancer | down |
| hsa-mir-34b | lung cancer | down |
| hsa-mir-34b | non-small cell lung cancer | down |
| hsa-mir-34b | ovarian cancer | down |
| hsa-mir-34b | ovarian carcinoma | down |
| hsa-mir-34b | pancreatic cancer | down |
| hsa-mir-34b | papillary thyroid carcinoma | down |
| hsa-mir-34b | prostate cancer | down |
| hsa-mir-34b | uveal melanoma | down |
| hsa-mir-34c | breast cancer | down |
| hsa-mir-34c | chronic lymphocytic leukemia | down |
| hsa-mir-34c | colon cancer | down |
| hsa-mir-34c | endometrial cancer | down |
| hsa-mir-34c | gastric cancer | down |
| hsa-mir-34c | lung cancer | down |
| hsa-mir-34c | malignant melanoma | down |
| hsa-mir-34c | ovarian cancer | down |
| hsa-mir-34c | ovarian carcinoma | down |
| hsa-mir-34c | pancreatic cancer | down |
| hsa-mir-34c | prostate cancer | down |
| hsa-mir-34c | uveal melanoma | down |
| hsa-mir-34c-3p | glioma | down |
| hsa-mir-34c-5p | glioma | down |
| hsa-mir-361-3p | non-small cell lung cancer | down |
| hsa-mir-363 | head and neck squamous cell carcinoma | down |
| hsa-mir-365 | lung cancer | down |
| hsa-mir-365 | colon cancer | down |
| hsa-mir-365b-3p | retinoblastoma | down |
| hsa-mir-369-5p | pancreatic ductal adenocarcinoma | up |
| hsa-mir-370 | gastric cancer | up |
| hsa-mir-370 | hepatocellular carcinoma | down |
| hsa-mir-370 | laryngeal squamous cell carcinoma | down |
| hsa-mir-370 | oral squamous cell carcinoma | down |
| hsa-mir-370 | acute myeloid leukemia | up |
| hsa-mir-371-5p | hepatocellular carcinoma | up |
| hsa-mir-372 | cervical cancer | down |
| hsa-mir-372 | glioma | up |
| hsa-mir-372 | hepatocellular carcinoma | down |
| hsa-mir-372 | hepatocellular carcinoma | up |
| hsa-mir-373 | colon cancer | down |
| hsa-mir-373 | esophageal squamous cell carcinoma | up |
| hsa-mir-373 | gastric adenocarcinoma | up |
| hsa-mir-373 | hepatocellular carcinoma | up |
| hsa-mir-373 | breast cancer | up |
| hsa-mir-374a | breast cancer | down |
| hsa-mir-374b | prostate cancer | down |
| hsa-mir-375 | cervical squamous cell carcinoma | down |
| hsa-mir-375 | colorectal cancer | down |
| hsa-mir-375 | esophageal cancer | down |
| hsa-mir-375 | esophageal squamous cell carcinoma | down |
| hsa-mir-375 | gastric cancer | down |
| hsa-mir-375 | glioma | down |
| hsa-mir-375 | head and neck squamous cell carcinoma | down |
| hsa-mir-375 | hepatocellular carcinoma | down |
| hsa-mir-375 | nasopharyngeal carcinoma | down |
| hsa-mir-375 | non-small cell lung cancer | down |
| hsa-mir-375 | oral cancer | down |
| hsa-mir-375 | oral carcinoma | down |
| hsa-mir-375 | pancreatic cancer | down |
| hsa-mir-375 | pancreatic carcinoma | down |
| hsa-mir-375 | pancreatic ductal adenocarcinoma | down |
| hsa-mir-375 | squamous carcinoma | down |
| hsa-mir-376a | hepatocellular carcinoma | down |
| hsa-mir-376a | malignant melanoma | down |
| hsa-mir-376a | pancreatic ductal adenocarcinoma | up |
| hsa-mir-376a | glioblastoma | down |
| hsa-mir-376c | osteosarcoma | down |
| hsa-mir-376c | malignant melanoma | down |
| hsa-mir-378 | acute myeloid leukemia | up |
| hsa-mir-378 | colorectal cancer | down |
| hsa-mir-378 | gastric cancer | down |
| hsa-mir-378 | nasopharyngeal carcinoma | down |
| hsa-mir-378 | ovarian cancer | up |
| hsa-mir-378a-3p | colorectal cancer | down |
| hsa-mir-378a-5p | colorectal cancer | down |
| hsa-mir-379 | breast cancer | down |
| hsa-mir-381 | lung adenocarcinoma | down |
| hsa-mir-381 | breast cancer | down |

TABLE 1-continued miRNA biomarkers of human cancers

| miRNA | cancer | profile |
|---|---|---|
| hsa-mir-383 | medulloblastoma | down |
| hsa-mir-383 | glioma | down |
| hsa-mir-409-3p | bladder cancer | down |
| hsa-mir-409-3p | gastric cancer | down |
| hsa-mir-409-3p | ovarian cancer | down |
| hsa-mir-411 | ovarian cancer | down |
| hsa-mir-421 | gastric cancer | up |
| hsa-mir-421 | nasopharyngeal carcinoma | up |
| hsa-mir-422a | colorectal cancer | down |
| hsa-mir-423 | hepatocellular carcinoma | up |
| hsa-mir-424 | cervical cancer | down |
| hsa-mir-424 | colon cancer | down |
| hsa-mir-424 | colorectal cancer | up |
| hsa-mir-424 | osteosarcoma | down |
| hsa-mir-424 | ovarian cancer | up |
| hsa-mir-424-5p | pancreatic cancer | up |
| hsa-mir-425 | gastric cancer | up |
| hsa-mir-425 | breast cancer | down |
| hsa-mir-429 | bladder cancer | down |
| hsa-mir-429 | breast cancer | up |
| hsa-mir-429 | colorectal cancer | up |
| hsa-mir-429 | colorectal carcinoma | down |
| hsa-mir-429 | gastric cancer | down |
| hsa-mir-429 | hepatocellular carcinoma | up |
| hsa-mir-429 | lung adenocarcinoma | down |
| hsa-mir-429 | malignant melanoma | up |
| hsa-mir-429 | mesenchymal cancer | down |
| hsa-mir-429 | non-small cell lung cancer | down |
| hsa-mir-429 | ovarian cancer | down |
| hsa-mir-432 | ovarian cancer | down |
| hsa-mir-433 | gastric cancer | down |
| hsa-mir-433 | liver cancer | down |
| hsa-mir-4423 | lung cancer | up |
| hsa-mir-449 | gastric cancer | down |
| hsa-mir-449a | gastric adenocarcinoma | down |
| hsa-mir-449a | gastric cancer | down |
| hsa-mir-449a | lung cancer | down |
| hsa-mir-449a | non-small cell lung cancer | down |
| hsa-mir-449a | prostate cancer | down |
| hsa-mir-449b | lung cancer | down |
| hsa-mir-450a | hepatocellular carcinoma | down |
| hsa-mir-451 | colorectal carcinoma | down |
| hsa-mir-451 | esophageal carcinoma | down |
| hsa-mir-451 | glioma | down |
| hsa-mir-451 | hepatocellular carcinoma | down |
| hsa-mir-451 | nasopharyngeal carcinoma | down |
| hsa-mir-451 | non-small cell lung cancer | down |
| hsa-mir-451 | osteosarcoma | down |
| hsa-mir-452 | hepatocellular carcinoma | up |
| hsa-mir-452 | glioma | down |
| hsa-mir-4723-5p | prostate cancer | down |
| hsa-mir-4782-3p | non-small cell lung cancer | down |
| hsa-mir-483-3p | adrenal cortical carcinoma | up |
| hsa-mir-483-5p | adrenal cortical carcinoma | up |
| hsa-mir-483-5p | glioblastoma | down |
| hsa-mir-483-5p | glioma | down |
| hsa-mir-485-3p | hepatocellular carcinoma | up |
| hsa-mir-486 | glioma | up |
| hsa-mir-486-5p | lung cancer | down |
| hsa-mir-490-3p | hepatocellular carcinoma | up |
| hsa-mir-490-5p | bladder cancer | down |
| hsa-mir-492 | hepatoblastoma | up |
| hsa-mir-493 | pituitary carcinoma | up |
| hsa-mir-493 | bladder cancer | down |
| hsa-mir-494 | hepatocellular carcinoma | up |
| hsa-mir-494 | ovarian cancer | down |
| hsa-mir-494 | glioma | up |
| hsa-mir-495 | breast cancer | up |
| hsa-mir-495 | glioma | down |
| hsa-mir-495 | hepatocellular carcinoma | up |
| hsa-mir-497 | adrenal cortical carcinoma | down |
| hsa-mir-497 | breast cancer | down |
| hsa-mir-497 | cervical cancer | down |
| hsa-mir-497 | colorectal cancer | up |
| hsa-mir-497 | colorectal cancer | down |
| hsa-mir-497 | hepatocellular carcinoma | down |
| hsa-mir-497 | non-small cell lung cancer | down |
| hsa-mir-497 | prostate cancer | down |
| hsa-mir-498 | ovarian cancer | down |
| hsa-mir-499-5p | colorectal cancer | up |
| hsa-mir-500 | hepatocellular carcinoma | up |
| hsa-mir-501 | hepatocellular carcinoma | up |
| hsa-mir-502 | colon cancer | down |
| hsa-mir-503 | colon cancer | down |
| hsa-mir-503 | glioblastoma | down |
| hsa-mir-503 | hepatocellular carcinoma | down |
| hsa-mir-503 | non-small cell lung cancer | down |
| hsa-mir-503 | ovarian cancer | up |
| hsa-mir-508-3p | kidney cancer | down |
| hsa-mir-509-3p | kidney cancer | down |
| hsa-mir-509-5p | renal cell carcinoma | down |
| hsa-mir-510 | breast cancer | up |
| hsa-mir-511 | lung adenocarcinoma | down |
| hsa-mir-517a | breast cancer | down |
| hsa-mir-518b | esophageal squamous cell carcinoma | down |
| hsa-mir-519d | hepatocellular carcinoma | down |
| hsa-mir-519d | hepatocellular carcinoma | up |
| hsa-mir-520c | breast cancer | up |
| hsa-mir-520c-3p | hepatocellular carcinoma | down |
| hsa-mir-520c-3p | gastric cancer | up |
| hsa-mir-525-3p | liver cancer | up |
| hsa-mir-532-5p | ovarian carcinoma | down |
| hsa-mir-532-5p | malignant melanoma | up |
| hsa-mir-541 | pancreatic ductal adenocarcinoma | up |
| hsa-mir-544 | gastric cancer | up |
| hsa-mir-545 | lung cancer | down |
| hsa-mir-564 | chronic myelogenous leukemia | down |
| hsa-mir-573 | malignant melanoma | down |
| hsa-mir-574-3p | hepatocellular carcinoma | up |
| hsa-mir-574-3p | breast cancer | down |
| hsa-mir-575 | gastric cancer | up |
| hsa-mir-590-5p | cervical cancer | up |
| hsa-mir-590-5p | hepatocellular carcinoma | up |
| hsa-mir-590-5p | hepatocellular carcinoma | down |
| hsa-mir-601 | gastric cancer | up |
| hsa-mir-612 | hepatocellular carcinoma | down |
| hsa-mir-613 | papillary thyroid carcinoma | down |
| hsa-mir-616* | gastric cancer | up |
| hsa-mir-622 | gastric cancer | down |
| hsa-mir-625 | gastric cancer | down |
| hsa-mir-625 | colorectal cancer | down |
| hsa-mir-625* | non-small cell lung cancer | down |
| hsa-mir-627 | colonic adenocarcinoma | down |
| hsa-mir-628-5p | prostate cancer | down |
| hsa-mir-630 | pancreatic cancer | down |
| hsa-mir-637 | hepatocellular carcinoma | down |
| hsa-mir-638 | gastric cancer | down |
| hsa-mir-639 | bladder cancer | up |
| hsa-mir-642a-5p | prostate cancer | down |
| hsa-mir-650 | gastric cancer | up |
| hsa-mir-650 | glioma | up |
| hsa-mir-650 | hepatocellular carcinoma | up |
| hsa-mir-655 | ovarian cancer | down |
| hsa-mir-655 | esophageal squamous cell carcinoma | down |
| hsa-mir-656 | glioma | down |
| hsa-mir-657 | hepatocellular carcinoma | up |
| hsa-mir-663 | gastric cancer | down |
| hsa-mir-663 | lung cancer | up |
| hsa-mir-663 | nasopharyngeal carcinoma | up |
| hsa-mir-664 | hepatocellular carcinoma | up |
| hsa-mir-675 | glioma | up |
| hsa-mir-675 | colon cancer | up |
| hsa-mir-7 | breast cancer | down |
| hsa-mir-7 | colorectal cancer | down |
| hsa-mir-7 | gastric cancer | down |
| hsa-mir-7 | glioblastoma | down |
| hsa-mir-7 | glioma | down |
| hsa-mir-7 | hepatocellular carcinoma | down |
| hsa-mir-7 | lung cancer | up |
| hsa-mir-7 | renal cell carcinoma | up |
| hsa-mir-7-5p | malignant melanoma | down |
| hsa-mir-720 | breast cancer | down |

TABLE 1-continued miRNA biomarkers of human cancers

| miRNA | cancer | profile |
|---|---|---|
| hsa-mir-7515 | lung cancer | down |
| hsa-mir-802 | osteosarcoma | up |
| hsa-mir-874 | gastric cancer | down |
| hsa-mir-874 | head and neck squamous cell carcinoma | down |
| hsa-mir-885-5p | neuroblastoma | down |
| hsa-mir-885-5p | hepatocellular carcinoma | up |
| hsa-mir-886-3p | thyroid cancer | down |
| hsa-mir-886-5p | cervical carcinoma | down |
| hsa-mir-9 | gastric adenocarcinoma | down |
| hsa-mir-9 | gastric cancer | down |
| hsa-mir-9 | glioma | up |
| hsa-mir-9 | malignant melanoma | down |
| hsa-mir-9 | nasopharyngeal carcinoma | down |
| hsa-mir-9 | non-small cell lung cancer | up |
| hsa-mir-9 | oral squamous cell carcinoma | down |
| hsa-mir-9 | ovarian cancer | down |
| hsa-mir-9 | uveal melanoma | down |
| hsa-mir-92 | gastric cancer | up |
| hsa-mir-92 | medulloblastoma | up |
| hsa-mir-92 | neuroblastoma | up |
| hsa-mir-92 | pancreatic cancer | up |
| hsa-mir-92 | colorectal cancer | up |
| hsa-mir-92a | acute promyelocytic leukemia | up |
| hsa-mir-92a | b-cell lymphoma | up |
| hsa-mir-92a | breast cancer | down |
| hsa-mir-92a | breast carcinoma | up |
| hsa-mir-92a | colorectal cancer | up |
| hsa-mir-92a | esophageal squamous cell carcinoma | up |
| hsa-mir-92a | hepatocellular carcinoma | up |
| hsa-mir-92a | lung cancer | up |
| hsa-mir-92a | malignant melanoma | up |
| hsa-mir-92a | mantle cell lymphoma | up |
| hsa-mir-92b | glioma | up |
| hsa-mir-92b | non-small cell lung cancer | up |
| hsa-mir-92b | glioblastoma | up |
| hsa-mir-93 | colon cancer | down |
| hsa-mir-93 | colorectal cancer | up |
| hsa-mir-93 | endometrial cancer | up |
| hsa-mir-93 | head and neck squamous cell carcinoma | up |
| hsa-mir-93 | non-small cell lung cancer | up |
| hsa-mir-95 | colorectal carcinoma | up |
| hsa-mir-95 | colorectal cancer | up |
| hsa-mir-96 | bladder cancer | up |
| hsa-mir-96 | breast cancer | up |
| hsa-mir-96 | chronic myelogenous leukemia | up |
| hsa-mir-96 | colorectal cancer | up |
| hsa-mir-96 | glioma | up |
| hsa-mir-96 | hepatocellular carcinoma | up |
| hsa-mir-96 | ovarian cancer | up |
| hsa-mir-96 | pancreatic cancer | down |
| hsa-mir-96 | prostate cancer | up |
| hsa-mir-98 | bronchioloalveolar carcinoma | down |
| hsa-mir-98 | colon cancer | down |
| hsa-mir-98 | esophageal squamous cell carcinoma | down |
| hsa-mir-98 | gastric cancer | up |
| hsa-mir-98 | glioma | down |
| hsa-mir-98 | hepatocellular carcinoma | down |
| hsa-mir-98 | lung cancer | down |
| hsa-mir-98 | nasopharyngeal carcinoma | down |
| hsa-mir-98 | neuroblastoma | down |
| hsa-mir-98 | pancreatic ductal adenocarcinoma | down |
| hsa-mir-99a | cervical carcinoma | down |
| hsa-mir-99a | esophageal squamous cell carcinoma | down |
| hsa-mir-99a | gastric cancer | up |
| hsa-mir-99a | hepatocellular carcinoma | down |
| hsa-mir-99a | lung adenocarcinoma | down |
| hsa-mir-99a | mesenchymal cancer | down |
| hsa-mir-99a | pancreatic cancer | up |
| hsa-mir-99b | lung cancer | down |
| hsa-mir-99b | cervical carcinoma | down |
| mmu-mir-290-3p | breast cancer | down |
| mmu-mir-290-5p | breast cancer | down |

Samples

In some embodiments, nucleic acids (e.g., DNA or RNA) are isolated from a biological sample containing a variety of other components, such as proteins, lipids, and non-template nucleic acids. Nucleic acid template molecules can be obtained from any material (e.g., cellular material (live or dead), extracellular material, viral material, environmental samples (e.g., metagenomic samples), synthetic material (e.g., amplicons such as provided by PCR or other amplification technologies)), obtained from an animal, plant, bacterium, archaeon, fungus, or any other organism. Biological samples for use in the present technology include viral particles or preparations thereof. Nucleic acid molecules can be obtained directly from an organism or from a biological sample obtained from an organism, e.g., from blood, urine, cerebrospinal fluid, seminal fluid, saliva, sputum, stool, hair, sweat, tears, skin, and tissue. Exemplary samples include, but are not limited to, whole blood, lymphatic fluid, serum, plasma, buccal cells, sweat, tears, saliva, sputum, hair, skin, biopsy, cerebrospinal fluid (CSF), amniotic fluid, seminal fluid, vaginal excretions, serous fluid, synovial fluid, pericardial fluid, peritoneal fluid, pleural fluid, transudates, exudates, cystic fluid, bile, urine, gastric fluids, intestinal fluids, fecal samples, and swabs, aspirates (e.g., bone marrow, fine needle, etc.), washes (e.g., oral, nasopharyngeal, bronchial, bronchialalveolar, optic, rectal, intestinal, vaginal, epidermal, etc.), and/or other specimens.

Any tissue or body fluid specimen may be used as a source for nucleic acid for use in the technology, including forensic specimens, archived specimens, preserved specimens, and/or specimens stored for long periods of time, e.g., fresh-frozen, methanol/acetic acid fixed, or formalin-fixed paraffin embedded (FFPE) specimens and samples. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA. A sample may also be isolated DNA from a non-cellular origin, e.g. amplified/isolated DNA that has been stored in a freezer.

Nucleic acid molecules can be obtained, e.g., by extraction from a biological sample, e.g., by a variety of techniques such as those described by Maniatis, et al. (1982) Molecular Cloning: A Laboratory Manual, Cold Spring Harbor, N.Y. (see, e.g., pp. 280-281).

In some embodiments, the technology provides for the size selection of nucleic acids, e.g., to remove very short fragments or very long fragments.

In some embodiments, the technology is used to identify a nucleic acid in situ. In particular, embodiments of the technology provide for the identification of a nucleic acid directly in a tissue, cell, etc. (e.g., after permeabilizing the tissue, cell, etc.) without extracting the nucleic acid from the tissue, cell, etc. In some embodiments of the technology related to in situ detection, the technology is applied in vivo, ex vivo, and/or in vitro.

Kits

Some embodiments are related to kits for the detection of a nucleic acid. For instance, in some embodiments are provided a kit comprising a solid support (e.g., a microscope slide, a bead, a coverslip, a biotin-conjugated microscope slide or coverslip, a solid support comprising a zero mode waveguide array, or the like), a capture probe, and a query probe as described herein. Some embodiments further provide software on a computer-readable format or downloadable from the internet for the collection and analysis of query probe binding events and dwell times as described herein. In some embodiments, kits for multiplex detection comprise two or more query probes each comprising a sequence complementary to a target nucleic acid and each comprising a different fluorescent moiety. In some embodiments, capture probes and query probes are complementary to capture regions and query regions of one or more miRNAs. Some embodiments of kits comprise one or more positive controls and/or one or more negative controls. Some embodiments comprise a series of controls having known concentrations, e.g., to produce a standard curve of concentrations.

Systems

Some embodiments of the technology provide systems for the detection and quantification of a target nucleic acid (e.g., a DNA, an RNA (e.g., a miRNA, a mRNA, a ncRNA)). Systems according to the technology comprise, e.g., a solid support (e.g., a microscope slide, a coverslip, a biotin-conjugated microscope slide or coverslip, a solid support comprising a zero mode waveguide array, or the like), a capture probe, and a query probe as described herein. Some embodiments further comprise a fluorescence microscope comprising an illumination configuration to excite bound query probes (e.g., a prism-type total internal reflection fluorescence (TIRF) microscope, an objective-type TIRF microscope, a near-TIRF or HiLo microscope, a confocal laser scanning microscope, a zero-mode waveguide, and/or an illumination configuration capable of parallel monitoring of a large area of the slide or coverslip (>100 $\mu m^2$) while restricting illumination to a small region of space near the surface). Some embodiments comprise a fluorescence detector, e.g., a detector comprising an intensified charge coupled device (ICCD), an electron-multiplying charge coupled device (EM-CCD), a complementary metal-oxide-semiconductor (CMOS), a photomultiplier tube (PMT), an avalanche photodiode (APD), and/or another detector capable of detecting fluorescence emission from single chromophores. Some embodiments comprise a computer and software encoding instructions for the computer to perform.

For example, in some embodiments, computer-based analysis software is used to translate the raw data generated by the detection assay (e.g., the presence, absence, or amount of one or more nucleic acids (e.g., one or more biomarkers such as miRNA(s)) into data of predictive value for a clinician. The clinician can access the predictive data using any suitable means.

For instance, some embodiments comprise a computer system upon which embodiments of the present technology may be implemented. In various embodiments, a computer system includes a bus or other communication mechanism for communicating information and a processor coupled with the bus for processing information. In various embodiments, the computer system includes a memory, which can be a random access memory (RAM) or other dynamic storage device, coupled to the bus, and instructions to be executed by the processor. Memory also can be used for storing temporary variables or other intermediate information during execution of instructions to be executed by the processor. In various embodiments, the computer system can further include a read only memory (ROM) or other static storage device coupled to the bus for storing static information and instructions for the processor. A storage device, such as a magnetic disk or optical disk, can be provided and coupled to the bus for storing information and instructions.

In various embodiments, the computer system is coupled via the bus to a display, such as a cathode ray tube (CRT) or a liquid crystal display (LCD), for displaying information to a computer user. An input device, including alphanumeric and other keys, can be coupled to the bus for communicating information and command selections to the processor. Another type of user input device is a cursor control, such as a mouse, a trackball, or cursor direction keys for communicating direction information and command selections to the processor and for controlling cursor movement on the display. This input device typically has two degrees of freedom in two axes, a first axis (e.g., x) and a second axis (e.g., y), that allows the device to specify positions in a plane.

A computer system can perform embodiments of the present technology. Consistent with certain implementations of the present technology, results can be provided by the computer system in response to the processor executing one or more sequences of one or more instructions contained in the memory. Such instructions can be read into the memory from another computer-readable medium, such as a storage device. Execution of the sequences of instructions contained in the memory can cause the processor to perform the methods described herein. Alternatively, hard-wired circuitry can be used in place of or in combination with software instructions to implement the present teachings. Thus, implementations of the present technology are not limited to any specific combination of hardware circuitry and software.

The term "computer-readable medium" as used herein refers to any media that participates in providing instructions to the processor for execution. Such a medium can take many forms, including but not limited to, non-volatile media, volatile media, and transmission media. Examples of non-volatile media can include, but are not limited to, optical or magnetic disks, such as a storage device. Examples of volatile media can include, but are not limited to, dynamic memory. Examples of transmission media can include, but are not limited to, coaxial cables, copper wire, and fiber optics, including the wires that comprise the bus.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

Various forms of computer readable media can be involved in carrying one or more sequences of one or more instructions to the processor for execution. For example, the instructions can initially be carried on the magnetic disk of a remote computer. The remote computer can load the instructions into its dynamic memory and send the instructions over a network connection (e.g., a LAN, a WAN, the internet, a telephone line). A local computer system can receive the data and transmit it to the bus. The bus can carry the data to the memory, from which the processor retrieves and executes the instructions. The instructions received by the memory may optionally be stored on a storage device either before or after execution by the processor.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In accordance with such a computer system, some embodiments of the technology provided herein further comprise functionalities for collecting, storing, and/or analyzing data (e.g., presence, absence, concentration of a nucleic acid such as a wiRNA). For example, some embodiments contemplate a system that comprises a processor, a memory, and/or a database for, e.g., storing and executing instructions, analyzing fluorescence, image data, performing calculations using the data, transforming the data, and storing the data. It some embodiments, an algorithm applies a statistical model (e.g., a Poisson model or hidden Markov model) to the data.

Many diagnostics involve determining the presence of, or a nucleotide sequence of, one or more nucleic acids (e.g., a nucleic acid biomarker such as a miRNA). Thus, in some embodiments, an equation comprising variables representing the presence, absence, concentration, amount, or sequence properties of multiple nucleic acids produces a value that finds use in making a diagnosis or assessing the presence or qualities of a nucleic acid. As such, in some embodiments this value is presented by a device, e.g., by an indicator related to the result (e.g., an LED, an icon on a display, a sound, or the like). In some embodiments, a device stores the value, transmits the value, or uses the value for additional calculations.

Thus, in some embodiments, the present technology provides the further benefit that a clinician, who is not likely to be trained in genetics or molecular biology, need not understand the raw data. The data are presented directly to the clinician in its most useful form. The clinician is then able to utilize the information to optimize the care of a subject. The present invention contemplates any method capable of receiving, processing, and transmitting the information to and from laboratories conducting the assays, information providers, medical personal, and/or subjects. For example, in some embodiments of the present technology, a sample is obtained from a subject and submitted to a profiling service (e.g., a clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center or subjects may collect the sample themselves and directly send it to a profiling center. Where the sample comprises previously determined biological information, the information may be directly sent to the profiling service by the subject (e.g., an information card containing the information may be scanned by a computer and the data transmitted to a computer of the profiling center using electronic communication systems). Once received by the profiling service, the sample is processed and a profile is produced that is specific for the diagnostic or prognostic information desired for the subject. The profile data are then prepared in a format suitable for interpretation by a treating clinician. For example, rather than providing raw expression data, the prepared format may represent a diagnosis or risk assessment for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor. In some embodiments, the information is first analyzed at the point of care or at a regional facility. The raw data are then sent to a central processing facility for further analysis and/or to convert the raw data to information useful for a clinician or patient. The central processing facility provides the advantage of privacy (all data are stored in a central facility with uniform security protocols), speed, and uniformity of data analysis. The central processing facility can then control the fate of the data following treatment of the subject. For example, using an electronic communication system, the central facility can provide data to the clinician, the subject, or researchers. In some embodiments, the subject is able to access the data using the electronic communication system. The subject may chose further intervention or counseling based on the results. In some embodiments, the data are used for research use. For example, the data may be used to further optimize the inclusion or elimination of markers as useful indicators of a particular condition associated with the disease.

EXAMPLES

During the development of embodiments of the technology described herein, experiments were conducted to detect nucleic acids at single-molecule resolution. In particular, experiments tested embodiments of the technology to detect miRNA molecules without nucleic acid amplification and without labeling the target nucleic acids. The data collected indicate that the technology provides advantages over extant techniques for detecting nucleic acids based on the formation of thermodynamically stable complexes.

Experiments were conducted to detect the transient binding of a fluorescent nucleic acid probe (e.g., a fluorescent query probe) to nucleic acid targets that were immobilized on a solid surface (e.g., the surface of a microscope slide) via hybridization to a nucleic acid capture probe (e.g., a locked nucleic acid (LNA oligonucleotide) capture probe) (see, e.g., FIG. 1A and FIG. 1B). The repetitive binding of fluorescent query probe molecules to the same target nucleic acid provides an increased confidence of the measurement due to increased sampling of the complementarity between target and query probe. The binding events occur as a Poisson process. Accordingly, the discrimination factor for detecting a target nucleic acid relative to background noise or the spurious binding of non-target nucleic acids increases exponentially with increasing acquisition time. The technology thus discriminates target nucleic acids form multiple closely related non-target nucleic acids in the same sample with substantially or effectively zero background signal.

Experiments were conducted to quantify five miRNAs present at picomolar and sub-picomolar concentrations in buffer solutions and in complex biological matrices. The data demonstrate that the technology is robust in detecting a variety of miRNA sequences in a variety of sample types, thus indicating the general application of the technology.

Materials and Methods

Experiments were performed using either a previously described prism-type total internal reflection fluorescence (TIRF) microscope (Michelotti et al (2010) "A Bird's Eye View: Tracking Slow Nanometer-Scale Movements of Single Molecular Nano-Assemblies" *Methods Enzymol* 475: 121-148) or an Olympus IX-81 objective-type TIRF microscope equipped with Cell^TIRF and focal drift control modules. For prism-type TIRF experiments, fluidic sample cells were constructed using two pieces of double-sided tape sandwiched between a quartz slide and glass coverslip as described (Michelotti, supra). For objective-type TIRF measurements, sample cells were constructed by fixing a 1-cm length of a pipet tip (Eppendorf) to a coverslip using epoxy adhesive (Double Bubble, Hardman Adhesives). For both techniques, the imaging surface (quartz slide or coverslip) was coated with a 1:10 mixture of biotin-PEG-550 and mPEG-550 (Laysan Bio, Inc.) immediately prior to construction of the sample cell as described (see, e.g., Abelson et al (2010) "Conformational dynamics of single pre-mRNA molecules during in vitro splicing" *Nat. Struct. Mol. Biol.* 17: 504-512). Prepared slides were stored in the dark for up to two weeks.

The synthetic miRNA targets were ordered from IDT with HPLC purification, except for hsa-let-7a, which was ordered from Dharmacon, and deprotected and HPLC purified according to the manufacturer's instructions. Fluorescent probes were ordered from IDT with HPLC purification. Capture probes were ordered from Exiqon with HPLC purification. The positions of LNA nucleotides (indicated by underlined letters in Table 2 and FIG. 1A) were chosen using the vendor's computational tools for LNA oligonucleotide self-structure and melting temperature prediction.

The sequences of RNA targets and probes are provided in Table 2:

TABLE 2

Sequences of RNA targets and probes

| | | SEQ ID NO: |
|---|---|---|
| miRNA Sequences | | |
| hsa-let-7a | /5'-P/UGAGGUAGUAGGUUGUAUAGUU | 1 |
| hsa-let-7c | /5'-P/UGAGGUAGUAGGUUGUAUGGUU | 2 |
| hsa-miR-16 | /5'-P/UAGCAGCACGUAAAUAUUGGCG | 3 |
| hsa-miR-21 | /5'-P/UAGCUUAUCAGACUGAUGUUGA | 4 |
| cel-miR-39 | /5'-P/UCACCGGGUGUAAAUCAGCUUG | 5 |
| Fluorescent Probe Sequences | | |
| $FP_{let-7a}$ | /5Cy3/ACTATACAAC | 6 |
| $FP_{miR-16}$ | /5Cy3/GCCAATATT | 7 |
| $FP_{miR-21}$ | /5Cy 5/TCAACATC | 8 |
| $FP_{miR-39}$ | /5Cy 5/AAGCTGATTT | 9 |
| Capture Probe Sequences | | |
| $CP_{let-7a}$ | TACTACCTCA/3Bio/ | 10 |
| $CP_{miR-16}$ | CGTGCTGCTA/3BioTEG/ | 11 |
| $CP_{miR-21}$ | CTGATAAGCTA/3BioTEG/ | 12 |
| $CP_{miR-39}$ | ACCCGGTGA/3BioTEG/ | 13 |

In Table 2, "CY3" represents a cyanine dye C3 linked to the oligonucleotide; "BIO" represents a biotin group linked to the oligonucleotide; "BIOTEG" represents a biotin group linked to the oligonucleotide with a spacer (e.g., a triethylene glycol spacer, e.g., typically a 15-atom triethylene glycol spacer); "5'-P" represents a 5-prime monophosphate group.

Quantification of synthetic miRNA targets was performed as follows. The slide surface was briefly incubated with T50 buffer (10 mM Tris-HCl (pH 8.0), 1 mM EDTA) followed by incubation with 1 mg/mL streptavidin. After 10 minutes, excess streptavidin was flushed out by 3 volumes of T50 buffer. The surface was then incubated with 20 nM of the appropriate biotinylated LNA oligonucleotide capture probe (Exiqon, Inc.) in 1×PBS buffer for 10 minutes and the excess flushed out by 3 volumes of 1×PBS. A 100-μL portion of a target RNA (let-7a, hsa-miR-16, hsa-miR-21, cel-miR-39, or hsa-miR-141) was introduced into the sample chamber and incubated for 10 minutes (prism-type TIRF) or 60 minutes (objective-type TIRF). In some embodiments, a longer incubation time was used for the objective-type TIRF measurements to collect data from the tall (~1-cm) sample cell, which slowed the rate of target immobilization on the imaging surface. An imaging buffer containing 4×PBS, 2.5 mM 3,4-dihydroxybenzoate, 25 nM protocatechuate dioxygenase, 1 mM Trolox, and 25 nM of the appropriate fluorescent query probe was added to the sample chamber. The transient binding of probes to the captured target nucleic acids was monitored for 10 to 40 minutes under illumination by 532 nm and/or 640 nm laser light. Imaging data were collected at a rate of 2 Hz using an iCCD or EMCCD.

Statistical and mathematical analysis (e.g., using custom MATLAB code) was used to identify sites of fluorescent probe binding and calculate intensity-versus-time trajectories from CCD movies. Intensity trajectories were subjected to hidden Markov modeling (HMM) using vbFRET15 or QuB16 to identify both the number of binding events and the dwell times in the bound state and unbound state for each candidate molecule. Based on control measurements acquired in the absence of target, a threshold of 10 binding+dissociation events was used to discriminate between target molecules and background binding. Additional filtering criteria were used to reject spurious transitions detected by the HMM software. In particular, to be counted as a target molecule, a candidate must: (1) have an intensity signal at least 2 standard deviations above the background intensity; and (2) exhibit a relatively constant probability of binding and dissociation events throughout the observation time, as determined by the correlation coefficient between event number and time, which must exceed 0.95.

Example 1—Detection of 20 pM Let-7a by Prism-Type TIRF Microscopy

Experiments conducted during the development of the technology provided herein demonstrated the detection of 20 pM let-7a by prism-type TIRF microscopy. A 20 pM solution of let-7a in 1×PBS was added to a microscope slide coated with an excess of the capture probe $CP_{let-7a}$. After a 10-minute incubation at room temperature, the sample chamber of the slide was flushed with imaging buffer (4×PBS, 2.5 mM 3,4-dihydroxybenzoate, 25 nM protocatechuate dioxygenase, 1 mM Trolox) containing 25 nM $FP_{let-7a}$. The transient binding of $FP_{let-7a}$ to the let-7a miRNA target was observed by prism-type TIRF microscopy for 10 min and analyzed by hidden Markov modeling (HMM) to count the number of intensity transitions in each single-molecule trajectory as described in the Materials and Methods.

Figure 2A:
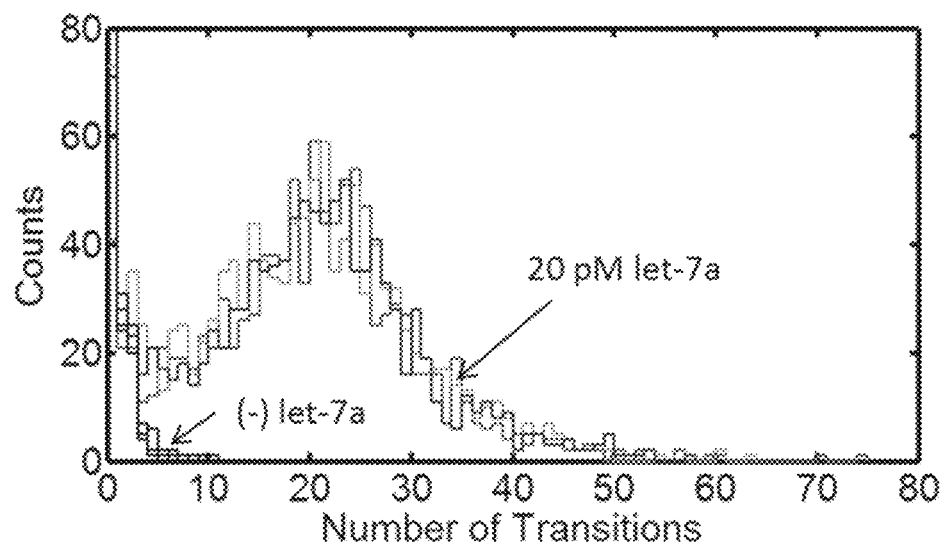
FIG. 2A is a histogram of intensity transitions for detection of 20 pM let-7a by prism-type TIRF microscopy.

A histogram of intensity transitions (e.g., probe association+dissociation events) per candidate molecule during a 10-minute observation window showed significant reproducibility between three different fields of view (FIG. 2A, three overlapped histograms noted "20 pM let-7a"). Further, the histogram showed significant separation of the let-7a binding events from the background noise (FIG. 2A, curves noted "(−) let-7a").

Figure 2B:
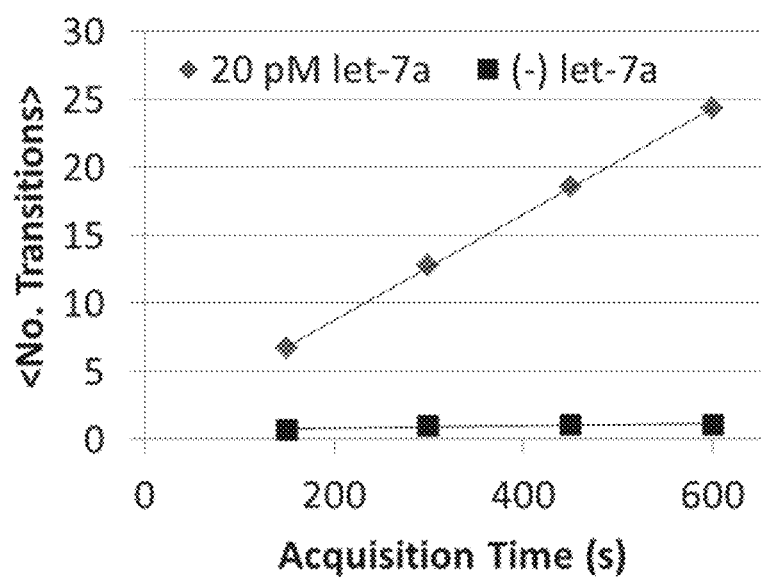
FIG. 2B is a plot showing the mean number of intensity transitions per candidate molecule for a target-positive assay and a negative control as a function of acquisition time for detection of 20 pM let-7a by prism-type TIRF microscopy.
Figure 2C:
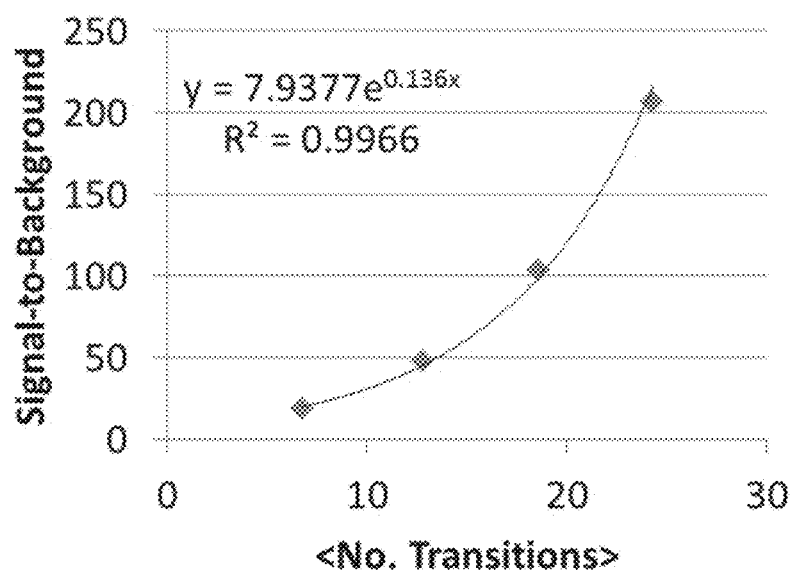
FIG. 2C is a plot showing the approximately exponential increase in signal-to-background ratio with increasing mean number of intensity transitions per candidate for detection of 20 pM let-7a by prism-type TIRF microscopy.

Analysis of the mean number of intensity transitions per candidate molecule for the target-positive assay (20 pM let-7a) and negative control as a function of acquisition time indicated that the mean number of transitions increased linearly with respect to time in both cases (FIG. 2B). Further, the signal-to-background ratio increased approximately exponentially as the mean number of intensity transitions per candidate increased (FIG. 2C). The signal-to-background ratio was calculated using a threshold defined as one standard deviation below the mean number of transitions in the positive assay.

Figure 2D:
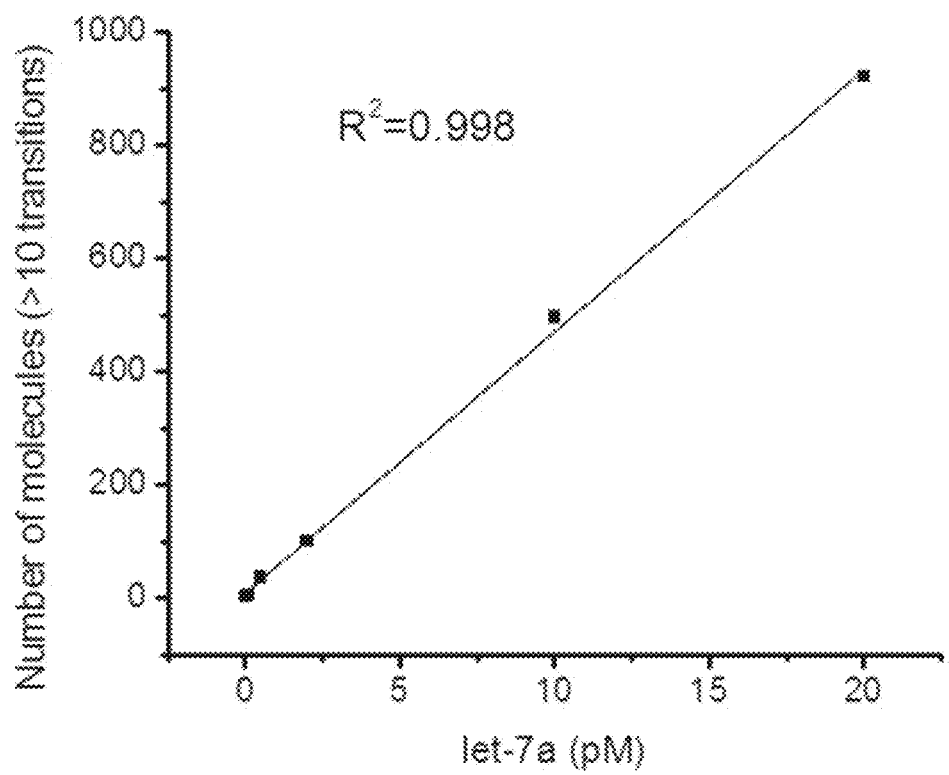
FIG. 2D is a plot showing a linear relationship between concentration of miRNA and number of molecules detected by an embodiment of the technology provided herein.

In addition, samples having known concentrations of let-7a miRNA (e.g., 0 to 20 pM; see FIG. 2D) were examined to assess the relationship of concentration with number of molecules detected by the method. The number of immobilized molecules observed to undergo at least 10 transitions and that were confirmed by the filtering criteria described herein to be target nucleic acid (let-7a) were plotted against the previously measured concentration of let-7a in the sample (FIG. 2D). The number of let-7a molecules enumerated by the technology was linearly related (e.g., with a correlation coefficient $R^2$ of 0.998) to the known concentrations of let-7a assayed. Accordingly, these data indicate that standard solutions and standard curves find use with the technology, e.g., to determine the concentration of a sample having an unknown concentration of a target nucleic acid (e.g., a miRNA).

Example 2—Single-Nucleotide Mismatch Discrimination

During the development of embodiments of the technology provided herein, experiments were conducted to detect a target nucleic acid (e.g., a miRNA) comprising a single nucleotide difference relative to a non-target nucleic acid. In particular, the technology was used to discriminate between two members of the let-7 family of microRNAs, let-7a and let-7c, which differ from each other at one nucleotide position. The sequences of the let-7a and let-7c miRNAs are provided in Table 2. The miRNAs were synthesized with a 5' phosphate as indicated in the Table 2 by "/5'-P/".

A 10 pM solution of let-7a or let-7c in 1×PBS was added to a microscope slide coated with an excess of the capture probe $CP_{let-7a}$. let-7a. After a 10-minute incubation at room temperature, the sample chamber of the slide was flushed out with imaging buffer (4×PBS, 2.5 mM 3,4-dihydroxybenzoate, 25 nM protocatechuate dioxygenase, 1 mM Trolox) containing 25 nM FP let-7a. let-7a. After binding let-7a or let-7c miRNA to the surface-immobilized capture probe to form a thermodynamically stable complex, the immobilized let-7a or let-7c miRNA was queried with a 10-nt fluorescent query probe labeled at the 3' end with a fluorescent moiety (e.g., CY5 dye). The probe is completely complementary to nucleotides 12-21 of the let-7a sequence and comprises a single mismatch to nucleotides 12-21 of the let-7c sequence (see Table 2).

The transient binding of FP let-7a let-7a to the let-7a and let-7c miRNA targets was observed by prism-type TIRF microscopy for 10 minutes and analyzed by hidden Markov modeling as described in the Materials and Methods. Representative single-molecule intensity-versus-time traces collected in the presence of let-7a and let-7c are shown in FIG. 3A and FIG. 3B, respectively.

Figure 3A:
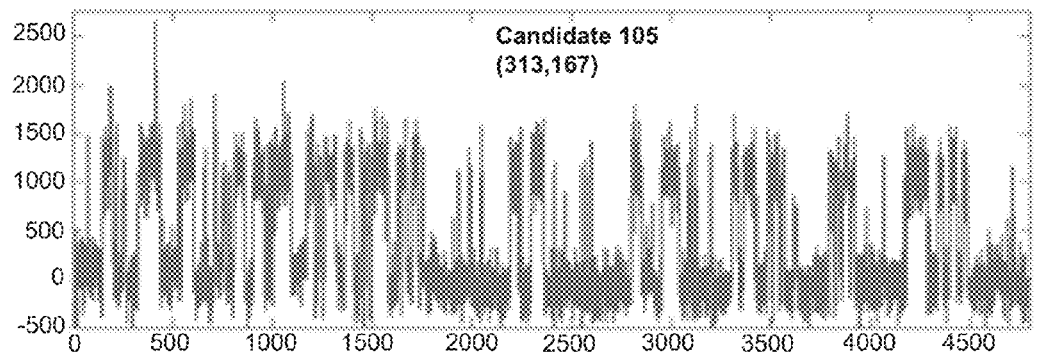
Figure 3B:
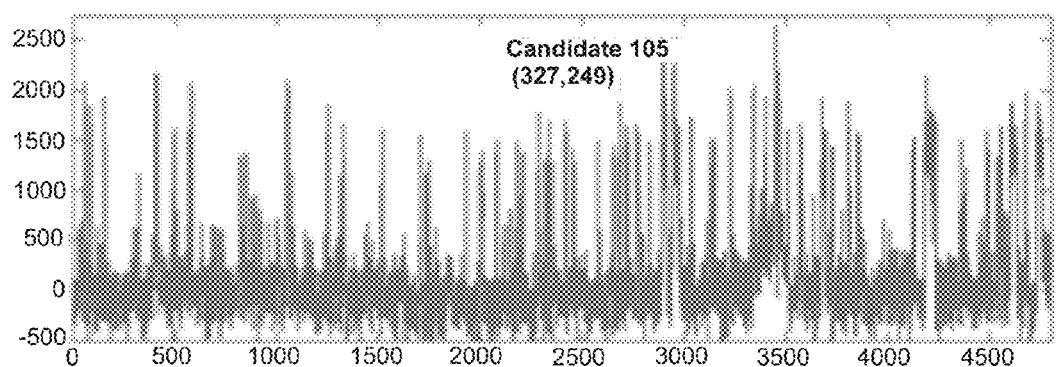
FIG. 3B shows data from an experiment using the same probe in FIG. 3A to detect let-7c, which has a single mismatch to the probe; the single mismatch causes the fluorescent probe to dissociate ~4 times more rapidly from let-7c than it does from let-7a in FIG. 3A.

Data collected during the experiments indicated that the 10-nt query probe bound for longer times (e.g., approximately 15 seconds) to the let-7a nucleic acid relative to the let-7c nucleic acid (FIG. 3A and FIG. 3B). The single base difference of the let-7c nucleic acid causes the query probe to dissociate approximately 4 times more rapidly from the let-7c nucleic acid than the query probe dissociates from the let-7a nucleic acid (FIG. 3a and FIG. 3B).

Figure 3C:
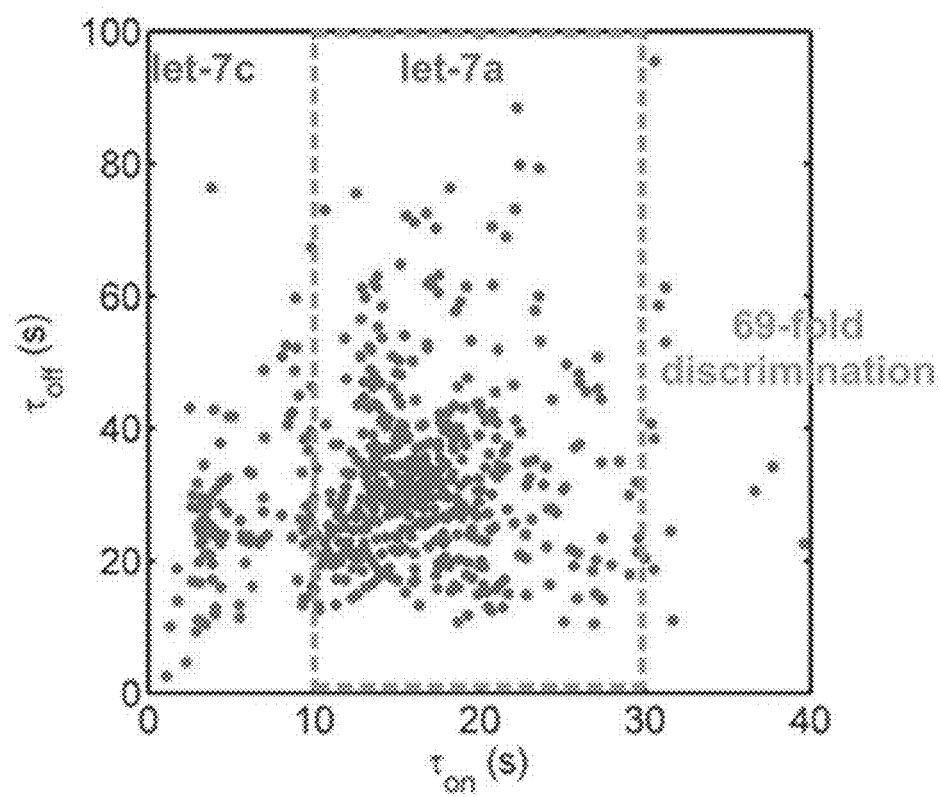
FIG. 3C is a plot showing approximately 70-fold discrimination between let-7a and let-7c using the same fluorescent probe.

The average dwell times in the bound and unbound states ($\tau_{on}$ and $\tau_{off}$, respectively) was calculated for each molecule (FIG. 3C). Based on the distribution of dwell times for let-7a and let-7c, a box was drawn to include the majority of let-7a dwell times while excluding most of those for let-7c (dotted line in FIG. 3C); this box contains approximately 70 times more dwell times from the let-7a than from the let-7c experiment, yielding an estimate of the capacity of the technology for single-nucleotide discrimination.

Example 3—Detection of Let-7a in Human Cell Extracts

Figure 4A:
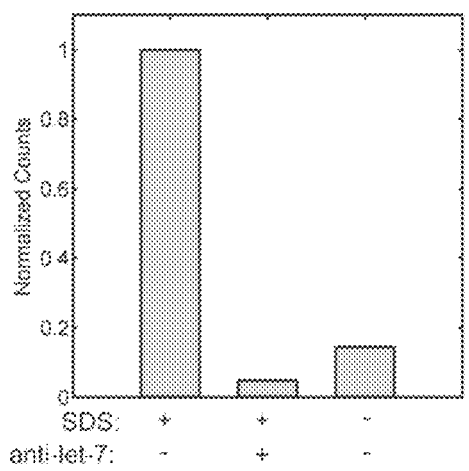
FIG. 4A is a bar plot showing the detection of let-7a in HeLa whole cell lysate.

During the development of embodiments of the technology described herein, experiments were conducted to detect let-7a in extracts prepared from human cells. A small aliquot of HeLa whole cell extract (from Thermo Scientific In-Vitro Protein Expression Kit, #88881) was incubated for 5 minutes at room temperature in the presence of 0 or 1.7% sodium dodecyl sulfate (SDS) and 0 or 140 nM miRCURY let-7a inhibitor (Exiqon). The lysate was vortexed, diluted 100-fold in imaging buffer containing 25 nM of the fluorescent probe $FP_{let-7a}$, and added to a microscope slide coated with an excess of the capture probe $CP_{let-7a}$. After a 10-minute incubation, the transient binding of $FP_{let-7a}$ to the let-7a miRNA target was observed by prism-type TIRF microscopy for 10 minutes and analyzed by hidden Markov modeling as described in the Materials and Methods. A threshold of 10 intensity transitions (binding+dissociation or photobleaching events) per candidate molecule was used to distinguish between target molecules (let-7a) and nonspecific background association of the probe to the imaging surface. The number of molecules found in each experiment was normalized to the experiment in the presence of SDS treatment but in the absence of the anti-let-7 LNA oligonucleotide (FIG. 4A). In the experiments, the data show that more let-7a was detected in samples treated with SDS than samples that were not treated with SDS (FIG. 4A); further, the data show that addition of the anti-let-7 locked nucleic acid oligonucleotide decreased the amount of let-7a that was detected in the samples (FIG. 4A).

In additional experiments, cultured U2OS cells were transfected with duplex hsa-let-7-a1 miRNA using Lipofectamine 2000 (Life Technologies) according to the manufacturer's protocol. The cytoplasmic fraction of U2OS cells was isolated as follows: cells were scraped into ice-cold phosphate-buffered saline (PBS) and centrifuging at 100×g for 10 minutes at 4° C. The supernatant was discarded and the cell pellet was resuspended by gentle pipetting in 200 µL ice-cold lysis buffer (10 mM Tris pH 8.0, 140 mM NaCl, 1.5 mM $MgCl_2$, 1% Nonidet P-40). After incubating on ice for 5 minutes, the suspension was centrifuged at 1,000×g for 3 minutes at 4° C. The supernatant containing the cytoplasmic fraction was recovered and total RNA was extracted using TRIzol reagent (Life Technologies) according to the manufacturer's directions. Non-transfected U2OS cells were also fractionated and TRIzol-extracted to recover cytoplasmic RNA. TRIzol-extracted RNA fractions were resuspended to a concentration of 1 mg/mL RNA (estimated by UV absorbance at 260 nm) in 10 mM Tris, pH 8.0 and stored at −20° C. until use.

Figure 4B:
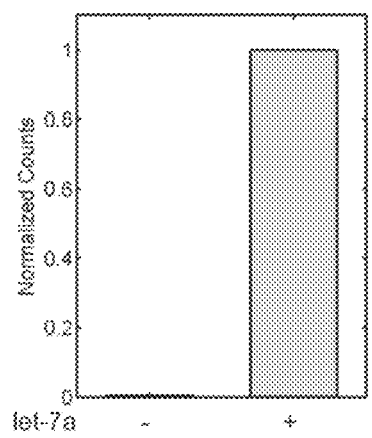
FIG. 4B is a bar plot showing the detection of let-7a in U2OS cytosolic RNA isolate.

For analysis of the samples according to the technology, the U2OS cytoplasmic RNA extract was diluted either 10-fold (for non-transfected cell extract) or 100-fold (for transfected cell extract) in imaging buffer containing 25 nM $FP_{let-7a}$ and added to a microscope slide coated with an excess of the capture probe $CP_{let-7a}$. let-7a. After a 10-minute incubation, the transient binding of $FP_{let-7a}$ to let-7a was observed by prism-type TIRF microscopy for 10 minutes and analyzed by hidden Markov modeling as described in the Materials and Methods. A threshold of 10 intensity transitions (binding+dissociation or photobleaching events) per candidate molecule was used to distinguish between target molecules (let-7a) and background binding to the imaging surface. After correcting for dilution, the number of molecules found in each experiment was normalized to the number of let-7a molecules detected in the extract from transfected U2OS cells (FIG. 4B). After imaging and quantification, the data indicated that let-7a was detected in the preparations from transfected cells but was not detected in the preparations from cells that were not transfected (FIG. 4B).

Example 4—General Applicability of the Technology

During the development of embodiments of the technology provided herein, experiments were conducted applying the technology to detect a wide variety of miRNA species. Data were collected from experiments using three different miRNA targets from *H. sapiens*: hsa-let-7a (FIG. 5A), hsa-miR-16 (FIG. 5B), and hsa-miR-21 (FIG. 5C); and one miRNA target from *C. elegans*: cel-miR-39 (FIG. 5D). The data indicated repeated probe binding and intensity transition histograms were compiled for the detection of the four different targets.

In each of FIG. 5A to FIG. 5D, the top sequences represent the miRNA targets, the sequences beneath the miRNA targets and complementary to the left portion of the miRNA targets represent the locked nucleic acid capture probes, and the sequences beneath the miRNA targets and complementary to the right portion of the miRNA targets represent the transiently binding fluorescent DNA probes (e.g., labeled with Cy 5). The underlined letters in the capture probe sequences signify LNA nucleotides rather than DNA nucleotides. In the intensity transition histograms (right column of plots), the leftmost curve (starting at a high value then decreasing from left to right) represents the number of locations in the field of view (e.g., candidate molecules) with a given number of intensity transitions in the absence of the miRNA target (e.g., background binding to the surface and/or capture probe), while the rightmost distribution ("bell shaped") curve represents the number of candidate molecules with a given number of intensity transitions in the presence of 1 pM miRNA target. While different target/probe combinations yield different binding and dissociation kinetics, as well as different positions for the positive signal peak in the transition histograms, the positive peak in the histogram is well separated from the background signal in all cases. Data were collected and analyzed as reported in the Materials and Methods, with an acquisition time of 10 minutes.

Example 5—Detection of miR-141 in Crude Serum

During the development of embodiments of the technology provided herein, experiments were conducted to investigate use of the technology for detecting miRNAs of clinical interest in minimally treated (e.g., "crude") biofluids. In particular, the technology was used to detect the prostate cancer biomarker hsa-miR-141 in a serum sample from a healthy individual after spiking in varying concentrations of synthetic hsa-miR-141. In these experiments, 50 µl of freshly thawed human serum (BioreclamationIVT, #BRH844152) was combined with SDS (final 2% w/v), proteinase K (New England BioLabs, Inc., P8107S; final concentration 0.16 units/µl), and synthetic hsa-miR-141, and the mixture was incubated for 15 minutes at room temperature. Next, EDTA was added to a final concentration of 20 mM and the sample was heated to 90° C. for 2 minutes. After cooling to ambient (e.g., room) temperature for 5 minutes, each sample was allowed to bind to a microscope coverslip surface for 1 hour. Residual serum was removed, the surface washed with 1×PBS, and imaging carried out by objective-type TIRF microscopy as described herein.

To evaluate the accuracy of the assay, the nominal spiked-in concentration was compared to the concentration calculated using a standard curve collected in buffer, resulting in a strong correlation (R>0.999) and a high recovery factor (slope=1.07 from a linear regression). While miR-141 is elevated in the serum of patients with metastatic prostate cancer, it is expected to be present at low levels (e.g., 0.1-5 fM) in healthy individuals. Consistent with this expectation, the measured concentration of hsa-miR-141 was 0.4±0.5 fM (s.e.m., n=3) in serum specimens in the absence of spiked-in synthetic miR-141.

Example 6—Measuring Nucleic Acid Conformation

During the development of embodiments of the technology provided herein, experiments were conducted to observe changes in the conformation of a nucleic acid as a function of the concentration of a ligand that binds to the nucleic acid. In particular, experiments were conducted to test the accessibility of a Shine-Dalgarno (SD) sequence of a messenger RNA comprising a non-coding functional element (e.g., a "riboswitch") that binds a ligand (e.g., the modified nucleotide7-aminomethyl-7-deazaguanine, "preQ$_1$"). In these experiments, the target nucleic acid comprises a Shine-Dalgarno sequence and a preQ$_1$ riboswitch. The target nucleic acid is immobilized to a surface (e.g., using a capture probe). A query probe (e.g., a short, fluorescently labeled RNA probe) is used that is complementary to the Shine-Dalgarno sequence. Then, using total internal reflection fluorescence microscopy-based observation of transient query probe binding events as a function of ligand concentration, data were collected that indicated that apparent decreases in both the probe binding and dissociation rate constants are due to complex changes in Shine-Dalgarno sequence accessibility in single mRNA molecules. Data collected showing the association of nucleic acid conformational state with the concentration of ligand provide for the quantification of the bound ligand and unbound ligand in the experiments.

For these experiments, genomic sequences were downloaded from the National Center for Biotechnology Information (www.ncbi.nlm nih.gov). The complete mRNA, including the TTE1564 and TTE1563 ORFs, and the 3' UTR as predicted from the FindTerm algorithm (SoftBerry), was amplified from *Thermoanaerobacter tengcongensis* genomic DNA, which was purchased from the NITE Biological Resource Center. The mRNA was cloned into pUC19 with an engineered T7 promoter at the 5' end between the BamHI and HindIII sites of pUC19. mRNA was produced by in vitro transcription. The Tte pUC19 plasmid was linearized with HindIII (AflII or XbaI for in vitro translation assays) (New England Biolabs) for run-off transcription. Similarly, the pAMB CAT plasmid was linearized with FspI (New England Biolabs). Transcription reactions were performed in the presence of 120 mM HEPES-KOH, pH 7.5, 25 mM MgCl$_2$, 2 mM spermidine, 40 mM DTT, 30 mM NTPs, 0.01% Triton X-100, 200 nM linearized plasmid, 0.01 U/µl pyrophosphatase and 0.07 mg/mL T7 RNA polymerase in a total volume of 1 mL. mRNAs for in vitro translation assays were also prepared using the MEGAscript T7 transcription kit (Life Technologies). Transcription reactions were incubated at 37° C. for 4 hours. Enzyme was removed by phenol/chloroform extraction and the resulting solution was spun in an Amicon 100 MWCO spin column to reduce the volume to ~100 µl. mRNA was purified by denaturing PAGE purification, detected using 254 nm UV radiation and gel eluted overnight. mRNAs were ethanol precipitated and resuspended in TE buffer at pH 7.0.

4 nM Tte mRNA, TYE563-LNA, and biotin capture strand were heat annealed at 70° C. for 2 minutes in the presence of 50 mM Tris-HCl, pH 7.5, 0.6 M NaCl and 20 mM $MgCl_2$, and allowed to slow cool to room temperature for 20 minutes in the presence or absence of $preQ_1$. Following slow cooling, the RNA mix was diluted to 40 pM in the same buffer in the presence or absence of $preQ_1$, with a 10× excess of TYE563-LNA and biotin capture strand to stabilize the complex during dilution. The diluted complex was chilled on ice. The chilled solution was flowed over an assembled microfluidic channel on a quartz slide coated with biotinylated-BSA and streptavidin. 100 µl of the chilled, 40 pM RNA complex was flowed over the slide and allowed to equilibrate for 5 minutes. Excess RNA was washed off the slide with buffer in the presence and absence of $preQ_1$. An oxygen scavenging system consisting of 5 mM protocatechuic acid and 50 nM protocatechuate-3,4-dioxygenase in the presence and absence of $preQ_1$ (to slow photobleaching), 2 mM Trolox (to reduce photoblinking), and 50 nM Cy5-probe was flowed over the slide and allowed to equilibrate for 5 minutes.

Both CY5 and TYE563 dyes were directly excited simultaneously using a 638-nm red diode laser and 523-nm green laser, respectively. Emission from both fluorophores was simultaneously recorded using an intensified CCD camera (I-Pentamax, Princeton Instruments) at 100 ms time resolution using Micro-Manager software. Fluorescence traces were extracted from the raw movie files using IDL (Research Systems) and analyzed using Matlab (The Math Works) scripts. Genuine traces exhibiting binding were manually selected using the following criteria: a single photobleaching step of the TYE563 signal, TYE563 fluorescence intensity of >200 intensity units, and at least two binding events per trajectory with a signal to noise ratio of at least 3:1. Suitable traces were compiled. Hidden Markov Modeling analysis was performed on the donor intensity using the segmental k-means algorithm in the QuB software suite. A two-state model was used with an unbound and bound state to idealize the data. Transition density plots were constructed to extract the dwell times in the bound and unbound states. Bound dwell times were fit to a double exponential and unbound dwell times were fit to a single exponential in OriginLab 8.1 from which on and off rates were calculated.

The SD sequence is a short (3 to 8 nt), purine-rich sequence located approximately 5 to 8 nt upstream of the start codon of bacterial mRNAs. It interacts with a complementary sequence at the 3' end of 16S ribosomal RNA (rRNA) during translation. The SD sequence of the *Thermoanerobacter tengcongensis* ("Tte") gene TTE1564 is located within a $preQ_1$ riboswitch structure in the TTE1564 messenger RNA. Gene prediction tools find that the open reading frame (ORF) of TTE1564 overlaps with downstream gene TTE1563 (7-cyano-7-deazaguanine reductase, queF), where the SD sequence of the downstream gene TTE1563 is located at the 3' end of the TTE1564 ORF. In vitro translation assays show that both protein products are translated.

To observe changes in SD sequence accessibility as a function of ligand concentration, data were collected using the technology described herein. In the exemplary embodiment of the technology used in the experiments, the technology comprised use of a short, fluorescently (CY5 dye) labeled anti-SD RNA query probe comprising a sequence that was the same as the 12 nt at the 3' end of Tte 16S rRNA. Single target mRNA molecules were hybridized to a high-melting temperature TYE563-labeled locked nucleic acid (LNA oligonucleotide) for visualization and immobilized on a quartz slide at low density via a biotinylated capture probe. Experiments were imaged by total internal reflection fluorescence microscopy. The TYE563-labeled LNA oligonucleotide covers and sequesters the SD sequence and start codon of the downstream TTE1563 ORF. For visualization, TYE563 fluorescence is only observed once all three components (immobilized biotinylated capture probe, mRNA, and TYE563-LNA) are annealed.

The hybridization between the Tte mRNA and the anti-SD query probe comprises five complementary Watson-Crick base pairs; thus, binding of the query probe to a single mRNA SD sequence is reversible and transient. Additionally, the use of TIRFM provides signal detection wherein query probe molecules that are transiently immobilized by binding to the mRNA target are observed within the evanescent field and query probes diffusing freely in solution provide only a distinguishable, modest background fluorescence signal. Repeated and transient diffraction-limited colocalization of the CY5 dye and TYE563 fluorescence unambiguously characterizes binding of the query probe to the target mRNA molecule. Further, the characteristic repeated signals report on the accessibility of the SD sequence of individual mRNA molecules to the complementary (e.g., anti-SD) sequence of 16S rRNA in a quantitative fashion since changes in the probe binding and dissociation time constants can be sensitively monitored over an arbitrarily long time window.

Example 7—Measuring Ligand Binding to Nucleic Acid

The Tte preQ1 riboswitch structure is partially open in the absence of $preQ_1$, leaving the SD sequence more exposed than in the presence of ligand. Accordingly, during the development of embodiments of the technology provided herein, experiments were conducted to measure the accessibility of the SD sequence in the absence and presence of $preQ_1$. In particular, CY5 dye-labeled anti-SD RNA query probe was flowed onto a slide with capture-probe immobilized target nucleic acid (e.g., target mRNA) in the absence of ligand. During visualization and data collection, thousands of transient binding events were observed in over 100 mRNA molecules per experiment, thus demonstrating the highly parallel nature of embodiments of the technology.

Figure 6A:
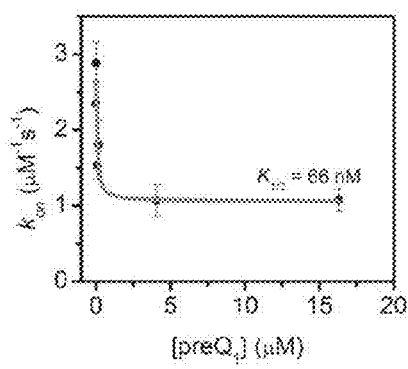
FIG. 6A shows a plot in which the dwell times in the unbound state across all preQ$_1$ concentrations were compiled and plotted with an exponential fit, plotted as a function of ligand concentration, and fit to a logistic fit. The corresponding K$_{1/2}$ value is indicated. Each concentration was tested experimentally at least three times.
Figure 6B:
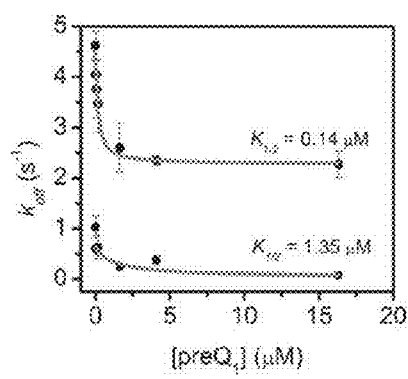
FIG. 6B shows a plot in which the dwell times in the bound state across all preQ$_1$ concentrations were compiled and plotted. Each individual condition was plotted as a double exponential. The corresponding K$_{1/2}$ values are indicated.
Figure 6C:
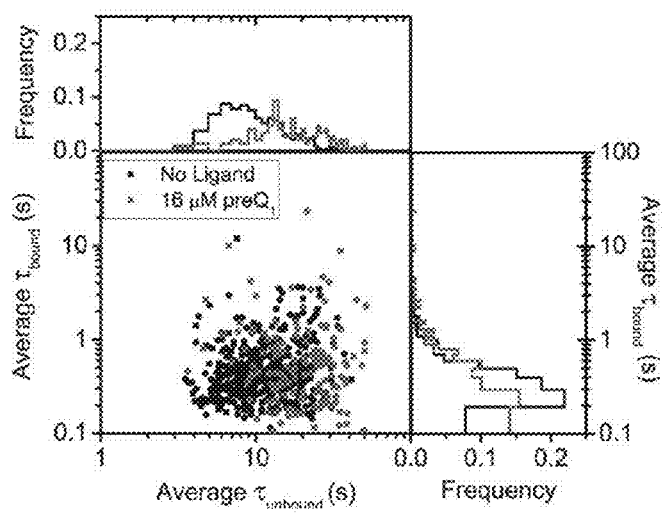
FIG. 6C is a plot showing the correlation between the average bound and unbound time of each individual trajectory and the corresponding histograms in the presence and absence of ligand.

The CY5 dye emission trajectory was fit using a two-state Hidden Markov Model to extract dwell times of the probe in the bound and unbound states, $\tau_{on}$ and $\tau_{off}$, respectively. Finally, the dwell times were fit to a single exponential to calculate the $k_{on}$ and a double exponential function was used to extract a $k_{off}$ comprising two components, e.g., a "fast" $k_{off}$ and a "slow" $k_{off}$, consistent with the results from analysis of the residuals. In the absence of ligand, the anti-SD query probe binds with a rate constant, $k_{on}$ of 2.4±0.3 $\mu M^{-1} s^{-1}$ (FIG. 6A). The probe exhibits biphasic dissociation kinetics, with a fast rate constant of 4.6±0.3 $s^{-1}$ and a slow rate constant of 1.0±0.2 $s^{-1}$ (FIG. 6B).

During the development of embodiments of the technology provided herein, experiments were conducted to measure the conformational change of the Tte RNA and occlusion of the SD sequence upon adding preQ$_1$. In particular, RNA molecules were folded in the presence of varying concentrations of preQ$_1$ and assessed according to the technology described herein. The data collected indicated that the value of k$_{on}$ of the anti-SD query probe decreased as the concentration of preQ$_1$ was increased with a half-saturation point of 0.37 μM preQ$_1$ (FIG. 6A). Since query probe binds when the SD sequence is exposed, a decrease in the rate of binding indicates an occlusion of this target sequence when preQ$_1$ is present. Further (and unexpectedly), an increase in preQ$_1$ concentration produced a slight decrease (e.g., less than 2-fold at a saturating preQ$_1$ concentration) in both the fast and slow k$_{off}$ rate constants (FIG. 6B), indicating that preQ1 stabilizes the interaction of the SD sequence with the anti-SD query probe sequence. Further, the kinetic data indicating a change in the conformational state of the nucleic acid also provide for the quantification of the ligand in the bound and unbound states.

In additional experiments conducted during the development of embodiments of the technology, data were collected that confirmed that the kinetic change was due to conformational rearrangements localized to the SD sequence of the riboswitch. In particular, experiments were performed using a negative control query probe that was complementary to a sequence within the mRNA ORF, which the experiments indicated was unaffected by preQ$_1$ concentration. In particular, the kinetics of the negative control query probe binding showed little dependence on preQ$_1$, indicating that the conformational changes observed due to ligand binding were localized to the TTE1564 SD sequence overlapping the riboswitch.

Further inspection of individual query probe binding trajectories revealed that single molecules seemed to interconvert between periods of frequent query probe binding and periods of more sporadic query probe binding, which can be interpreted as periods of high and low SD accessibility, respectively. Traditional methods of analysis failed to detect these changes in intramolecular behavior. For instance, a plot of the mean query probe bound and unbound times of all molecules in the absence of preQ$_1$ ligand and at saturating preQ$_1$ ligand revealed a slight shift in the 16 μM preQ$_1$ ligand population towards longer unbound times; however, all molecules generally fit within a single population. While these traditional approaches have proven sufficient for revealing heterogeneity within a single population of molecules, they fail to uncover heterogeneous behavior within a single molecule.

The probe binding events detected via the technology described herein strongly resembled neuronal spike trains, where neuronal firing is monitored and detected as sharp increases (or "spikes") in electrical activity in response to external stimuli. A common feature of these spike trains is short intervals of high firing activity (or "bursts") separated by periods of inactivity. Accordingly, in some embodiments the data were treated by a spike train analysis to detect and separate the periods of high and low SD accessibility within single molecules. In some embodiments, a Rank Surprise (RS) method of burst detection was applied to the data, e.g., due to its nonparametric approach. Indeed, when automatic burst detection was performed on single molecule trajectories in the absence of ligand, individual molecules displayed detectable bursts of anti-SD query probe binding behavior separated by non-bursting periods characterized by areas of average lower binding activity (FIG. 7A). When the duration of the interspike intervals (ISIs) in the bursting and non-bursting periods were plotted, two distinct intramolecular behaviors were evident (FIG. 3B), which were not detected using traditional kinetic analyses, indicating that these behaviors are distinguished by the duration of their ISIs. Single molecules tend to interconvert between periods of bursting and non-bursting behavior, rather than separate subpopulations of highly- and poorly-accessible molecules, respectively. This suggests that the SD sequence of the Tte riboswitch undergoes binary switching between two different conformational states: a "bursting" state with overall high SD accessibility and marked by frequent binding of the anti-SD query probe and short ISIs, and a "non-bursting" state characterized by low SD accessibility where the SD sequence is sequestered from query probe binding even in the absence of ligand. During this non-bursting state, anti-SD query probe still binds to the SD sequence, although less frequently than during the bursting state, resulting in longer ISI times (FIG. 7B).

Example 8—Effect of Ligand on Nucleic Acid Dynamics

Figure 8A:
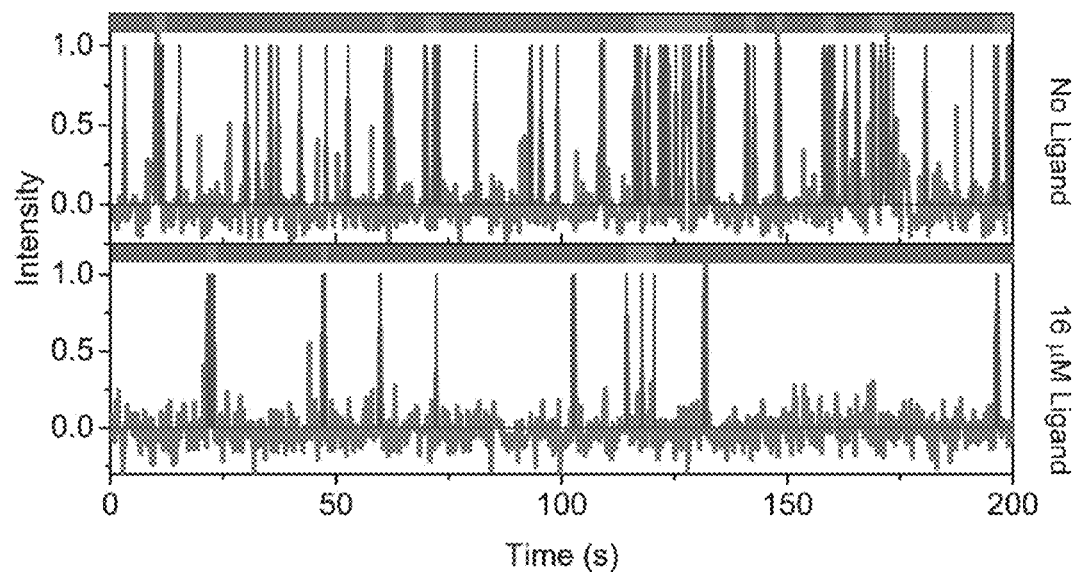
FIG. 8A shows histograms indicating the time spent in the unbound states inside and outside of the burst at varying ligand (e.g., preQ$_1$) concentrations.
Figure 8B:
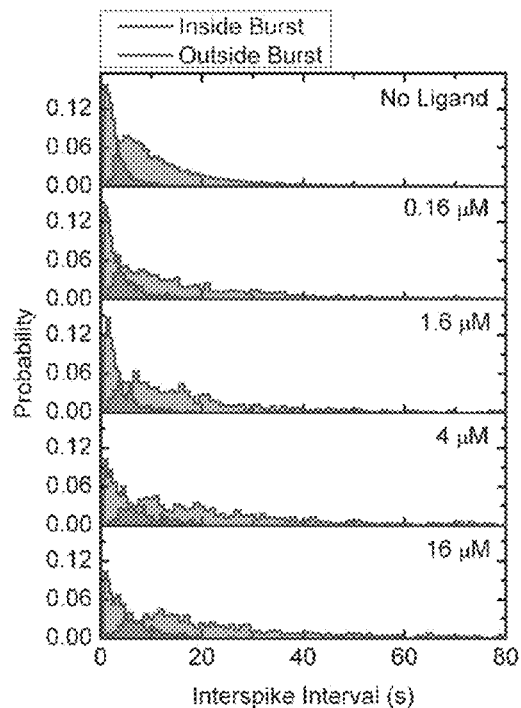
FIG. 8B shows histograms indicating the length of each burst.
Figure 8C:
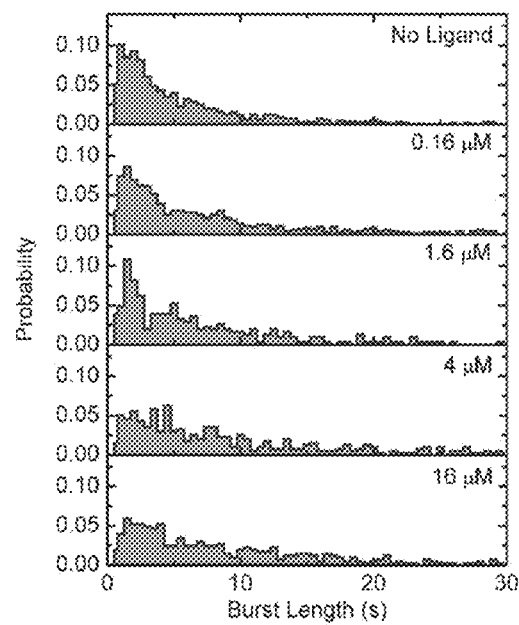
FIG. 8C shows representative trajectories in the absence (top panel) and presence (bottom panel) of ligand.

Spike train analysis has shown that the Tte preQ$_1$ riboswitch displays periods of non-bursting behavior and low SD accessibility, even in the absence of ligand. Accordingly, experiments were conducted during the development of embodiments of the technology to investigate whether conformational bursting occurs in the presence of the preQ$_1$ ligand. In particular, experiments were performed using spike train analysis on the trajectory data collected in the presence of ligand. This analysis identified bursts of SD sequence accessibility even at saturating ligand concentrations (FIG. 8A). Upon visual inspection of the trajectories at high ligand concentration, the data indicated the presence of a lower frequency of anti-SD binding events within each burst, along with longer non-bursting periods compared to low ligand concentration (FIG. 8A). As ligand concentration is increased, both the ISIs in the bursting and non-bursting populations increased (FIG. 8B). In other words, the conformation in which the SD sequence is occluded from anti-SD query probe binding in the bursting and non-bursting populations is longer lived when preQ$_1$ is present. As a direct result of this, the average lifetime of each bursting population increased as preQ$_1$ was added (FIG. 8C). This change, however, is not due to an increase in the individual anti-SD query probe binding event spikes per burst, as this metric did not change with preQ$_1$ concentration. Taken together, these results indicate that the Tte preQ$_1$ riboswitch transitions between two different conformational states, one in which the SD sequence is exposed and available for frequent binding to the anti-SD sequence and one in which the SD sequence is occluded from anti-SD binding. Both these states exist in the presence and absence of ligand and appear in bursts. As preQ$_1$ is added, the transitions between these states occur more slowly, providing for a shallow regulatory response, rather than an abrupt ON/OFF response.

Further, data collected indicated that the Tte preQ$_1$ riboswitch accesses two conformational states, where the SD sequence is accessible in periods of bursts separated by periods of, on average, less accessibility. Accordingly, experiments were conducted during the development of embodiments of the technology to investigate the bursting behavior of a single molecule in response to ligand concentration. Experiments were performed in which the anti-SD query probe binding behavior was observed for single riboswitch-containing mRNA molecules in the absence of ligand. Without adjusting the field of view, 16 μM preQ$_1$ was flowed over the slide. Following sufficient observation, the preQ$_1$ was washed out of the channel, followed by observation once again. This procedure allowed observation and data collection relating to the structural changes of single molecules in response to different preQ$_1$ concentrations. Burst analysis was performed on 97 mRNA molecules and compiled in a chimograph. The molecules were clustered based on the fraction in the bursting state and ordered accordingly in the chimograph. The results indicate that a small fraction of molecules (11 out of 97) transition from a mostly bursting state to a non-bursting state and finally back to a bursting state. The majority of molecules (47 out of 97) begin in a predominantly non-bursting state without transitioning to the bursting state. These results further highlight the stochastic regulatory response of the preQ$_1$ ligand and suggest that the process of riboswitching may contribute to the probabilistic nature of bacterial gene regulation.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method for detecting a target nucleic acid in a sample, the method comprising:
   a) immobilizing a single target nucleic acid molecule from the sample to a discrete region of a solid support and providing detectably labeled query probes that associate and dissociate with said single target nucleic acid according to a kinetic rate constant $k_{on}$ or $k_{off}$ that is greater than 1 min$^{-1}$;
   b) counting a plurality of time-resolved signal intensity transition events detected within the discrete region and identifying the signal intensity transition events as a candidate signal produced by the repeated association and dissociation of said detectably labeled query probes with said immobilized single target nucleic acid molecule when the number of signal intensity transition events detected within the discrete region is greater than a threshold value; and
   c) detecting the target nucleic acid in the sample when said candidate signal is detected or when a value of a parameter characterizing said time-resolved signal intensity transition events indicates the presence of said single target nucleic acid molecule in said discrete region, wherein said parameter is selected from the group consisting of $\tau_{on}$, $\tau_{off}$, mean $\tau_{on}$, mean $\tau_{off}$, time-averaged $\tau_{on}$, time-averaged $\tau_{off}$, number of transitions, mean number of transitions, distribution of the number of transitions, mean of the distribution of the number of transitions, median of the distribution of the number of transitions, peak of the distribution of the number of transitions, standard deviation of the distribution of the number of transitions, and shape of the distribution of the number of transitions.

2. The method of claim 1 wherein the detectably labeled query probe is a nucleic acid or a fluorescent query probe.

3. The method of claim 1 wherein the discrete region of the solid support comprises a capture probe.

4. The method according to claim 1 wherein the parameter characterizing said time-resolved signal intensity transition events comprises one or more of;
   i) a dwell time of the detectably labeled query probe in the discrete region of the solid support that is different than the dwell time of the detectably labeled query probe in the discrete region of the solid support in the absence of the target nucleic acid;
   ii) a signal detected of the detectably labeled query probe in the discrete region of the solid support that is different than a signal detected of the detectably labeled query probe in the discrete region of the solid support in the absence of the target nucleic acid; or
   iii) the number of signal intensity transition events detected within the discrete region is different than the number of signal intensity transition events detected within the discrete region in the absence of the target nucleic acid.

5. The method according to claim 1 wherein counting a plurality of time-resolved signal intensity transition events comprises observing the discrete region using a single-molecule resolution technique.

6. The method according to claim 1 wherein the detectably labeled query probe comprises a fluorescent label.

7. The method according to claim 1 wherein the target nucleic acid is a ribonucleic acid.

8. The method of claim 3 wherein the capture probe comprises a nucleic acid, a locked nucleic acid, a peptide nucleic acid, a nucleic acid binding protein, or an antibody.

9. The method of claim 1 further comprising producing a kinetic fingerprint from the time-resolved signal intensity transition events.

10. The method of claim 1 further comprising performing statistical treatment of the repeated binding of said detectably labeled query probes with said single target nucleic acid molecule.

11. The method of claim 1 wherein Poisson statistical treatment of said signal intensity transition events is used to discriminate target nucleic acids from non-target nucleic acids or said threshold value is calculated from hidden Markov modeling or an edge detection algorithm.

12. The method of claim 1 further comprising comparing said value of said parameter with a second value of said parameter calculated from a positive control nucleic acid, a negative control nucleic acid, or a second target nucleic acid comprising a different nucleotide sequence.

13. The method of claim 1 wherein the detectably labeled query probe consists of 5 to 15 nucleotides and the signal intensity transition events detected within the discrete region are recorded with a fluorescence detector.

14. A method of detecting a difference in a nucleotide sequence of a first nucleic acid relative to a second nucleic acid, the method comprising:
   a) immobilizing a first single target nucleic acid molecule to a first discrete region of a solid support and immobilizing a second single target nucleic acid molecule to a second discrete region of said solid support, wherein the first target nucleic acid molecule comprises a first nucleotide sequence and the second target nucleic acid molecule comprises a second nucleotide sequence that is different than the first nucleotide sequence of the first target nucleic acid;
   b) providing detectably labeled query probes that associate and dissociate with one or both single target nucleic acids according to a kinetic rate constant $k_{on}$ or $k_{off}$ that is greater than 1 min$^{-1}$;
   c) counting a plurality of time-resolved signal intensity transition events detected within said first discrete region and identifying the signal intensity transition events as a first candidate signal produced by the repeated association and dissociation of said detectably labeled query probes with said first single target nucleic acid molecule when the number of signal intensity transition events detected within the first discrete region is greater than a threshold value and counting a plurality of time-resolved signal intensity transition events detected within said second discrete region and identifying the signal intensity transition events as a second candidate signal produced by the repeated association and dissociation of said detectably labeled query probes with said second single target nucleic acid molecule when the number of signal intensity transition events detected, wherein said detectably labeled query probes all comprise the same known nucleotide sequence and the degree of complementarity between the detectably labeled query probes and the first target nucleic acid is different than the degree of complementarity between the detectably labeled query probes and the second target nucleic acid;
   d) determining from the first candidate signal a first value of a parameter characterizing query probe association and dissociation with said first single target nucleic acid molecule and determining from the second candidate signal a second value of said parameter characterizing query probe association and dissociation with said second single target nucleic acid molecule; and e) detecting a difference in the nucleotide sequence of the first nucleic acid relative to the second nucleic acid by comparing the first value of said parameter and the second value of said parameter, wherein a difference in the first and second values of said parameter indicates that the first and second target nucleic acids have different nucleotide sequences and wherein said parameter is selected from the group consisting of $\tau$on, $\tau$off, mean $\tau$on, mean $\tau$off, time-averaged $\tau$on, time-averaged $\tau$off, number of transitions, mean number of transitions, distribution of the number of transitions, mean of the distribution of the number of transitions, median of the distribution of the number of transitions, peak of the distribution of the number of transitions, standard deviation of the distribution of the number of transitions, and shape of the distribution of the number of transitions.

15. The method of claim 14 comprising counting said signal intensity transition events detected within said first discrete region and said signal intensity transition events detected within said second discrete region in parallel.

16. The method of claim 14 wherein the first single target nucleic acid and the second single target nucleic acid differ in nucleotide sequence at one base.

17. The method of claim 14 wherein counting said signal intensity transition events detected within said first discrete region and said signal intensity transition events detected within said second discrete region comprises observing the first and second discrete regions using a single-molecule resolution technique.

18. A method for characterizing a target nucleic acid, the method comprising:
 a) immobilizing a single target nucleic acid molecule to a discrete region of a solid support and providing detectably labeled query probes that associate and dissociate with said single target nucleic acid according to a kinetic rate constant $k_{on}$ or $k_{off}$ that is greater than 1 min$^{-1}$;
 b) counting a plurality of time-resolved signal intensity transition events detected within the discrete region and identifying the signal intensity transition events as a candidate signal produced by the repeated association and dissociation of said detectably labeled query probes with said immobilized single target nucleic acid molecule when the number of signal intensity transition events detected within the discrete region is greater than a threshold value;
 c) producing a kinetic fingerprint from the candidate signal; and
 d) using the kinetic fingerprint to characterize the immobilized target nucleic acid according to at least one of the following:
  1) quantifying the nucleic acid in the sample;
  2) determining the conformation of the nucleic acid;
  3) determining the state of ligand binding to the target nucleic acid; or
  4) quantifying a ligand bound to the target nucleic acid or quantifying a ligand not bound to the target nucleic acid.

19. The method of claim 1 wherein the target nucleic acid molecule comprises 30 or fewer nucleotides or wherein the target nucleic acid molecule comprises a query region comprising 30 or fewer nucleotides.

20. The method of claim 1 wherein the threshold value is 10 signal intensity transition events occurring within the discrete region.

21. The method of claim 14 wherein:
 the first target nucleic acid molecule comprises 30 or fewer nucleotides or wherein the first target nucleic acid molecule comprises a query region comprising 30 or fewer nucleotides; and
 the second target nucleic acid molecule comprises 30 or fewer nucleotides or wherein the second target nucleic acid molecule comprises a query region comprising 30 or fewer nucleotides.

22. The method of claim 14, wherein the first or second target nucleic acid molecule comprises a wild-type nucleotide sequence.

23. The method of claim 18 wherein the target nucleic acid molecule comprises 30 or fewer nucleotides or wherein the target nucleic acid molecule comprises a query region comprising 30 or fewer nucleotides.

24. The method of claim 18 wherein the threshold value is 10 signal intensity transition events occurring within the discrete region.

* * * * *